(12) United States Patent
Wong et al.

(10) Patent No.: US 6,900,238 B1
(45) Date of Patent: May 31, 2005

(54) HIV PROTEASE INHIBITORS

(75) Inventors: Chi-Huey Wong, Rancho Santa Fe, CA (US); Deborah H. Slee, Cardiff, CA (US); Karen Laslo, Boulder, CO (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/077,712

(22) PCT Filed: Dec. 9, 1996

(86) PCT No.: PCT/US96/19571

§ 371 (c)(1),
(2), (4) Date: Jul. 9, 1999

(87) PCT Pub. No.: WO97/21100

PCT Pub. Date: Jun. 12, 1997

Related U.S. Application Data

(63) Continuation of application No. PCT/US96/19571, filed on Dec. 9, 1996, which is a continuation of application No. 08/568,532, filed on Dec. 7, 1995.

(51) Int. Cl.$^7$ .......................... A01N 43/36; C07F 9/02; C07D 207/00

(52) U.S. Cl. ...................... 514/423; 548/538; 548/412

(58) Field of Search ................................. 548/412, 538; 514/423

(56) References Cited

U.S. PATENT DOCUMENTS

| | | |
|---|---|---|
| 5,171,662 A | 12/1992 | Shjarma |
| 5,436,131 A | 7/1995 | Condra et al. |
| 5,532,124 A | 7/1996 | Block et al. |
| 5,545,640 A | 8/1996 | Beaulieu et al. |

FOREIGN PATENT DOCUMENTS

| WO | WO 93/13066 | 12/1992 |
|---|---|---|

OTHER PUBLICATIONS

Debouck (1992) AIDS Research and Human Retroviruses vol. 8(2):153–164.*
Ocain et al. (1992) J. Med. Chem. vol. 35:451–456.*
Slee et al., J. Am. Chem. Soc, 1995, 117, 11867–78.*
Tam, et al., "Intriguing Structure–Activity Relations Underlie the Potent Inhibition of HIV Protease by NorstatineBased Peptides", *J. Med. Chem.* 35: 1318–1320 (1992).
Waller, et al., "Three–Dimensional QSAR of Human Immunodeficiency Virus (I) Protease Inhibitors. 1. A CoMFA Study Employing Experimentally–Determined Alignment Rules", *J. Med. Chem.* 36: 4152–4160 (1993).
Munoz, et al., "α–Ketoamide Phe–Pro Isostere as a New Core Structure for the Inhibition of HIV Protease", *Bioorg. Med. Chem.* 2: 1085–1090 (1994).

Kitazaki, et al., "Synthesis and Human Immunodeficiency Virus (HIV)–1 Protease Inhibitory Acitivty of Tripeptide Analogues Containing a Dioxoethylene Moiety", *Chem. Pharm. Bull.* 42: 2636–2640 (1994).
Natarajan, et al., "Ketomethyldipeptides 1. A New Class of Angiotensin Converting Enzyme Inhibitors", *Biochem. Biophys. Res. Commun.* 124: 141–147 (1984).
Gordon, et al., "Ketomethyldipeptides II. Effect of Modifications of the α–Aminoketone Portion on Inhibition of Angiotensin Converting Enzyme", *Biochem. Biophys. Res. Commun.* 124: 148–155 (1984).
Tanabe–Tochikura, et al., "Anti–Human Immunodeficiency Virus (HIV) Agents are also Potent and Selective Inhibitors of Feline Immunodeficiency Virus (FIV)–Induced Cytopathic Effect: Development of a New Method for Screening of anti–FIV Substances in vitro", *Antiviral Res.* 19: 161–172 (1992).
Ocain, et al., "αKeto Amide Inhibitors of Aminopeptidases", *J. Med. Chem.* 35: 451–456 (1992).
Debouck, "The HIV–1 Protease as a Therapeutic Target for AIDS", *Aids Research and Human Retroviruses* 8: 153–164 (1992).
Yuan, et al., "Development of Selective Tight–Binding Inhibitors of Leukotriene $A_4$ Hydrolase", *J. Med. Chem.* 36: 211–220 (1993).
Elder, et al., "Identification of Proteolytic Processing Sites within the Gag and Pol Polyproteins of Feline Immunodeficiency Virus", *J. Virol.* 67: 1869–1876 (1993).
Arai, et al., "Synthesis of Prolyl Endopeptidase Inhibitors and Evaluation of Their Structure–Activity Relationships: In Vitro Inhibition of Prolyl Endopeptidase from Canine Brain", *Chem. Pharm. Bull.* 41: 1583–1588 (1993).
Patel, et al., "Activated Ketone Based Inhibitors of Human Renin", *J. Med. Chem.* 36: 2431–2447 (1993).
Li, et al., "Peptide α–Keto Ester, α–Keto Amide, and α–Keto Acid Inhibitors of Calpains and Other Cysteine Proteases", *J. Med. Chem.* 36: 3472–3480 (1993).

(Continued)

*Primary Examiner*—Michael Meller
(74) *Attorney, Agent, or Firm*—Donald G. Lewis

(57) ABSTRACT

Combinatorial libraries of HIV and FIV protease inhibitors are characterized by α-keto amide or hydroxyethylamine core structures flanked by on one side by substituted pyrrolidines, piperidines, or azasugars and on the other side by phenylalanine, tyrosine, or substituted tyrosines. The libraries are synthesized via a one step coupling reaction. Highly efficacious drug candidates are identified by screening the libraries for binding and inhibitory activity against both HIV and FIV protease. Drug candidates displaying clinically useful activity against both HIV and FIV protease are identified as being potentially resistive against a loss of inhibitory activity due to development of resistant strains of HIV.

4 Claims, 34 Drawing Sheets

OTHER PUBLICATIONS

Elder, et al., "Molecular Properties of Feline Immunodeficiency Virus (FIV)", *Infectious Agents and Disease 2*: 361–374 (1994).

Kaneto, et al., "A Rapid and Simple Screening Method for HIV–I Protease Inhibitors Using Recombinant *Escherichia coli*", *J. Antibiotics 47*: 492–495 (1994).

Mellors, et al., "Mutations in HIV–1 Reverse Transcriptase and Protease Associated with Drug Resistance", *International Antiviral News 3*: 8–13 (1995).

Wang, et al., "Synthetic Chemical Diversity: Solid Phase Synthesis of Libraries of $C_2$ Symmetric Inhibitors of HIV Protease Containing Diamino Diol and Diamino Alcohol Cores", *J. Med. Chem. 38*: 2995–3002 (1995).

Thaisrivongs, et al., "Structure–Based Design of Novel HIV Protease Inhibitors: Carboxamide–Containing 4–Hydroxycoumarins and 4–Hydroxy–2–pyrones as Potent Nonpeptidic Inhibitors", *J. Med. Chem. 38*: 3624–3637 (1995).

* cited by examiner

1a $K_i = 6\mu M$

1b $K_i = 405$ nM

2 R = H; $K_i = 214$ nM
73 R = OBn (cis); $K_i = 65$ nM
74 R = OMe (trans); $K_i = 220$ nM
75 R = OBn (trans); $K_i = 318$ nM $K_i = >50\ \mu M$ $K_i = 230\ \mu M$

4 IC$_{50}$=1.8mM

5 IC$_{50}$=100μM

6 IC$_{50}$=1.6mM

7 IC$_{50}$=60μM

8 IC$_{50}$=17μM

38 (R=Me) IC$_{50}$=2.9μM
39 (R=Bn) IC$_{50}$=3.9μM

R = various side groups
R₁ = CBZ, BOC or other N-protecting group
R₂ = various protecting groups (H, Methyl, Benzyl, p-methoxy benzyl, tertbutyldimethylsilyl, tertbutyldiphenylsilyl etc.)

$R_1$ = various protecting groups (H, Methyl, Benzyl)

variously substituted pyrrolidines and piperidine analogues $AA_1$, $AA_2$ = natural and unnatural amino acids

1050

1051

1052

1053

1054

1055

1056

1057

1058

ALTERNATIVES USING THE FOLLOWING BROMIDES:

WHEREIN R =   WHEREIN R =

1059   1060

HIV PROTEASE INHIBITORS

This application is a continuation of PCT/US96/19571 filed Dec. 9, 1996 which is a continuation of U.S. Ser. No. 08/568,532 which was filed Dec. 7, 1995.

STATEMENT OF GOVERNMENT RIGHTS

This invention was made with government support under Contract Nos. GM 48870 and GM 44154 by the National Institutes of Health. The government has certain rights in the invention.

FIELD OF INVENTION

The invention relates to HIV and FIV protease inhibitors. More particularly, the invention is directed to combinatorial libraries of HIV and FIV protease inhibitors characterized by α-keto amide or hydroxyethylamine core structures flanked by on one side by substituted pyrrolidines, piperidines, or azasugars and on the other side by phenylalanine, tyrosine, or substituted tyrosines. The invention is also directed to methods for making such libraries, to the disclosed compounds made by such method, and to a method for screening such libraries for identifying candidate drugs which have clinically useful activity and which are potentially resistive against loss of inhibitory activity due to development of resistant strains of HIV.

BACKGROUND

Human immunodeficiency virus protease (HIV PR) is an important target for the inhibition of viral replication. Though many potent in vitro inhibitors have been developed, most of them are either inactive or toxic in vivo, or mutant forms of the virus emerge which are resistant. (See J. H. Condra, et al., *Nature* (1995): vol. 374, 569–571; M. Markowitz, et al., *J. Virol.* (1995): vol. 69, 701; D. J. Kempf, et al., *Proc. Natl. Acad. Sci. USA* (1995): vol. 92, 2484–2488; A. K. Ghosh, et al., *J. Med. Chem.* (1994): vol. 37, 2506–2508; P. Y. Lam, et al., *Science* (1994) vol. 263, 380–384; N. A. Roberts, et al., *Science* (1990): vol. 248, 358; and E. E. Kim, et al., *J. Am. Chem. Soc.* (1995): vol. 117, 1181–1182.)

The lack of animal systems to test the efficacy of the inhibitors further slows down the drug development process. Recently a similar protease has been identified in the life cycle of feline immunodeficiency virus (FIV). (R. L. Talbott, et al., *Proc. Natl. Acad. Sci. USA* (1989): vol. 86, 5743–5747; and N. C. Pedersen, et al. *Science* (1987): vol. 235, 790–793.) FIV is a virus which leads to clinical symptoms comparable to those observed in human acquired immune deficiency syndrome (AIDS). Studies have shown that up to 14% of the cats surveyed in the USA and Canada are infected with FIV. (J. K., Yamamoto, et al., *JAVMA* (1989): vol. 194, 213–220.) In Japan, the figure is 28.9%. (T. Ishida, et al., *JAVMA* (1989): vol. 194, 221–225.

In drug resistant mutants of HIV, there are at least six cases where HIV PR residues mutate to the structurally aligned residue found in FIV PR. The amino acid changes in HIV PR are V32I (137-FIV), L90M (M107-FIV), NB8D (D105-FIV), I50V (V59'-FIV), K20I (I25-FIV), and Q29K (K109-FIV). For a list of resistant HIV PR mutants is disclosed by J. W. Mellors, et al. (*International Antiviral News* (1995): vol. 3, 8–13.) The structure alignment was derived from the X-ray crystal structure of FIV PR solved by A. Wlodawer (reference 36). Superimposition of the two proteases based on their X-ray structures indicates similarities between the two proteases and the drug resistant HIV proteases.

HIV PR is a 99 amino acid aspartyl protease which functions as a homodimer. (M. A. Navia, et al., *Nature* (1989): vol. 337, 615–620; and D. D. Loeb, Virol. (1989): vol. 63, 111–121.) FIV PR is also a homodimeric aspartyl protease which consists of 116 amino acid residues. (J. H. Elder, *Infectious Agents and Disease* (1994): vol. 2, 361–374.) Both HIV and FIV proteases are responsible for the processing of viral gag and gag-pol polyproteins into structural proteins and enzymes essential for the proper assembly and maturation of full infectious virions. (S. K. Thompson, *Bioorg. Med. Chem. Lett.* (1994): vol. 4, 2441–2446.) In particular HIV and FIV proteases show high specificity for the selective cleavage of the Tyrosine/Phenylalanine-Proline amide bonds in the Matrix-Capsid domain of the gag-pol polyproteins, a specificity not exhibited by mammalian cellular proteases which are not known to efficiently hydrolyze peptide bonds involving the proline nitrogen. (C. Debouck, *Aids Research and Human Retroviruses* (1992): vol. 8, 153–164; and J. H. Elder, J. Virol. (1993): vol. 67, 1869–1876.) It is this specificity that makes HIV PR an attractive target for inhibition. A comparison of the amino acid sequence about the matrix capsid cleavage site (Tyrosine~Proline bond) in both HIV and FIV is provided below. As can be seen the residues about the cleavage site are the same at four positions, $P_3$, $P_1$, $P_{1'}$, and $P_{2'}$. It is disclosed herein that, due to these similarities, certain HIV PR inhibitors also inhibit FIV PR.

| | $P_4$ | $P_3$ | $P_2$ | $P_1$ | | $P_{1'}$ | $P_{2'}$ | $P_{3'}$ | $P_{4'}$ |
|---|---|---|---|---|---|---|---|---|---|
| HIVPR | Ser | Gln | Asn | Tyr | ~ | Pro | Ile | Val | Gln |
| FIVPR | Pro | Gln | Ala | Tyr | ~ | Pro | Ile | Gln | Thr |

Activated ketones, in general, have been shown to inhibit most kinds of proteases (Barrett et. al., *Proteinase Inhibitors*; Research monographs in cell and tissue physiology; Dingle, J. T., Gordon, J. L., General Eds.; Elsevier Science Publishers; Amsterdam, 1986). In particular, a recent study shows the design of three different classes of activated ketones which inhibit the aspartyl protease, renin. These potent analogs display $IC_{50}$ values from 4000 nM to 4.1 nM and include 1,1,1-trifluoromethyl ketones, α-keto esters, and α-diketones as the activated ketone functionalities (Patel et. al. *J. Med Chem.* 1993, 36, 2431).

The α-keto-amide core structure is isosterically analogous to the activated ketones but is more potent than the reported hydroxyethylamine or phosphinic acid HIV protease inhibitors that are mechanism-based isosteric core structures.

The α-keto-amide core structure has been used in inhibitors of various enzymes which include serine and cysteine proteases, hydrolases and aminopeptidases. As an example, a series of dipeptidyl and tripeptidyl α-keto amides have been synthesized and evaluated as potent inhibitors for cysteine proteases which include enzymes calpain I, calpain II, cathepsin B, and papain (Li et. al. J. Med. Chem. 1993, 36, 3472). Another study has identified α-keto amide analogs as inhibitors of an epoxide hydrolase (Wong et. al. *J. Med. Chem.* 1993, 36, 211). Additionally, the inhibition of arginyl aminopeptidase ($K_i$=1.5 uM), cytosol aminopeptidase ($K_1$=1.0 μM) and microsomal aminopeptidase ($K_1$=2.5 μM) has been observed from α-keto amide analogs which can be derived from 3-amino-2-oxo-4-phenylbutanoic acid amides. (Rich et. al. J. Med Chem. 1992, 35, 451).

The activity of dipeptide isosteres is often enhanced by addition of amino acid residues to either the N and C-terminus of the isostere to improve binding in the active site. The prior art provides examples of such inhibitors which include renin, aspartyl proteases and procine pepsin inhibitors (Rich et. al. J. Med Chem. 1992, 35, 451). The resulting inhibitors generally exhibit high binding affinity to HIV protease. They display, however, instability and/or poor oral bioavailability.

The related art has provided examples of α-keto amide inhibitors of aminopeptidases which contain an unsubstituted proline moiety in the molecule. In particular, Gordon and co-workers have described α-keto amide inhibitors with an unsubstituted proline ring for the themetalloprotease angiotensin converting enzyme (ACE) (Gordon et. al. Biochem. Biophys. Res. Commun. 1984, 124, 141). Additionally, Arai et. al. (Chem. Pharm. Bull. 41, 9, 1583) have reported potent inhibitory activity by a prolyl endopeptidase (PEP) inhibitor (N-[N-(4-phenylbutanoyl)-L-prolyl] pyrrolidine).

What is needed are combinatorial libraries of HIV and FIV protease inhibitors and simple synthetic methods for making same.

What is needed is a class of HIV and FIV protease inhibitor having enhanced possibilities of variability at the $P_1$, and $P_1'$ positions for improving the binding between the enzyme and its inhibitor.

What is needed are methods for screening combinatorial libraries of HIV and FIV protease inhibitors for identifying candidates having both clinically useful inhibitory activity and a potential resistivity to a loss of inhibitory activity due to development of resistant strains of HIV.

What is needed are new HIV and FIV protease inhibitors having clinically useful inhibitory activity and a resistivity to a loss of inhibitory activity due to development of resistant strains of HIV.

SUMMARY

It is disclosed herein that FIV PR provides a good model of drug resistance in retroviral proteases. Testing candidate drugs with respect to their inhibitory activity against both HIV and FIV proteases and determining which inhibitors are simultaneously efficacious against both of these mechanistically identical proteases, identifies inhibitors of HIV protease which are potentially less prone to resistance development. Candidate drugs which are successfully screened in vitro may then be tested in cats as model systems on which to test HIV PR inhibitors in vivo.

Accordingly, one aspect of the invention is directed to a method for identifying a drug candidate as an HIV protease inhibitor potentially resistive against loss of inhibitory activity due to development of resistant strains of HIV. The method employs the following steps:

Step A: determining whether the drug candidate has a binding activity with respect to HIV protease of less than 1 μM;

Step B: determining whether the drug candidate has an inhibitory activity with respect to HIV protease of less than 1 μM;

Step C: determining whether the drug candidate has a binding activity with respect to FIV protease of less than 1 μM; and Step D: determining whether the drug candidate has an inhibitory activity with respect to FIV protease of less than 1 μM.

If the drug candidate is determined to have binding and inhibitory activities with respect to both HIV protease and FIV protease of less than 1 μM in each of the above steps, then the drug candidate is selected as an HIV protease inhibitor potentially resistive against loss of inhibitory activity due to development of resistant strains of HIV.

The above method may be applied either to individual drug candidates or to a library of drug candidates.

Another aspect of the invention is directed to methods for synthesizing drug candidates which potentially inhibit HIV protease. More particularly, the drug candidates are of a type which include an N-terminus, a C-terminus, and an α-keto amide core structure linking the N-terminus and the C-terminus. The N-terminus incudes an aromatic amino acid residue selected from the group consisting of phenylalanine, tyrosine, and O-substituted tyrpsines. The aromatic amino acid includes a carbonyl group for linking to and incorporation into the α-keto amide core structure. The C-terminus includes a heterocyclic ring having a ring nitrogen and one or more substitutions. The ring nitrogen of the C-terminus is linked to and incorporated into the α-keto amide core structure. The synthetic method includes the following step:

Step A: providing an N-terminus precursor identical to the N-terminus except that the carbonyl group is replaced by an α-hydroxyl acid group;

Step B: providing a C-terminus precursor identical to the C-terminus except that the ring nitrogen forms a secondary amine;

Step C: coupling the N-terminus precursor of step A to the C-terminus precursor of step B to form a drug candidate precursor identical to the drug candidate except that the α-keto amide core structure of the drug candidate is replaced by an α-hydroxylamide core structure linking and incorporating the carbonyl group of the N-terminus and the ring nitrogen of the C-terminus; and then;

Step D: oxidizing the α-hydroxylamide core structure of the drug candidate precursor of step C for forming the α-keto amide core structure and the drug candidate.

The above synthetic method may also be adapted for synthesizing combinatorial libraries of HIV and FIV protease inhibitors containing nxm drug candidates. The above synthetic method is modified by providing nxm reaction vessels, loading each of the n N-terminus precursors into m of the reaction vessels, and then loading each of the m C-terminus precursors into n of reaction vessels so as to form nxm admixtures of N-terminus precursor and C-terminus precursors. Then, each of the nxm admixtures is allowed to undergo a coupling reaction in which the N-terminus precursor couples to the C-terminus precursor to form nxm drug candidate precursors. The drug precursor candidates are identical to the nxm drug candidates except that the α-keto amide core structure of the nxm drug candidates is replaced by an α-hydroxylamide core structure linking and incorporating the carbonyl group of the N-terminus and the ring nitrogen of the C-terminus. Finally, the α-hydroxylamide core structure of each of the nxm drug candidate precursors is oxidized so as to form the α-keto amide core structure of the desired drug candidate.

A further aspect of the invention is directed to combinatorial libraries nxm drug candidates characterized by having a α-keto amide core structure and a potential inhibitory activity with respect to HIV protease. The drug candidates are characterized by having an N-terminus selected from n N-termini where n is two or greater, a C-terminus selected from m C-termini where m is two or greater, and a α-keto amide core structure which links the N-terminus to the C-terminus. Each of the n N-termini includes an aromatic amino acid residue selected from the group consisting of phenylalanine, tyrosine, and O-substituted tyrosine. The aromatic amino acid includes a hydroxyethyl group in lieu of a carbonyl group which is linked to and incorporated into the α-keto amide core structure. Each of the m C-termini includes a heterocyclic ring having a ring nitrogen and one or more substitutions. The ring nitrogen of the C-terminus is linked to and is incorporated into the α-keto amide core structure.

Another aspect of the invention is directed to combinatorial libraries of nxm drug candidates characterized by having a hydroxyethylamine core structure and a potential inhibitory activity with respect to HIV protease. The drug candidates are characterized by having an N-terminus selected from n N-termini where n is two or greater, a C-terminus selected from m C-termini where m is two or greater, and a hydroxyethylamine core structure which links the N-terminus to the C-terminus. Each of the n N-termini includes an aromatic amino acid residue selected from the group consisting of phenylalanine, tyrosine, and O-substituted tyrosine. The aromatic amino acid includes a hydroxyethyl group in lieu of a carbonyl group which is linked to and incorporated into the hydroxyethylamine core structure. Each of the m C-termini includes a heterocyclic ring having a ring nitrogen and one or more substitutions. The ring nitrogen of the C-terminus is linked to and is incorporated into the hydroxyethylamine core structure.

Another aspect of the invention is directed to a series of improved mechanism based inhibitor of HIV or FIV aspartyl protease. Each of the improved mechanism based inhibitors is of a type having an N-terminus, a C-terminus, and a core structure for linking the N-terminus to the C-terminus. The N-terminus includes an aromatic amino acid residue linked to the core structure. The C-terminus includes a heterocyclic ring having a ring nitrogen linked to the core structure. The core structure is isosteric with a scissile amide bond of an HIV or FIV aspartyl protease substrate.

In the first embodiment of improved mechanism based inhibitor, the core structure is an α-keto amide and the heterocyclic ring of the N-terminus is a pyrrolidine having at least one substituent other than carboxylic acid and carboxymethyl ester. Examples of this first embodiment of improved mechanism based inhibitors are provided as follows:

22

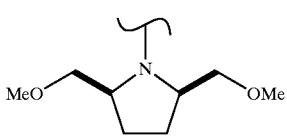

23

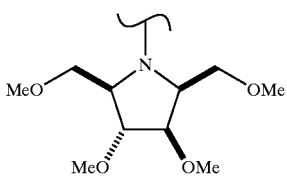

40

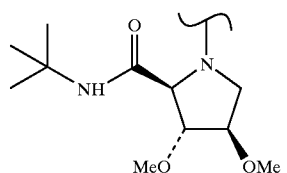

-continued

24

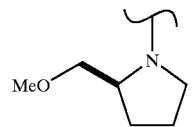

16

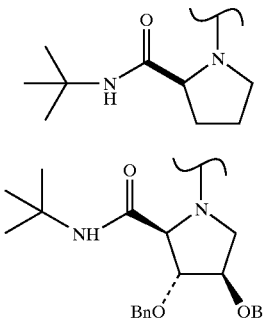

42

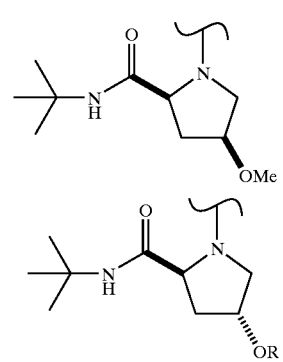

25

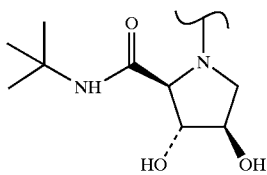

36 R = Me
37 R = Bn

44

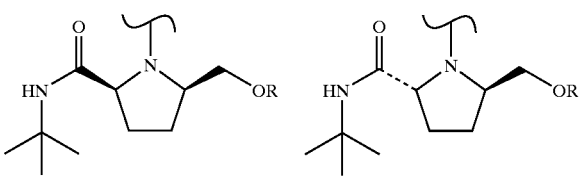

46 R = H; 47 R = Bn, 48 R = Me    52 R = H; 53 R = Bn, 54 R = Me

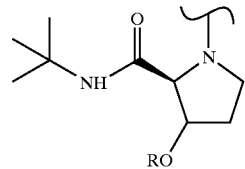

58 R = H; 59 R = Bn, 60 R = Me (cis
64 R = H; 65 R = Bn, 66 R = Me (tr

100

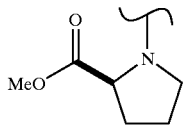

-continued

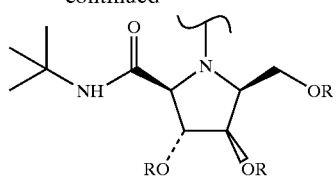

101 R = H; 102 R = Bn, 103 R = Me

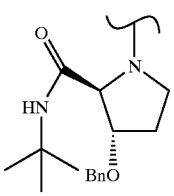

1052

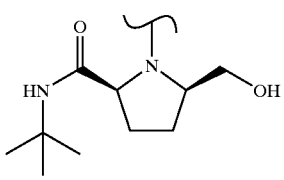

1053

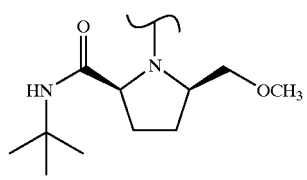

1055

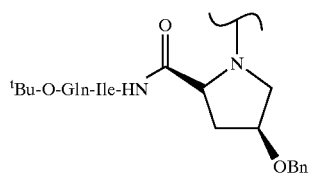

tBu-O-Gln-Ile-HN

1056

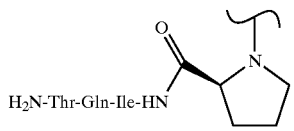

H₂N-Thr-Gln-Ile-HN

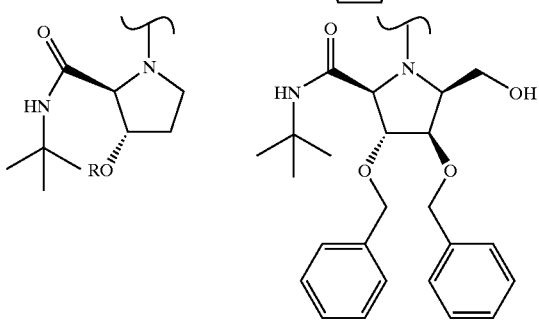

where:

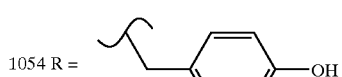

1054 R =

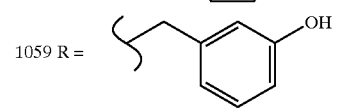

1059 R =

-continued

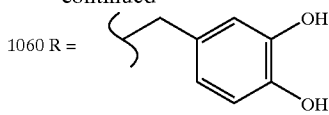

1060 R =

In a second embodiment of improved mechanism based inhibitor, the core structure is an α-keto amide and the heterocyclic ring of the N-terminus is a piperadine or azasugar. Examples of piperadines and azasugars employed in this second embodiment of improved mechanism based inhibitors are provided as follows:

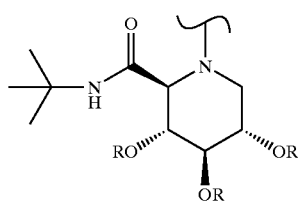

R = 85 H, 86 Me, 87 Bn

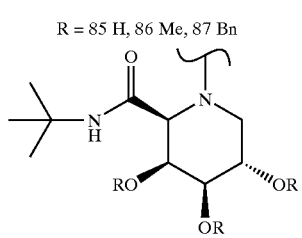

R = 88 H, 89 Me, 90 Bn

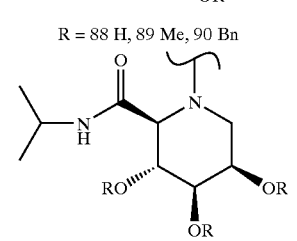

R = 91 H, 92 Me, 93 Bn

94

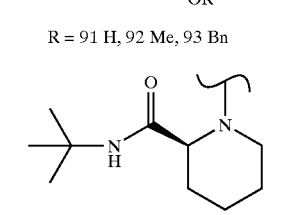

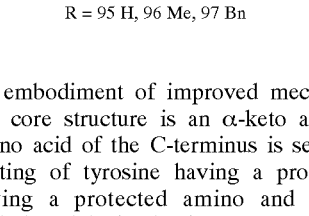

R = 95 H, 96 Me, 97 Bn

In a third embodiment of improved mechanism based inhibitor, the core structure is an α-keto amide and the aromatic amino acid of the C-terminus is selected from a group consisting of tyrosine having a protected amino, tyrosine having a protected amino and a substituted hydroxyl, and phenylalanine having a protected amino protected by carbobenzyloxy. Examples of this third embodiment of improved mechanism based inhibitors are provided as follows:

Is

[Structure 5: R₂O-phenyl-CH₂-CH(NHR₁)-C(=O)-C(=O)-N(pyrrolidine-R)]

[Structure 15: R₂O-phenyl-CH₂-CH(NHR₁)-C(=O)-C(=O)-N(piperidine-R)]

[Structure 25: phenyl-CH₂-CH(NHR₁)-C(=O)-C(=O)-N(pyrrolidine-R)]

[Structure 35: phenyl-CH₂-CH(NHR₁)-C(=O)-C(=O)-N(piperidine-R)]

wherein R is selected from the group consisting of hydrogen, hydroxy, benzyloxy, alky$_{(c1-c4)}$-oxy, o-methoxy-benzyloxy, m-methoxy-benzyloxy, p-methoxy-benzyloxy, o-methoxy-nitrobenzyloxy, m-methoxy-nitrobenzyloxy, p-methoxy-nitrobenzyloxy, acetonide, benzylidene, 3-oxymethyl-catechol, 4-oxymethyl-catechol; $R_1$ is selected from the group consisting of carbobenzyloxy (CBZ), tert-butoxycarbonyl (t-BOC), acyl; $R_2$ is selected from the group consisting of hydrogen, benzyl, alkyl $_{(c1-c4)}$, o-methoxy-benzyl, m-methoxy-benzyl, p-methoxy-benzyl, o-methoxy-nitrobenzyl, m-methoxy-nitrobenzyl, p-methoxy-nitrobenzyl, 3-methylene-catechol, 4-methylene-catechol.

In a fourth embodiment of improved mechanism based inhibitor, the core structure is an hydroxyethylamine and the heterocyclic ring of the N-terminus is a pyrrolidine having at least one substituent other than carboxylic acid and carboxymethyl ester. Examples of pyrrolidines employed in this fourth embodiment of improved mechanism based inhibitors are provided as follows:

22 [Pyrrolidine with MeO-CH₂ and CH₂-OMe substituents]

23 [Pyrrolidine with MeO-CH₂, CH₂-OMe, MeO, OMe substituents]

40 [t-Bu-NH-C(=O)-pyrrolidine with MeO, OMe substituents]

24 [Pyrrolidine with MeO-CH₂ substituent]

16 [t-Bu-NH-C(=O)-pyrrolidine]

42 [t-Bu-NH-C(=O)-pyrrolidine with BnO, OBn substituents]

25 [t-Bu-NH-C(=O)-pyrrolidine with OMe substituent]

36 R = Me
37 R = Bn
[t-Bu-NH-C(=O)-pyrrolidine with OR substituent]

44 [t-Bu-NH-C(=O)-pyrrolidine with HO, OH substituents]

46 R = H; 47 R = Bn, 48 R = Me [HN-C(=O)-pyrrolidine-CH₂-OR with t-Bu]

52 R = H; 53 R = Bn, 54 R = Me [HN-C(=O)-pyrrolidine-CH₂-OR with t-Bu, different stereochemistry]

-continued

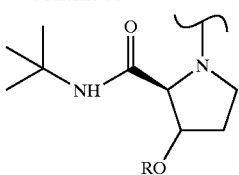

58 R = H; 59 R = Bn, 60 R = Me (cis)
64 R = H; 65 R = Bn, 66 R = Me (tra

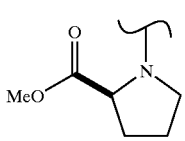

100

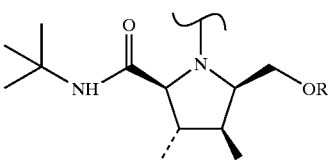

101 R = H; 102 R = Bn, 103 R = Me

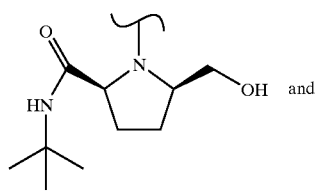  and

1051

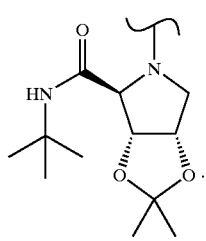

1058

In a fifth embodiment of improved mechanism based inhibitor, the core structure is hydroxyethylamine and the heterocyclic ring of the N-terminus is a piperadine or azasugar. Examples of piperadines and azasugars employed in this fifth embodiment of improved mechanism based inhibitors are provided as follows:

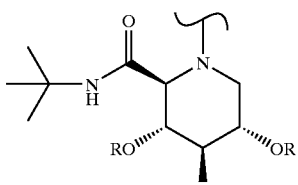

R = 85 H, 86 Me, 87 Bn

-continued

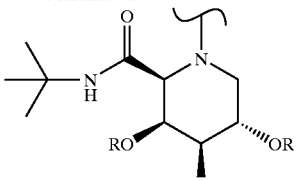

R = 88 H, 89 Me, 90 Bn

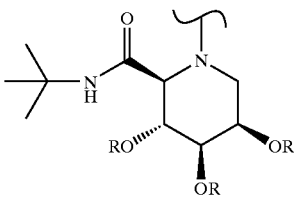

R = 91 H, 92 Me, 93 Bn

94

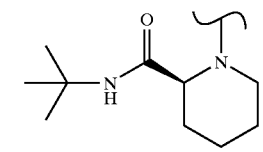

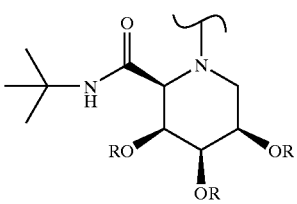

R = 95 H, 96 Me, 97 Bn

In a sixth embodiment of improved mechanism based inhibitor, the core structure is hydroxyethylamine and the aromatic amino acid of the C-terminus is selected from a group consisting of tyrosine having a protected amino, tyrosine having a protected amino and a substituted hydroxyl, and phenylalanine having a protected amino protected by carbobenzyloxy. Examples of this sixth embodiment of improved mechanism based inhibitors are provided as follows:

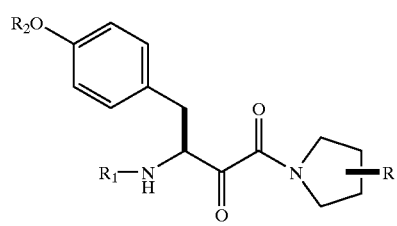

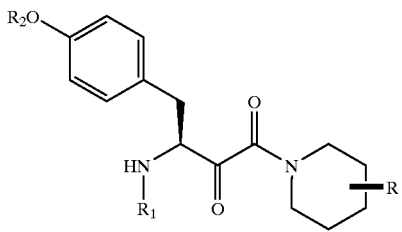

-continued

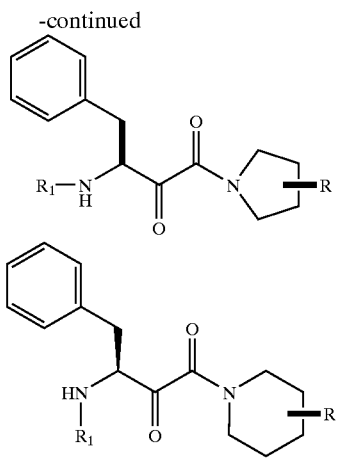

wherein R is selected from the group consisting of hydrogen, hydroxy, benzyloxy, alkyl$_{(c1-c4)}$-oxy, o-methoxy-benzyloxy, m-methoxy-benzyloxy, p-methoxy-benzyloxy, o-methoxy-nitrobenzyloxy, m-methoxy-nitrobenzyloxy, p-methoxy-nitrobenzyloxy, acetonide, benzylidene, 3-oxymethyl-catechol, 4-oxymethyl-catechol; $R_1$ is selected from the group consisting of carbobenzyloxy (CBZ), tert-butoxycarbonyl (t-BOC), acyl; $R_2$ is selected from the group consisting of hydrogen, benzyl, alkyl$_{(c1-c4)}$, o-methoxy-benzyl, m-methoxy-benzyl, p-methoxy-benzyl, o-methoxy-nitrobenzyl, m-methoxy-nitrobenzyl, p-methoxy-nitrobenzyl, 3-methylene-catechol, 4-methylene-catechol.

DETAILED DESCRIPTION

One aspect of the invention is directed to a new class of the HIV/FIV PR inhibitors, viz. α-keto amide inhibitors. The mode of action of the α-keto amide inhibitor is of particular interest as it represents a new type of mechanism-based enzyme inhibition which can lead to the development of tight-binding inhibitors to overcome the problem of resistance.

Figure 3:
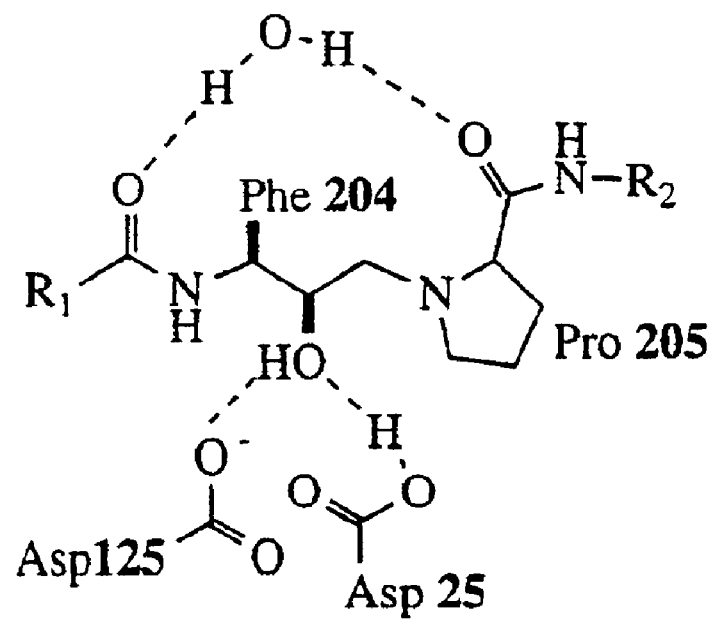
FIG. 3 illustrates hydrogen bond interactions between a hydroxyethylamine isostere and the active site of HIV PR as observed from X-ray crystallography.

When assayed against HIV PR, the novel α-keto amide 1 (FIG. 3) was found to have a $K_i$ of 6 μM. Subsequent studies have shown that a simple modification of the N- and C-terminal protecting groups to give 2 (FIG. 3) enhances the potency of this core isostere against HIV PR, to give a $K_1$ of 214 nM.

The increase in activity in compound 2 may be due to favorable hydrophobic interactions between the protecting groups (i.e. the Cbz-protecting group and the t-Bu group) and the active site of HIV PR. The Boc-protecting group is also hydrophobic but is shorter and sterically more bulky, making it unable to extend effectively into the appropriate hydrophobic binding pocket. This result demonstrates how simple modifications of the core isostere can significantly improve its potency. It is disclosed that the potency of the α-keto amide 2 can be improved by introduction of additional complementary groups to the proline ring moiety. Computer modeling (Insight/Discover) indicates that attachment of hydrophobic groups to the proline ring moiety will enhance binding. It is disclosed that addition of a cis-benzyl ether to C-4 of the proline moiety increased binding 3-fold ($K_1$=65 nM).

Figure 4:
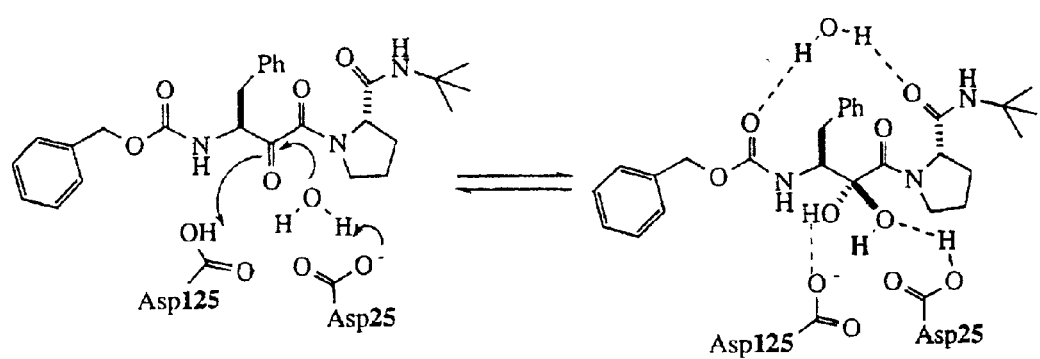
FIG. 4 illustrates a general acid-base mechanism for inhibitor 2 interaction with HIV PR aspartate groups.

The activity of the isostere 2 can be then compared to that of the identically substituted α-hydroxy amide precursors 23 and 24. The S-diastereomer 24 ($IC_{50}$=2 μM) is disclosed to be more potent than the R-diastereomer 23 ($IC_{50}$=300 μM), but less active than 2. The high potency of the α-hydroxy amide 24 implies that the hydroxyl group is hydrogen bonding more effectively with the catalytic carboxylic acid groups of HIV PR than in compound 23, similar to that observed in the X-ray structure of a hydroxyethylamine inhibitor enzyme complex (FIG. 4). The stereochemistry of the isosteres 23 and 24 was determined by $^1H$ NMR studies on the R- and S-Mosher esters derived from the S-α-hydroxy ester 19.

Figure 5:
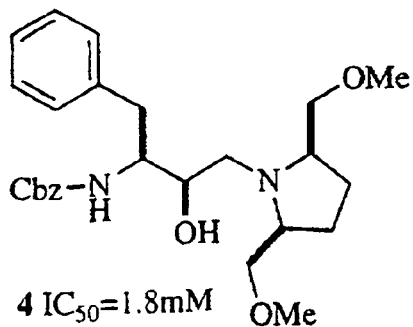
FIG. 5 illustrates inhibitory activity of variously substituted pyrrolidine analogues against HIV PR.
Figure 5:
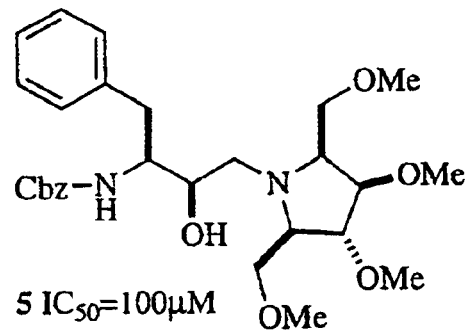
Figure 5:
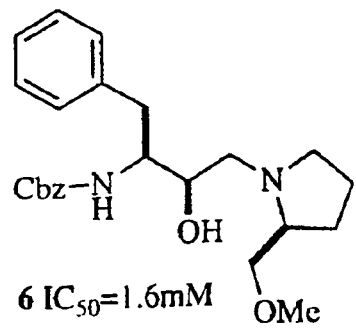
Figure 5:
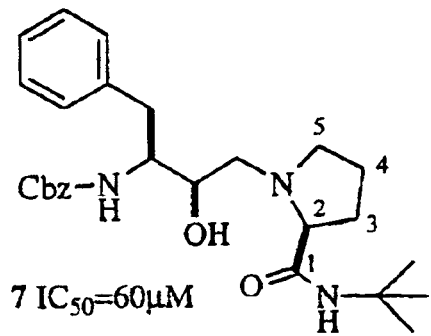
Figure 5:
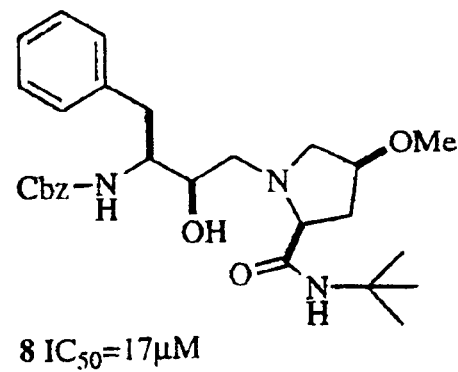
Figure 5:
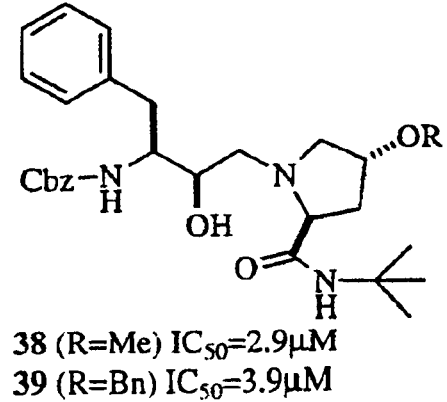
Figure 6:
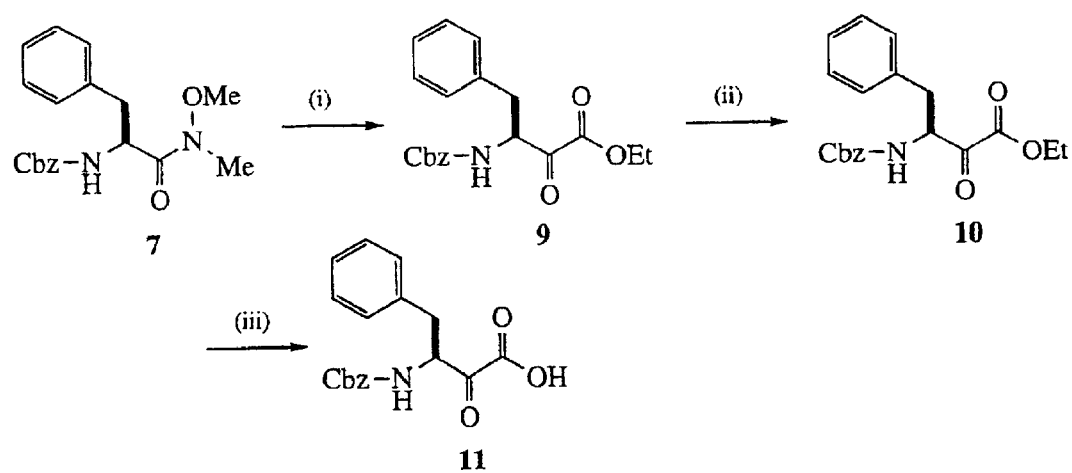
FIG. 6 illustrates the synthesis of compound 11. The steps indicated are as follows: (i) t-BuLi, ethyl vinyl ether, MgBr$_2$, THF; (ii) O$_3$, CH$_2$Cl$_2$; (iii) 0.17N LiOH, MeOH/H$_2$O, 2:1, 98%.

The ketone moiety of the α-keto amide 2 is disclosed to be hydrated and is hydrogen bonding in a similar manner to that of compound 23. However in this case, $^{13}C$ NMR studies on compound 2 in deuterated $DMSO/D_2O$ (5:1) indicates that, in the presence of water, the ketone moiety of the α-keto amide remains unhydrated even after incubation for 24 hours (FIG. 5). This indicates that the ketone moiety of 2 is stable in the presence of water and is therefore difficult to hydrate in the absence of a catalyst. It is likely that hydration of the ketone moiety takes place within the active site of HIV PR as illustrated in FIG. 6, and the resulting hydrate is then stabilized through hydrogen bonding interactions with the aspartate residues of the enzyme. The hydrated form of 2 is considered to be a good transition state mimic based on the model presented in FIG. 6.

Time dependent assays do not exhibit time dependent inhibition, indicating that if the active form of the α-keto amide 2 is indeed the hydrate, the hydration step must be rapid or 2 itself is the active form. To further investigate the mode of action, the X-ray structure of the complex between the α-keto amide 2 and HIV PR was determined and the result indicated that the α-keto amide is hydrated, supporting the enzyme-assisted hydration mechanism (FIG. 7).

Figure 7:
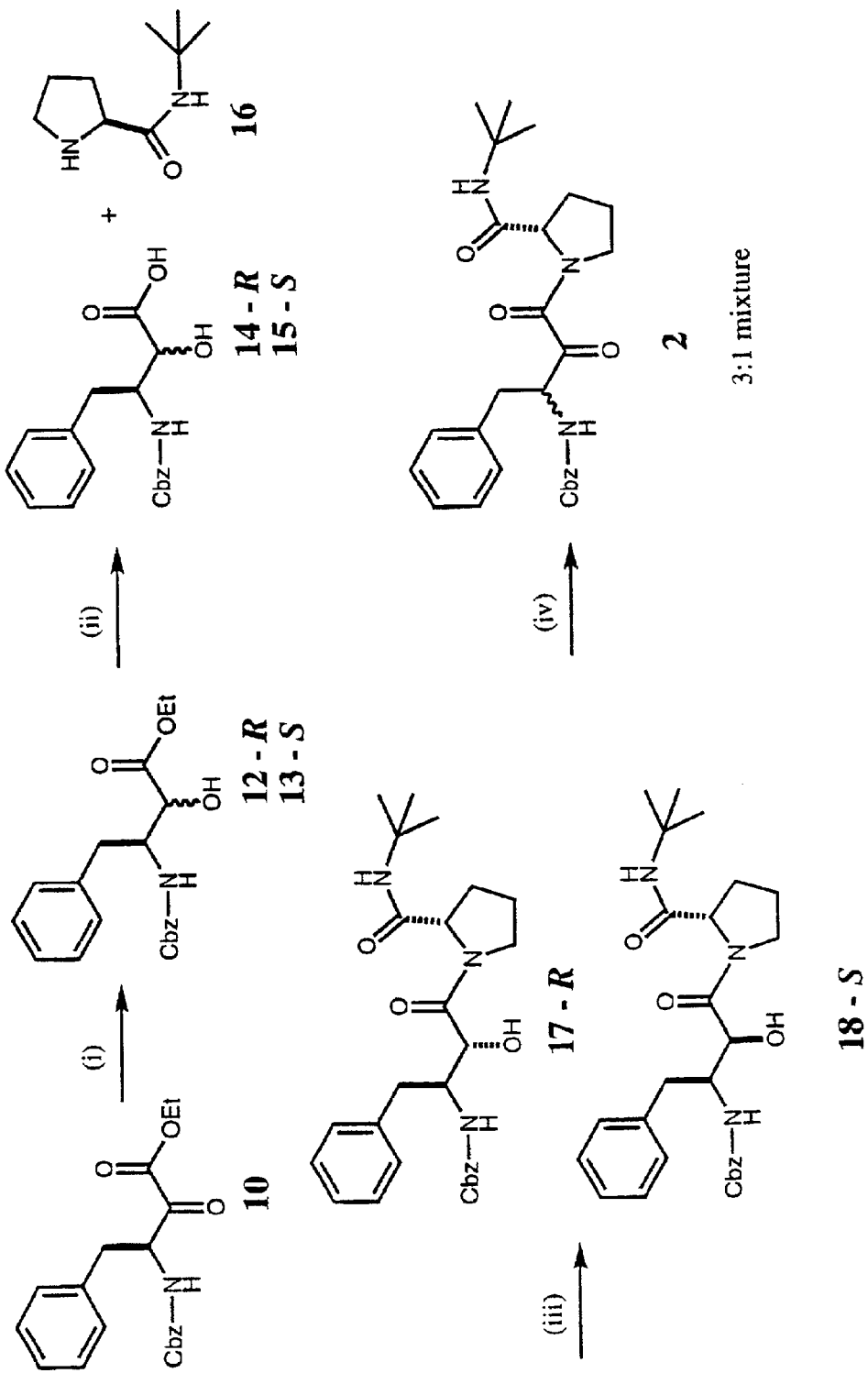
FIG. 7 illustrates the synthesis of compound 2. The steps indicated are as follows: (i) NaBH$_4$, MeOH, 0° C., 95%; (ii) 0.17 N LIOH, MeOH/H$_2$O, 2:1, 98%; (iii) EDC, HOBT, DIEA, DMF/CH$_3$CN, (1:1), 84%; (iv) Dess-Martin periodinane, CH$_2$Cl$_2$, 95%.

As seen in the electron density map, the inhibitor is bound in the active site of HIV-PR in its hydrated state (FIG. 7). One of the two hydroxyls is located between two aspartates, making hydrogen bonds with both of them, while the other hydroxyl interacts with only one aspartate. The keto group is also hydrogen bonded to a catalytic aspartate. The phenylalanine and proline side chains occupy proper $S_1$ and $S_1'$ pockets making interactions similar to those observed in other structures. The carboxybenzyl group on the N-terminus and the tert-butyl group of the tert-butyl amide on the C-terminus of the inhibitor are roughly in the $S_2$ and $S_2'$ pockets, respectively. The conserved water (Wat-301), which is forming hydrogen bonds between the inhibitor and the two flaps of the enzyme, is clearly observed. Its location is rather asymmetric, unlike the case of the majority of other inhibitor complexes. The distance between the carbonyl oxygen which mimics the $P_2$ CO group and Wat-301 is 2.5 Å, while the distance to the $P_1'CO$ is 3.2 Å.

Remarkable similarity is observed in the binding mode of the central and C-terminal parts of compound 2, and the similar parts of an inhibitor KNI-272. The differences in their binding constants are very significant ($K_1$ for KNI-272 is almost five orders of magnitude lower than for 2), despite the presence of an extra hydrogen bond in the central part of the complex of HIV PR and compound 2. Thus the increase in the potency of KNI-272 must be due to the elongation of its N-terminus, which has a bulky 5-isoquinolyloxyacetyl (IQoa) moiety. The regions of the protein interacting with this group, including the Phe-53 in one monomer and Pro-81 in another shift significantly towards the inhibitor, making extensive hydrophobic contacts with the IQoa group.

When the α-keto amide 2 was tested against FIV PR, it was found to have no inhibitory effect when added in concentrations up to 70 mM. This result was surprising due to the similarity between the natural substrates for HIV and FIV proteases bordering the matrix/capsid cleavage site as illustrated earlier. It appears that FIV PR may require additional specific residues between the $P_4$–$P_4'$ sites, than HIV PR, before it is able to recognize the core isostere 2 as a substrate. This is also supported by the observation that HIV PR will cleave an Acetyl-(6 residue) peptide substrate of sequence Gln-Ala-Tyr-Pro-Ile-Gln whereas the smallest peptide FIV PR is known to cleave is an acetyl-(8 residue) peptide of sequence Pro-Gln-Ala-Tyr-Pro-Ile-Gln-Thr. The corresponding protected dipeptide (Cbz-Phe-Pro-NBu$^t$) was not cleaved by HIV or FIV proteases under normal assay conditions.

In an effort to develop inhibitors of the FIV PR, it was found that the addition of suitable residues to interact with just the $P_2'$ and $P_3'$ sites of FIV PR was sufficient for moderate inhibition. Coupling of a side chain specific for FIV PR to the C-terminus of 2 gave 4 (FIG. 6). This extended isostere 4 was found to have an $IC_{50}$ of 251M and a Ki of 29 μM against FIV PR and the activity against HIV PR was slightly enhanced ($K_i$ of 154 nM). It appears that the isosteric core structure of HIV PR inhibitors do not bind tightly to the FIV PR, and additional complementary groups are needed to enhance the binding. This difference is also observed in the analysis of other known HIV PR inhibitors. The potent cyclic urea based HIV PR inhibitor DMP 323 ($IC_{50}$, =36 nM, $K_{i=}$0.27 nM) for example was also found to be a very poor inhibitor of FIV PR ($IC_{50}$=7.3 mM).

When the activity of the monomethylated derivative 7 is compared to that of the dimethylated derivative 5, it can be seen that a hydrophobic moiety at the C-5 position decreases the potency of the isostere, whereas the activity increases when similar hydrophobic substitutions are made at the C-3 and C-4 positions as in compound 6. The permethylated pyrrolidine derivative 6 was the most potent derivative of the series 5–7, but significant activity was lost due to the absence of the amide bond at C-1, as can be seen by comparison of the activity of the methylated derivatives 5–7 to that of compound B. The C-4 substituted pyrrolidine derivatives 9–11 were shown to be more potent than 8, with the trans-C-4 methoxy derivative 10 being the best ($IC_{50}$= 2.9 μM).

The permethylated α-keto amide derivative 12 (FIG. 10) was synthesized for comparison and was found to be more potent than the corresponding hydroxyethylamine isostere 6 but significantly less potent ($K_i$=20 μM) than the original isostere 2 against HIV PR. This result again illustrates the importance of an amide bond at C-1 of the pyrrolidine derivative.

In summary, a new class of mechanism based inhibitors of the HIV and FIV proteases with pyrrolidine-containing α-keto amide and hydroxyethylamine core structures is disclosed. These α-keto amide core structure 2 are disclosed to be approximately 300-fold better than the corresponding hydroxyethylamine isosteric structure and 1300-fold better than the corresponding phosphinic acid derivative as an inhibitor of the HIV protease. The α-keto amide is however not hydrated until it is bound to the HIV protease as indicated by the NMR study and the X-ray structural analysis. Further analysis of the inhibition activities of hydroxyethylamine isosteres containing modified pyrrolidine derivatives disclosed that a cis-methoxy group at C-4 of the pyrrolidine improved the binding 5-fold and 25-fold for the trans-isomer. When this strategy was applied to the α-keto amide isostere, a cis-benzyl ether at C-4 was found to enhance binding 3-fold. Of the core structures prepared as inhibitors of the HIV protease, none show significant inhibitory activity against the mechanistically identical FIV protease, and additional complementary groups are needed to improve inhibition.

Figure 11:
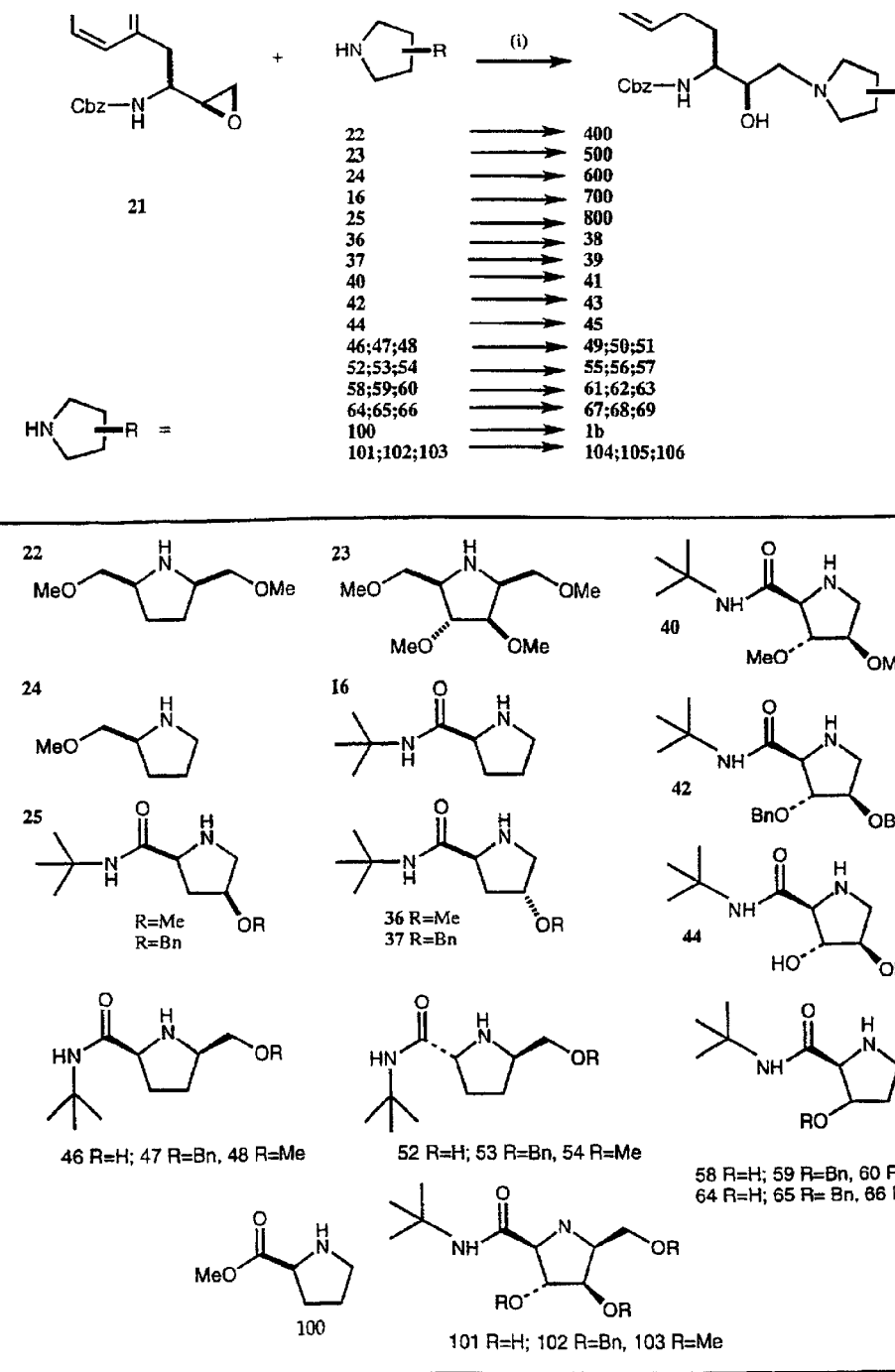
FIG. 11 illustrates a general coupling procedure to form hydroxyethyl amine compounds starting from epoxide 21 and using the indicated pyrolidines. The procedure is as follows: (i) Methanol, Et$_3$N, reflux, 24 hours, 40–60%.
Figure 12:
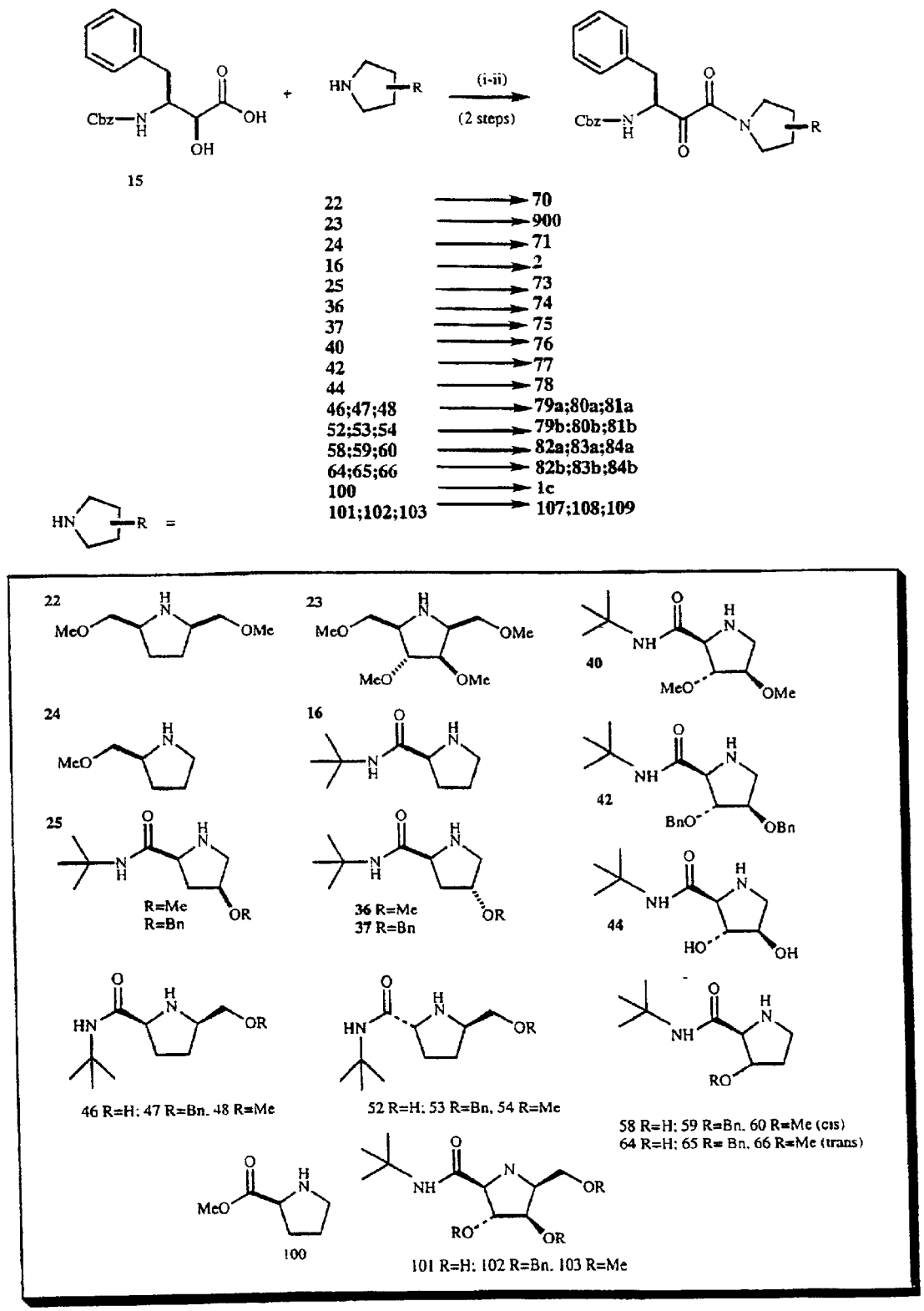
FIG. 12 illustrates a general coupling procedure to form α-ketoamide compounds starting from carboxyacid 15 and using the indicated pyrolidines. The two step procedure is as follows: (i) EDC, HOBT, DIEA, DMF/CH$_3$CN, (1:1); (ii) Dess-Martin periodinane oxidation, CH$_2$Cl$_2$, quantitative.

Another aspect of the invention is directed to the use of FIV PR as a model for the development of HIV PR inhibitors and for the study of drug resistance. This disclosure is supported by the data reported herein and by several additional observations. First, both enzymes are mechanistically identical. Second, structure-based alignment of the two enzymes displays their structure similarity (FIGS. 11 and 12). Third, most potent non-covalent inhibitors of the HIV PR are not good inhibitors of the FIV PR, whereas FIV PR inhibitors are often better HIV PR inhibitors. Therefore, good low molecular weight inhibitors of the FIV PR are disclosed to be better for the HIV PR. Fourth, the HIV PR isolated from the inhibitor-resistant mutants contains mutations that are found in the corresponding positions of the FIV PR. As shown in FIG. 12, the six highlights represent the changed amino acids found in the HIV PR isolated from mutants resistant to HIV PR inhibitors which are identical to those found in the FIV PR in the same position. Accordingly, FIV PR is disclosed to be a good model for the development of HIV PR inhibitors with less resistance problem. For example, the HIV PR isolated from a mutant resistant to a synthetic protease inhibitor contains the 150 V mutation, and the mutant protease is less inhibited by the same inhibitor by 80-fold.

Table I. Inhibition activities against HIV and/or FIV PR. The inhibitory activities of various isosteres against the HIV and/or FIV PR illustrating a dual screening method against these related viral proteases are illustrated in Table I provided below:

TABLE I

Inhibition activities against HIV and/or FIV PR.

| Compound | HIV PR | | FIV PR | |
|---|---|---|---|---|
| | $IC_{50}$ | $K_i$ | $IC_{50}$ | $K_i$ |
| 1 | 6 μM | 6 μM | — | — |
| 2 | 700 nM | 214 nM | >70 mM | — |
| 2a | 1.57 μM | 220 nM | | |
| 2b | 1.9 μM | 318 nM | | |
| 2c | 460 nM | 65 nM | | |
| 3 | 3.18 μM | 405 nM | — | — |
| 4 | — | 154 nM | 25 μM | 29 μM |
| 5 | 1.8 mM | — | — | — |
| 6 | 100 μM | — | — | — |
| 7 | 1.6 mM | — | — | — |
| 8 | 60 μM | — | — | — |
| 9 | 17 μM | — | — | — |
| 10 | 2.9 μM | — | — | — |
| 11 | 3.9 μM | — | — | — |
| 12 | 20 μM | — | — | — |

Synthetic Methods
1) Biological Assays

For determination of $IC_{50}$ values for HIV protease, a backbone engineered HIV-1 protease, prepared by total chemical synthesis (Kent et. al. Science 1992, 256, 221) 450 nM final concentration was added to a solution (152 $\mu$L final volume) containing inhibitor, 28 $\mu$M fluorogenic peptide substrate (sequence Abz-Thr-Ile-Nle-Phe-(p-NO$_2$)-Gln-Arg-NH$_2$ (Toth et. al., Int. J. Peptide Res. 1990, 36, 544)) and 1.8% dimethylsulfoxide in assay buffer: 100 mM MES buffer containing 0.5 mg/mL BSA (Bovine Serum Album, fatty acid, nuclease and protease free—to stabilize enzyme) at pH 5.5. The solution was mixed and incubated over 5 minutes during which time the rate of substrate cleavage was monitored by continuously recording the change in fluorescence of the assay solution. An excitation filter of 325 nm, and an emission filter of 420 nm were used. This data was converted into $\mu$M substrate cleaved per minute, using a predetermined standard calibration curve of change in fluorescence against concentration of substrate cleaved.

Determination of $K_i$ for HIV protease was performed similarly with the following modifications. The substrate concentrations used were 57, 43, 28 and 14 $\mu$M. All other concentrations were as above. The curve fit for the data was determined and the subsequent $K_i$ derived using a computer program based on the equation of Morrison et. al. BioChim. Biophys. ACTA 1969, 185, 269, for tight binding inhibitors.

For determination of $K_1$ and IC$_{50}$ for FIV protease, 0.125 $\mu$g of the enzyme was added to a solution (100 $\mu$L final volume) containing inhibitor, 560 $\mu$M peptide substrate (sequence Gly-Lys-Glu-Glu-Gly-Pro-Pro-Gln-Ala-Tyr-Pro-Ile-Gln-Thr-Val-Asn-Gly) and 2% dimethyl sulfoxide in a 1:3 mixture of assay buffer (as above) and 4M NaCl$_{aq}$. solution. The solution was mixed and incubated for 10 minutes at 37° C. and the reaction quenched by addition of 8 M guanidine HCl solution containing 0.2 M sodium acetate at pH 4.2 (100 $\mu$L). The cleavage products and substrate were separated by reverse phase HPLC. Absorbance was measured at 215 nm, peak areas were determined and percent conversion to product was calculated using relative peak areas. The data were plotted as 1/V (V=rate substrate is cleaved in nmol/min) against inhibitor concentration and the—$K_i$ determined as the point at which the resulting line intersects with 1/V$_{max}$ (V$_{max}$=6.85 nmol/min). IC$_{50}$ was determined as the inhibitor concentration at 50% inhibition. V$_{max}$ (6.85±0.7 nmol min$^{-1}$) and K$_m$ (707±70 $\mu$M) for FIV protease were determined from a plot of 1/V (V=rate in nmol/min) against 1/[S] ([S]=substrate concentration in nmol). The data used was generated similarly to that for $K_i$ with the following modifications. The substrate concentrations used were 560, 448, 336, 224, 111 and 56 $\mu$M, in the absence of inhibitor.

Purification of FIV protease: A 503 base pair Eco Rl-Bam Hl fragment containing the coding sequence of FIV protease was cloned from FIV-34TF10 (Talbott et. al. Proc. Natl. Acad. Sci. USA 86 1989, 5743) into the pT7-7 vector (Tabor et. al. Proc. Natl. Acad. Sci USA 82 1985, 1074). The 5' end of the insert was modified by the addition of an Ndel adaptor, which provided the proper reading frame with initiation of translation from the methionine encoded in the latter site. Translation resulted in production of an 18.6 kDa precursor, which auto-processed to a 13.2 kDa FIV PR plus N- and C-terminal fragments of 3.6 kDa and 1.8 kDa, respectively. The construct was transformed into E. coli strain BL21.DE3, lys S (Studier et. al. Meth. Enzymol. 1990, 185, 60) and overnight cultures were used to inoculate 15 liter fermentations, performed using Circlegrow medium (Bio 101) plus 100 $\mu$L ampicillin, 20 $\mu$M chloramphenicol, at 37° C. The cells were allowed to reach mid-log phase, then the temperature was reduced to 24° C. and IPTG (isopropylB-thiogalactopyranoside) was added to a final concentration of 1 mM. The fermentation was allowed to proceed for 16 hours, at which time the cells were harvested by centrifugation and frozen at -70° C. in 100 g aliquots for future use.

Cells (100 g) were lysed by addition of 600 mL, 50 mM Tris-HCl, pH 8, 5 mM EDTA and 2 mM 2-mercaptoethanol to the frozen pellet. The cells lysed upon thawing and the viscous mixture was homogenized at 4° C. for 2 min in a Waring blender. The sample was centrifuged at 8,000×g for 20 min and the pellet discarded. The sample was diluted to 1 liter, then subjected to tangential flow against a 300 K cut-off membrane (Filtron) and the PR was washed through the membrane using five liters of the same buffer. The retentate was discarded and the flow-through supernatant concentrated by tangential flow against a 10 K cut-off membrane. The retentate was passed over a DE52 anion exchange column (5×20 cm) equilibrated in the same buffer. The flow-through from this column was passed over an S-Sepharose Fast Flow matrix (2.5×20 cm column, Pharmacia), again equilibrated at pH 8 in the same buffer. The flow-through from S-Sepharose was made 1M with respect to ammonium sulfate and applied to a phenyl sepharose column (Pharmacia, 1.5×10 cm), washed with lysis buffer containing 1M ammonium sulfate, then eluted with a 100–0% linear ammonium sulfate gradient. Peak fractions containing PR were pooled, concentrated using Centripreps (Amicon), and dialyzed against 10 mM Tris-HCl, pH 8, 5 mM EDTA, 2 mM 2-mercaptoethanol. The sample was made 10 mM with respect to MOPS, adjusted to pH 5.5 with HCl, then applied to a Resource S column (Pharmacia) equilibrated in 10 mM Tris-MOPS, pH 5.5, 5 mM EDTA and 2 mM 2-mercaptoethanol. PR was eluted using a linear 0–300 mM NaCl gradient in the same buffer. Peak fractions were pooled, concentrated, and stored as aliquots at -20° C. for further studies. The integrity of the isolated FIV PR was confirmed by ion spray mass spectrometry.

2) Chemical Synthesis

All manipulations were conducted under an inert atmosphere (argon or nitrogen). All solvents were reagent grade. Anhydrous ether, tetrahydrofuran (THF), and toluene were distilled from sodium and/or benzophenone ketyl. Dichloromethane (CH$_2$Cl$_2$) was distilled from calcium hydride (CaH$_2$). N,N, Dimethylformamide (DMF) and acetonitrile were distilled from phosphorous pentoxide and calcium hydride. Methanol was distilled from magnesium and iodine. Organic acids and bases were reagent grade. All other reagents were commercial compounds of the highest purity available. Analytical thin-layer chromatography (TLC) was performed on Merck silica gel (60 F-254) plates (0.25 mm). Visualization was effected using standard procedures unless otherwise stated. Flash column chromatography was carried out on Merck silica gel 60 particle size (0.040–0.063 mm, 230–400 Mesh). Melting points were determined with a Thomas-Hoover capillary melting point apparatus and are uncorrected. Proton and carbon magnetic resonance spectra ($^1$H-NMR, $^{13}$C-NMR) were recorded on either a Bruker AM-500, AMX-400 or AC250 MHz Fourier transform spectrometer. Coupling constants (J) are reported in hertz and chemical shifts are reported in parts per million ($\delta$) relative to tetramethylsilane (TMS, 0 ppm), MeOH (3.30 ppm for $^1$H and 49.0 ppm for $^{13}$C) or CHCl$_3$ (7.24 ppm for $^1$H and 77.0 ppm for $^{13}$C) as internal reference. Infrared spectra (IR) were recorded on a Perkin-Elmer 1600 series FT-IR spectrophotometer. Absorptions are reported in wavenumbers (cm$^{-1}$).

Peptide fragments described herein were synthesized using traditional peptide coupling methodologies [EDC (1-

(3-dimethylaminopropyl)-3-ethylcarbodiimide HCl), HOBt (1-hydroxybenzotriazole) and DIEA (diisopropylethylamine)). Esters were hydrolyzed either by base (LiOH for methyl esters) or acid (TFA for t-butyl esters).

Synthesis of Compound 10 as Illustrated in FIG. 6

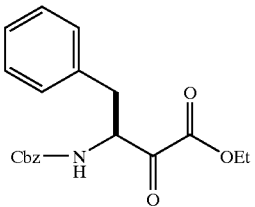

Figure 1:
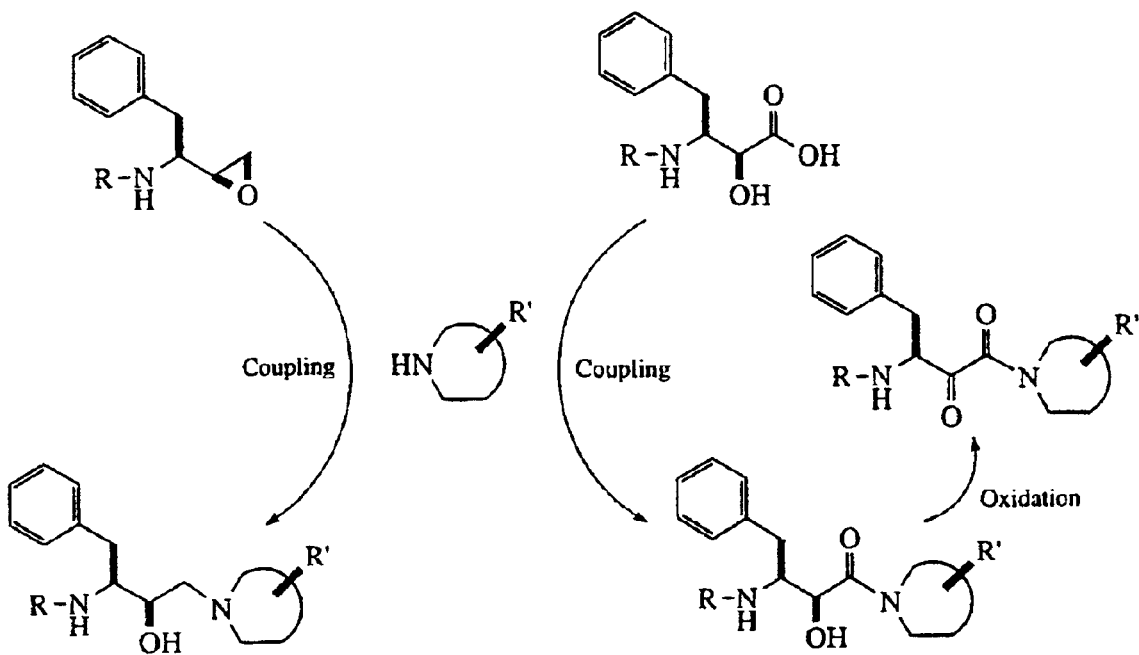
FIG. 1 illustrates an approach to rapidly access a number of potential inhibitors of HIV and/or FIV proteases to determine the protecting group and ideal substitution pattern of the 'proline' moiety to provide maximum inhibition of the enzymes.
Figure 2:
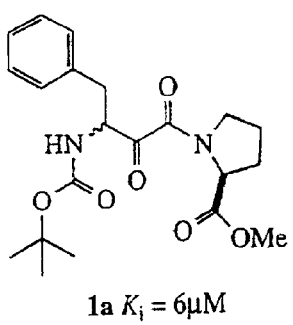
FIG. 2 illustrates a comparison of the α keto amide core structure to other isosteric structures. Compound activities are indicated.
Figure 2:
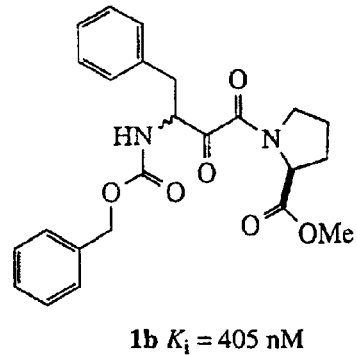
Figure 2:
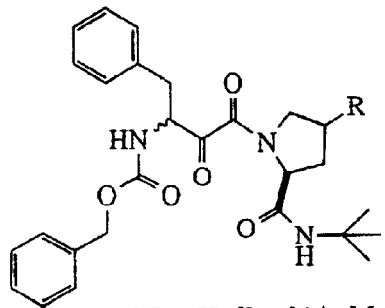
Figure 2:
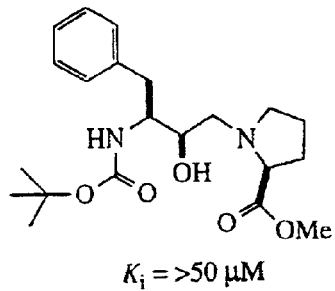
Figure 2:
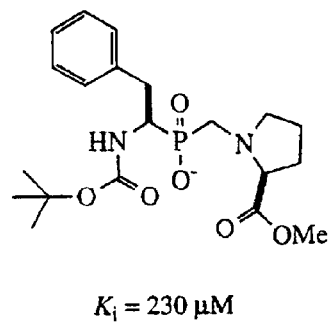

Compound 10: The α-keto ester 10 was synthesized according to the method described by Angelastro et al. *J. Org. Chem.* 1989, 54, 3913–3916. It is possible to synthesize α-keto esters via other methodologies, Wasserman, et al. *J. Org. Chem.* 1994, 59, 4364–4366(43); Wong et al. *J. Med. Chem* 1993, 36, 211–220, but the route employed was found to be most concise and high yielding. The methodology, shown in FIG. 1 and described by Angelastro, is as follows (i) t-BuLi, ethyl vinyl ether, $MgBr_2$, THF; (ii) $O_3$, $CH_2Cl_2$.

Synthesis of compound 11 as illustrated in FIG. 6, step (iii)

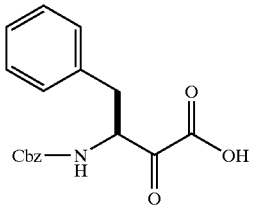

Compound 11. To a 2:1 solution of compound 10 in methanol/water (0.10 Molar) is added a 0.17 Normal solution of LiOH in water and the reaction is allowed to stir at 0° C. for 2 hours. The mixture is then purified by reverse phase chromatography and yielded compound 11 in 98% overall yield.

Synthesis of (2R, 3S) and (2S, 3S) N-(Benzylcxycarbonyl)-AHAP-(3-Amino-2-Hydroxy-4-Phenylbutanoic Acid) Ethyl Ester 12 and 13 as Shown in FIG. 7.

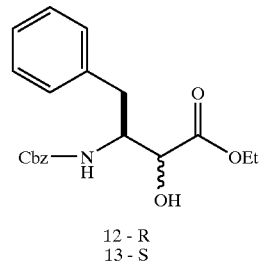

12 - R
13 - S

As illustrated in FIG. 7, step i, the substrate 10 (600 mg, 1.7 mmol) was dissolved in methanol (10 mL) and cooled to 0° C. Sodium Borohydride (70.3 mg, 1.9 mmol) was then added. After 20 minutes the reaction was quenched by addition of saturated ammonium chloride$_{(eq)}$ (10 mL). The reaction mixture was concentrated in vacuo to remove most of the methanol. The aqueous residue was then extracted with ethyl acetate (3×20 mL), washed with brine (10 mL), dried ($MgSO_4$) and concentrated in vacuo to give the crude product as a mixture of diastereomer. The alcohols were separated by flash chromatography eluting with 15% ethyl acetate in hexane to give the alcohols in a ratio of 3:4, 12 & 13 (590 mg, 97%). $R_f$=0.54 and 0.40 respectively (EtOAc/Hexane, 1:2): 12 (2R, 3S-colorless oil); $^1$H NMR (500 MHz, $CDCl_3$) δ 7.34–7.18 (10 H, m), 5.17 (1H, d, J 9.5), 5.04 (2H, s), 4.43–4.38 (1H, m), 4.33 (1H, dd, J 4.5, 2.0), 4.15–4.08 (1H, m), 3.98–3.92 (1H, m), 3.28 (1H, d, J 5.0); IR (NaCl) max 3368, 3030, 2981, 1731, 1520, 1455, 1246, 1104, 1055, 748, 699 cm; FABHRMS (NBA) m/e 358.1659 ([M+H]$^+$, $C_{20}H_{23}NO_5$ requires 358.1654); (Found: C, 67.30; H, 6.50; N, 3.99. $C_{20}H_{23}NO_5$ requires C, 67.21; H, 6.49; N, 3.92%). 13 (2S, 3S-crystalline); $^1$H NMR (500 MHz, $CDCl_3$) δ 7.34–7.18 (10H, m), 5.17 (1H, d, J 9.5), 5.04 (2H, s), 4.43–4.38 (1H, m), 4.33 (1H, dd, J 4.5, 2.0), 4.15–4.08 (1H, m), 3.98–3.92 (1H, m), 3.28 (1H, d, J 5.0); IR (NaCl) $v_{mas}$ 3368, 3030, 2980, 1731, 1520, 1455, 1246, 1104, 1055, 748, 699 $cm^{-1}$; FABHRMS (NBA) m/e 358.1661 (($M^+$+H), $C_{20}H_{23}NO_5$ requires 358.1654); (Found: C, 67.22; H, 6.57; N, 3.90. $C_{20}H_{23}NO_5$ requires C, 67.21; H, 6.49; N, 3.92%). m.p. 88–89° C.

Synthesis of (2R, 3S) and (2S, 3S)N-(Benzyloxycarbonyl)-3-Amino-2-Hydroxy-4-Phenylbutanoic Acid 14 & 15 Respectively as Illustrated in FIG. 7

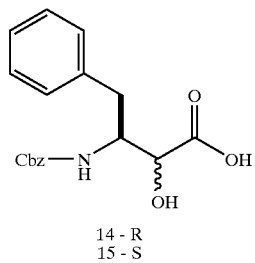

14 - R
15 - S

As illustrated in FIG. 7, step ii, the substrate (12 or 13) (250 mg, 0.70 mmol) was dissolved in 0.25 N LiOH in methanol/water, 2:1 (5 mL), and stirred at ambient temperature for 30 minutes. The pH of the reaction was adjusted to pH 7.0 with 1N HCl $_{(aq.)}$ and the methanol removed in vacua. The aqueous residue was then acidified to pH 2.0 with 1N HCl $_{(aq.)}$ and extracted with ethyl acetate (3×30 mL). The combined organic extracts were washed with water (10 mL), brine (10 mL) and dried ($MgSO_4$) before concentration in vacuo to give the desired acid (14 or 15) as a white solid (212 mg, 92%). The acids were purified by recrystallization from hot ethanol. 14 (2R, 3S); $^1$H NMR (500 MHz, $CD_3OD$) δ 7.31–7.18 (10H, m), 6.87 (1H, d, J 9.5), 5.00 (1H, d, J 10.0), 4.96 (1H, d, J 10.0), 4.31–4.23 (1H, m), 4.07 (1H, d, J 2.5), 2.93 (1H, dd, J 13.5, 7.5), 2.83 (1H, dd, J 13.5, 8.0); $^{13}$C NMR (125 MHz, $CD_3OD$) δ 176.6 (C=O), 158.5 (C=O), 139.8 (C), 138.5 (C), 130.7 (2×CH), 129.8 (2×CH), 129.7 (2×CH), 129.7 (CH), 129.1 (CH), 128.8 (CH), 127.8 (CH), 67.6 (CH), 57.1 ($CH_2$), 57.0 ($CH_2$), 39.3 (CH); FABHRMS (NBA) m/e 330.1353 ([M+H]$^+$, $C_{18}H_{19}NO_5$ requires 330.1341); m.p. 209–210 (decomp.). 15 (2S, 3S); $^1$H NMR (500 MHz, $CD_3OD$) δ7.28–7.18 (10H, m), 7.09 (1H, d, J 12.5), 4.97 (1H, d, J 12.5), 4.92 (1H, d, J 12.5), 4.26 (1H, d, J 4.0), 4.25–4.20 (1H, m), 2.81 (1H, dd, J 14.0, 4.0), 2.76 (1H, dd, J 14.0, 4.0); $^{13}$C NMR (125 MHz, $CD_3OD$) δ 175.9 (C=O), 158.5 (C=o), 140.0 (C), 138.6 (C), 130.6 (3×CH), 129.6 (CH), 129.5 (3×CH), 129.0 (CH), 128.8 (CH), 127.6 (CH), 74.3 (CH), 67.4 ($CH_2$), 57.1 (CH), 36.5 ($CH_2$); FABHRMS (NBA/NaI) m/e 352.1174 ([M+

Na]⁺, $C_{18}H_{19}NO_5$ requires 352.1161); (Found: C, 65.34; H, 5.75; N, 4.33. $C_{18}H_{19}NO_5$ requires C, 65.64; H, 5.82; N, 4.25%); m.p. 173–174° C. (decomp.).

Synthesis of L-Prolyl-tert-butyl amide 16 (scheme 7)

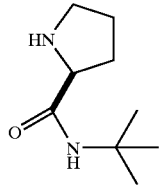

16

The substrate N-tert-Butoxycarbonyl-L-proline commercially available from Sigma, (3.0 g, 13.9 mmol), was dissolved in dry $CH_2Cl_2$ (20 mL). HOBT, 1-hydroxybenzotriazole hydrate (2.07 g, 15.3 mmol), EDC, 1-(3-dimethylaminopropyl)-3-ethylcarbodiimide, (2.93 g, 15.3 mmol), and tert-butylamine (1.6 mL, 15.3 mmol), were added and the mixture stirred for 18 hours at ambient temperature. The reaction was diluted with ethyl acetate (100 mL), and washed with water (2×20 mL), 1 N HCl $_{(aq.)}$ (10 mL) saturated sodium bicarbonate solution $_{(aq.)}$ (10 mL), water (10 mL), brine (10 mL) and dried ($MgSO_4$) before concentration in vacuo to give the crude product. Purification by flash chromatography, eluting with 33% EtOAc in Hexane gave N-tert-butoxycarbonyl-L-prolyl-tert-butyl amide as a colorless oil (1.53 mg, 40%). $R_f$=0.46 (EtOAc/Hexane, 1:1). ¹H NMR signals broadened due to rotamers: ¹H NMR (500 MHZ, $CDCl_3$) δ 7.31–7.25 (5H, m), 6.35 (1H, br s), 4.60–4.15 (3H, m), 3.55–3.22 (2H, m), 2.41–1.70 (4H, m), 1.60–1.18 (9H, br s); IR (NaCl) $v_{max}$ 3298, 3086, 2976, 1698, 1660, 1531, 1398, 1162 cm⁻¹; FABHRMS (NBA/NaI) m/e 293.1832 ([M+Na]⁺, $C_{14}H_{26}N_2O_3$ requires 293.1841). The N-tert-Butoxycarbonyl-L-prolyl-tert-butyl amide was carried on as follows:

N-tert-Butoxycarbonyl-L-prolyl-tert-butyl amide (600 mg, 2.22 mmol) was dissolved in $CH_2Cl_2$ (10 mL) and cooled to 0° C. TFA, trifluoroacetic acid, (10 mL) was then added to the solution. After 1 hour at 0° C. the reaction was concentrated in vacuo (any remaining TFA was removed under high vacuum) to give the trifluoroacetic acid salt of the desired amine 16 as a colorless oil (800 mg, 95%). The amine was used without further purification in subsequent coupling steps. ¹H NMR (500 MHz, $CDCl_3$) δ 7.30 (1H, br s), 6.90 (1H, br s), 4.52 (1H, br s), 3.35 (2H, br s), 2.49–2.34 (1H, m), 2.08–1.97 (3H, m), 1.34 (9H, s); ¹³C NMR (125 MHz, $CDCl_3$) δ 167.4 (C=O), 59.6 (CH), 52.3 (C), 46.6 ($CH_2$), 30.4 ($CH_2$), 28.2 (3×$CH_3$), 24.6 ($CH_2$); FABHRMS (NBA) m/e 171.1500 ([M+H]⁺, $C_9H_{18}N_2O$ requires 171.1497).

General Peptide Coupling Procedure as Illustrated in FIG. 7: Synthesis of (2S, 3R) and (2S, 3S) 3-(N-Benzyloxycarbonyl)amino-2-hydroxy-4-phenylbutyryl-L-prolyl-tert-butyl Amide 17 and 18.

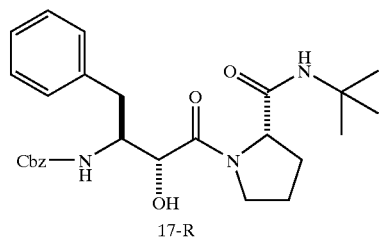

17-R

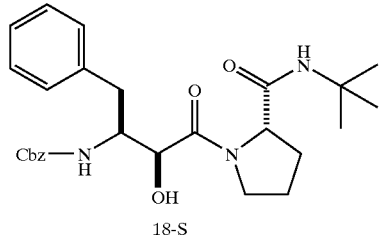

18-S

As illustrated in FIG. 7, step iii, the substrate 14 or 15 (70 mg, 0.213 mmol), was dissolved in dry DMF (3 mL). HOBT, 1-hydroxybenzotriazole hydrate (31 mg, 0.22 mmol), EDC, 1-(3-dimethylaminopropyl)-3-ethylcarbodiimide, (43 mg, 0.224 mmol), DIEA, diisopropylethylamine, (122 μl, 0.703 mmol) were added and the mixture stirred for 30 minutes at room temperature. The secondary amine 16 as its TFA salt (73 mg, 0.255 mmol) was added and the reaction stirred for 18 hours. The reaction mixture was diluted with ethyl acetate (20 mL) and added to saturated ammonium chloride (30 mL). The aqueous phase was extracted with ethyl acetate (3×10 mL). The combined organic phases were then washed with water (2×5 mL), 1 N HCl $_{(aq.)}$ (5 mL), saturated sodium bicarbonate solution $_{(aq.)}$ (50 mL), water (5 mL), brine (5 mL) and dried ($MgSO_4$) before concentration in vacuo to give the crude product. Flash chromatography eluting with ethyl acetate/hexane, 1:1 to give the desired coupled product 17 or 18 as a colorless oil (74 mg, 72%). $R_f$=0.33 and 0.28 respectively (EtOAc:Hexane, 1:1). 17 (2R, 3S); ¹H NMR (500 MHz, $CDCl_3$) δ 7.37–7.23 (10H, m), 6.44 (1H, s), 5.16 (1H, d, J 9.5), 5.03 (2H, s), 4.24–4.18 (1H, m), 4.11 (1H, d, J 5.5), 3.97–3.90 (2H, m), 3.28–3.23 (1H, m), 3.12–3.06 (1H, m), 2.99–2.90 (2H, m), 2.18–2.12 (1H, m), 2.01–1.96 (1H, m), 1.89–1.83 (1H, m), 1.83–1.76 (1H, m), 1.27 (9H, s); ¹³C NMR (100 MHz, $CDCl_3$) δ 171.4 (C=O), 169.9 (C=O), 156.0 (C=O), 137.4 (C), 136.7 (C), 129.2 (2×CH), 128.7 (2×CH), 128.4 (2×CH), 128.0 (CH), 127.9 (2×CH), 126.9 (CH), 68.6 (CH), 66.7 ($CH_2$), 61.7 (CH), 52.8 (CH), 51.1 (C), 46.1 ($CH_2$), 38.4 ($CH_2$), 28.6 (3×$CH_3$), 27.4 ($CH_2$), 24.7 ($CH_2$); IR (NaCl) $v_{max}$ 3318, 2966, 1714, 1667, 1537, 1454, 1366, 1041 cm⁻¹; FABHRMS (NBA) m/e 482.2677 ([M+H]⁺, $C_{27}H_{35}N_3O_5$ requires 482.2655); (Found: C, 67.22; H, 7.32; N, 8.80. $C_{27}H_{35}N_3O_5$ requires C, 67.34; H, 7.33; N, 8.73%). 19 (2S, 3S); (major rotamer only) ¹H NMR (400 MHz, $CDCl_3$) δ7.33–7.17 (10H, m), 6.45 (1H, s), 5.21 (1H, d, J 8.8), 4.99 (2H, s), 4.60 (1H, dd, J 6.8, 2.1), 4.52–4.47 (1H, m), 4.21–4.13 (1H, m), 3.81–3.66 (3H, m), 2.75–2.60 (2H, m), 2.41–2.30 (1H, m), 2.25–2.09 (1H, m), 2.05–1.90 (2H, m), 1.30 (9H, s); ¹³C NMR (100 MHz, $CDCl_3$) δ 171.3 (C=O), 169.6 (C=O), 156.0 (C=O), 137.3 (2×C), 129.1 (2×CH), 128.5 (2×CH), 128.4 (2×CH), 128.0 (CH), 127.8 (2×CH), 126.5 (CH), 71.3 (CH), 66.6 ($CH_2$), 61.1 (CH), 54.3 (CH), 51.3 (C), 47.5 ($CH_2$), 33.8 ($CH_2$), 28.6 (3×$CH_3$), 26.9 ($CH_2$), 25.4 ($CH_2$); IR (NaCl) $v_{max}$ 3318, 2966, 1714, 1667, 1537, 1454, 1366, 1041 cm⁻¹; FABHRMS (NBA/CsI) m/e 614.1645 ([M+Cs]⁺, $C_{27}H_{35}N_3O_5$ requires 614.1631); (Found: C, 67.20; H, 7.66; N, 8.54. $C_{27}H_{35}N_3O_5$ requires C, 67.34; H, 7.33; N, 8.73%).

General Dess-Martin Oxidation Procedure as Illustrated in FIG. 7:
Synthesis of (3S) and (3R) 3-(N-Benzyloxycarbonyl)amino-2-keto-4-phenylbutyryl-L-prolyl-tert-butyl Amide 2.

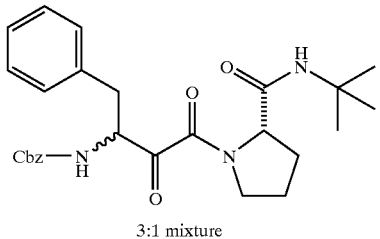

3:1 mixture

As illustrated in FIG. 7, step iv, the substrate 17 (21 mg, 0.044 mmol) was dissolved in dry $CH_2Cl_2$ (2 mL), and Dess-Martin periodinane (26 mg, 0.088 mmol) added. The reaction mixture was stirred at ambient temperature for 24 hours, then diluted with ethyl acetate (10 mL) and quenched by addition of saturated sodium bicarbonate $_{(aq.)}$ (5 mL) and sodium thiosulfate. The aqueous phase was extracted with ethyl acetate (3×20 mL). The combined organic extracts washed with water (10 mL), brine (10 mL), dried ($MgSO_4$) and concentrated in vacuo to give the crude product. Flash chromatography eluting with 30% ethyl acetate in hexane gave the desired product 2 as a 3:1 mixture of diastereomers (colorless oil) (20 mg, 95%). $R_f$=0.47 (EtOAc/Hexane, 1:2). Spectral data on mixture: $^1$H NMR (400 MHz, DMSO) δ 7.86 (1H, d, J 7.8), 7.71 (1H, d, J 8.3), 7.64 (1H, s), 7.53 (1H, s), 7.37–7.10 (20H, m), 5.10 (1H, ddd, J 11.0, 8.3, 2.4), 5.01 (1H, d, J 12.6), 4.95 (1H, d, J 12.6), 4.95 (1H, d, J 16.3), 4.88 (1H, d, J 16.3), 4.79–4.73 (1H, m), 4.66 (1H, dd, J 7.8, 4.2), 4.26 (1H, dd, J 7.8, 4.5), 3.60–3.37 (3H, m), 3.33–3.24 (1H, m), 3.18 (1H, dd, J 14.7, 2.4), 3.13 (1H, dd, J 10.2, 3.9), 2.79 (1H, dd, J 13.7, 10.2), 2.46 (1H, dd, J 14.7, 11.0), 2.23–2.17 (1H, m), 2.04–1.97 (1H, m), 1.90–1.60 (6H, m), 1.24 (9H, s), 1.22 (9H, s); $^{13}$C NMR (100 MHz, $CDCl_3$) δ 198.91 (C=O), 196.7 (C=O), 170.7 (C=O), 169.9 (C=O), 162.6 (C=O), 162.2 (C=O), 156.1 (C=O), 155.9 (C=O), 138.5 (C), 137.6 (C), 136.9 (C), 136.9 (C), 129.0 (CH×2), 128.8 (CH×2), 128.4 (CH×8), 127.8 (CH×2), 127.6 (CH×2), 127.6 (CH×2), 126.5 (CH), 126.4 (CH), 65.6 ($CH_2$), 65.3 ($CH_2$), 60.3 (CH), 59.7 (CH), 59.2 (CH), 58.2 (CH), 50.3 (C), 50.1 (C), 47.6 ($CH_2$), 47.4 ($CH_2$), 34.8 ($CH_2$), 34.1 ($CH_2$), 32.5 ($CH_2$), 29.1 ($CH_2$), 28.5 ($CH_3$×3), 28.4 ($CH_3$×3), 24.5 ($CH_2$), 21.7 ($CH_2$); IR (NaCl) $v_{max}$ 3325, 2966, 1715, 1670, 1634, 1531, 1454, 1258, 1051, 738, 699; FABHRMS (NBA/NaI) m/e 502.2295 ([M+Na]$^+$, $C_{27}H_{33}N_3O_5$ requires 502.2318); (Found: C, 67.62; H, 7.05; N, 8.96. $C_{27}H_{33}N_3O_5$ requires C, 67.62; H. 6.94; N, 8.76%).

Figure 8:
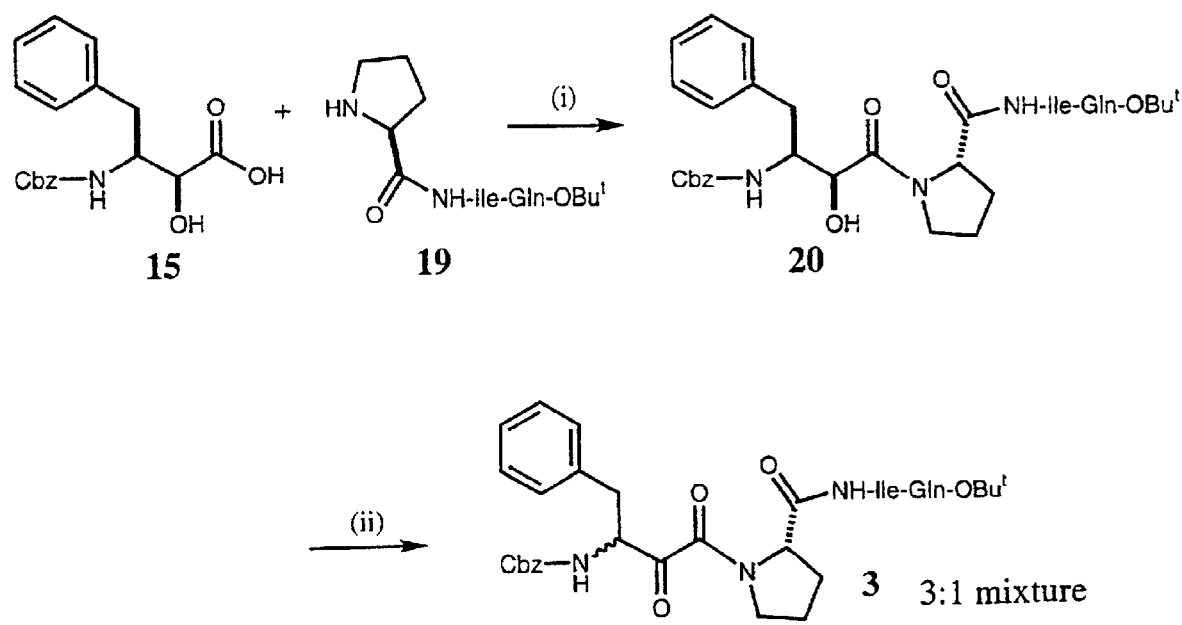
FIG. 8 illustrates the synthesis of compound 3. The steps are indicated as follows: (i) EDC, HOBT, DIEA, DMF/CH$_3$CN, (1:1), 80%; (ii) Dess-Martin periodinane, CH$_2$Cl$_2$, quantitative.

Synthesis of L-Prolyl-L-isoleucyl-L-glutamine-tert-butyl Amide 19 as Illustrated in FIG. 8

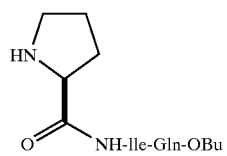

As illustrated in FIG. 8, the substrate N-tert-Butoxycarbonyl-L-proline commercially available from Sigma, (3.0 g, 13.9 mmol), was dissolved in dry $CH_2Cl_2$ (20 mL). HOBT, 1-hydroxybenzotriazole hydrate (2.07 g, 15.3 mmol), EDC, 1-(3-dimethylaminopropyl)-3-ethylcarbodiimide, (2.93 g, 15.3 mmol), and NH-Ile-Gln-OBu (1.6 mL, 15.3 mmol; peptide fragments were synthesized using traditional peptide coupling methodologies: EDC, HOBT, DIEA, ILe, Gln, and protected as a tertButyl-ester), were added and the mixture stirred for 18 hours at ambient temperature. The reaction was diluted with ethyl acetate (100 mL), and washed with water (2×20 mL), 1 N HCl $_{(aq.)}$ (10 mL), saturated sodium bicarbonate solution $_{(aq.)}$ (10 mL), water (10 mL), brine (10 mL) and dried ($MgSO_4$) before concentration in vacuo to give the crude product. Purification by flash chromatography, eluting with 33% EtOAc in Hexane gave NH-Ile-Gln-OBu-L-prolyl-tert-butyl amide 19 as a colorless oil (1.53 mg, 40%). $R_f$=0.46 (EtOAc/Hexane, 1:1). $^1$H NMR signals broadened due to rotamers: Spectral data: $^1$H NMR (400 MHz, $CD_3OD$) δ 4.35–4.30 (1H, m), 4.31 (1H, dd, J 9.3, 5.0), 4.21 (1H, d, J 7.8), 3.41–3.26 (2H, m), 2.48–2.36 (1H, m), 2.36–2.22 (2H, m), 2.20–1.79 (6H, m), 1.67–1.54 (1H, m), 1.46 (9H, s), 1.32–1.17 (1H, m), 0.99 (3H, d, J 6.8), 0.93 (3H, t, J 7.4); $C^{13}$ NMR (100 MHz, $CD_3OD$) δ 173.3 (C=O), 172.0 (C=O), 170.1 (C=O), 167.7 (C=O), 83.0 (C), 60.7 (CH), 59.9 (CH), 54.0 (CH), 47.4 ($CH_2$), 37.9 (CH), 32.5 ($CH_2$), 31.2 ($CH_2$), 28.4 ($CH_2$), 28.2 (3×$CH_3$), 26.0 ($CH_2$), 25.0 ($CH_2$), 15.9 ($CH_3$), 11.4 ($CH_3$); FABHRMS (NBA) m/e 435.2575 ([M+Na]$^+$, $C_{20}H_{36}N_4O_5$ requires 435.2583).

Synthesis of (2S, 3S) 3-(N-Benzyloxycarbonyl)amino-2-hydroxy-4-phenylbutyryl-L-prolyl-L-isoleucyl-L-glutamine-tert-butyl Amide 20 as Illustrated in FIG. 6

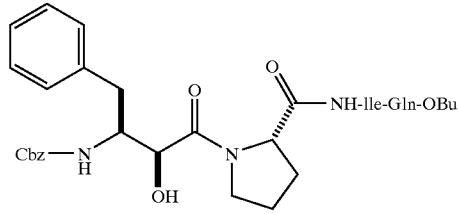

As illustrated in FIG. 8, step i, the coupling of the acid 15 to the amide 19 was carried out using the general peptide coupling procedure. A representative synthesis is as follows: the substrate 15 (70 mg, 0.213 mmol), was dissolved in dry DMF (3 mL). HOBT, 1-hydroxybenzotriazole hydrate (31 mg, 0.22 mmol), EDC, 1-(3-dimethylaminopropyl)-3-ethylcarbodiimide, (43 mg, 0.224 mmol), DIEA, diisopropylethylamine, (122 µl, 0.703 mmol) were added and the mixture stirred for 30 minutes at room temperature. The secondary amine 19 as its TFA salt (73 mg, 0.255 mmol) was added and the reaction stirred for 18 hours. The reaction mixture was diluted with ethyl acetate (20 mL) and added to saturated ammonium chloride (30 mL). The aqueous phase was extracted with ethyl acetate (3×10 mL). The combined organic phases were then washed with water (2×5 mL), 1 N HCl $_{(aq.)}$ (5 mL), saturated sodium bicarbonate solution $_{(aq.)}$ (50 mL), water (5 mL), brine (5 mL) and dried ($MgSO_4$) before concentration in vacuo to give the crude product. Flash chromatography eluting with ethyl acetate/hexane, 1:1 to give the desired coupled product 20 as a colorless oil (74 mg, 72%). $R_f$=0.33 and 0.28 respectively (EtOAc:Hexane, 1:1) Flash chromatography eluting with 5% methanol in dichloromethane gave the desired product 20 as a colorless oil. $^1$H NMR (400 MHz, $CDCl_3$) (major rotamer only) δ 7.42–7.12 (11H, m), 6.9.5 (1H, d, J 8.6), 6.79 (1H, s), 6.07 (1H, s), 5.95 (1H, d, J 8.3), 5.03 (1H, d, J 12.4), 4.96 (1H, d, J 12.4), 4.65 (1H, d, J 4.5), 4.51 (1H, dd, J 8.0, 5.2), 4.49–4.35 (2H, m), 4.32 (1H, d, J 7.8), 3.99–3.94 (1H, m), 3.70–3.50 (2H, m), 2.91–2.83 (2H, m), 2.28–2.21 (1H, m), 2.21–2.10 (3H, m), 2.02–1.75 (5H, m), 1.43 (9H, s), 1.14–1.06 (1H, m), 0.86 (3H, d, J 6.4), 0.78 (3H, t, J 7.6);

C[13] NMR (100 MHz, CDCl$_3$) δ 175.5 (C=O), 172.2 (C=O), 171.5 (2×C=O), 170.4 (C=O), 156.3 (C=O), 137.9 (C), 136.3 (C), 129.1 (2×CH), 128.4 (4×CH), 128.0 (CH), 127.6 (2×CH), 126.4 (CH), 82.4 (C), 71.4 (CH), 66.5 (CH$_2$), 61.2 (CH), 57.8 (CH), 55.5 (CH), 52.3 (CH), 47.7 (2×CH$_2$), 37.0 (CH), 33.8 (CH$_2$), 31.48 (CH$_2$), 28.76 (CH$_2$), 27.9 (3×CH$_3$), 25.3 (CH$_2$), 24.8 (CH$_2$), 15.3 (CH$_3$), 11.0 (CH$_3$); FABHRMS (NBA/CsI) m/e 856.288 ([M+Cs]$^+$, C$_{38}$H$_{53}$N$_5$O$_9$ requires 856.2898).

(3S) and (3R) 3-(N-Benzyloxycarbonyl)amino-2-keto-4-phenylbutyryl-L-prolyl-L-isoleucyl-L-glutamine-tert-butyl Amide 3 as Illustrated in FIG. 8

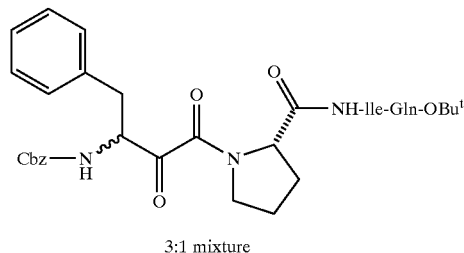

3

3:1 mixture

As illustrated in FIG. 8, oxidation of 20 was carried out using the general Dess-Martin oxidation procedure outlined above. Purification by flash chromatography eluting with 5% methanol in dichloromethane gave the desired α-keto amide 3 (S) (2:1 mixture of isomers) as a colorless oil (37 mg, quantitative). A representative synthesis is as follows: the substrate 20 (21 mg, 0.044 mmol) was dissolved in dry CH$_2$Cl$_2$ (2 mL), and Dess-Martin periodinane (26 mg, 0.088 mmol) added. The reaction mixture was stirred at ambient temperature for 24 hours, then diluted with ethyl acetate (10 mL) and quenched by addition of saturated sodium bicarbonate $_{(aq.)}$ (5 mL) and sodium thiosulfate. The aqueous phase was extracted with ethyl acetate (3×20 mL). The combined organic extracts washed with water (10 mL), brine (10 mL), dried (MgSO$_4$) and concentrated in vacua to give the crude product. Flash chromatography eluting with 30% ethyl acetate in hexane gave the desired product 3 as a 3:1 mixture of diastereomers (colorless oil) (20 mg, 95%). (S) isomer: R$_f$=0.24 (EtOAc). $^1$H NMR (400 MHz, CDCl$_3$) δ 7.38–7.16 (11H, m), 6.98 (1H, d, J 8.5), 6.80 (1H, s), 6.64 (1H, s), 5.64 (1H, d, J 8.3), 5.09 (1H, d, J 12.2), 5.02 (1H, d, J 12.2), 4.46 (1H, dd, J 8.2, 3.4), 4.21 (1H, t, J 8.1), 3.67–3.60 (1H, m), 3.59–3.45 (1H, m), 3.70–3.50 (2H, m), 3.25 (1H, dd, J 14.1, 5.5), 3.09 (1H, dd, J 14.1, 8.5), 2.29–2.12 (4H, m), 2.12–1.78 (6H, m), 1.46 (9H, s), 1.20–1.05 (1H, m), 0.93–0.83 (6H, m, 2×CH$_3$); C$^{13}$ NMR (100 MHZ, CDCl$_3$) δ197.1 (C=O), 175.1 (C=O), 171.1 (C=O), 170.5 (2×C=O), 162.9 (C=O), 156.3 (C=O), 135.7 (2×C), 129.1 (2×CH), 128.7 (2×CH), 128.5 (2×CH), 128.5 (CH), 127.5 (2×CH), 126.9 (CH), 82.4 (C), 77.2 (CH), 67.3 (CH$_2$), 61.0 (CH), 58.0 (CH), 52.3 (CH), 48.0 (2×CH$_2$), 37.0 (CH), 31.5 (CH$_2$), 29.7 (CH$_2$), 28.2 (CH$_2$), 27.9 (3×CH$_3$), 25.0 (CH$_2$), 24.8 (CH$_2$), 15.5 (CH$_3$), 10.8 (CH$_3$). (3R) isomer: $^1$H NMR (400 MHz, CDCl$_3$) δ7.38–7.16 (11H, m), 6.84 (1H, d, J 8.0), 6.21 (1H, s), 5.54 (1H, s), 5.51 (1H, d, J 8.3), 5.11–4.98 (1H, m), 5.09 (1H, d, J 12.5), 4.80 (1H, d, J 12.5), 4.75–4.61 (1H, m), 4.59 (1H, d, J 5.8), 4.50–4.29 (2H, m), 3.59–3.45 (1H, m), 3.29 (1H, dd, J 14., 3.9), 2.85 (1H, dd, J 14.0, 10.0), 2.29–2.12 (4H, m), 2.12–1.78 (6H, m), 1.46 (9H, s), 1.20–1.05 (1H, m), 0.93–0.83 (6H, m, 2×CH3). IR (NaCl) v$_{max}$ 3290, 2925, 1728, 1648, 1537, 1452, 1367, 1247, 1157; FABHRMS (NBA/CsI) m/e 854.2775 ([M+Cs]$^+$, C$_{38}$H$_{51}$N$_5$O$_9$ requires 854.2741).

2 (R), 5(R)-Bis (methoxymethyl)-3(R), 4(S)(dimethoxy) Npyrrolidine 23 as illustrated in FIG. 12

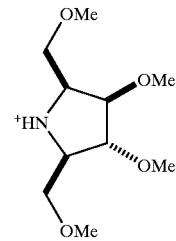

23

As illustrated in FIGS. 11 and 12, a solution of 2(R), 5(R)-bis(hydroxymethyl)-3(R), 4(S)-dihydroxypyrrolidine (806 mg, 4.95 mmol; Wong et. al J. Org. Chem. 1991, 56, 6280) in H$_2$O (25 mL) was cooled to 0° C. in an ice bath and the pH was adjusted to 9–10 with Na$_2$CO$_3$ solution (0.3M). Benzyloxycarbonyl chloride (1.4 mL, 9.9 mmol, 2 eq.) was added dropwise and the solution was stirred 1 hour at 0° C., and then 1 hour at ambient temperature. Solvent was removed in vacuo, and the residue was taken up in EtOAc, filtered, and concentrated in vacua. Flash chromatography eluting initially with 50% ethyl acetate in hexane then 100% ethyl acetate gave 2(R), 5(R)-bis(hydroxymethyl)-3(R), 4(S)-dihydroxy-N-(Benzyloxycarbonyl)-pyrrolidine product as a pale yellow oil. (1.1 g, 81%). R=0.27 (EtOAc) $^1$H NMR (400 MHz, CD$_3$OD) δ 7.37–7.33 (5H, m), 5.13 (2H, s), 4.20–4.19 (1H, m), 4.13–4.10 (1H, m), 4.00 (1H, br s), 3.95–3.55 (5H, m); $^{13}$C NMR (100 MHz, CD$_3$OD) (two rotamers) δ137.8, 129.6, 129.2, 129.0, 77.8, 77.1, 68.4, 67.4, 66.7, 63.2, 62.2, 61.7, 61.6, 61.1; FABHRMS (NBA) m/e 320.1121 ([M+Na]$^+$C$_{14}$H$_{19}$NO$_6$ requires 320.1110).

To 2(R), 5(R)-bis(hydroxymethyl)-3(R), 4(S)-dihydroxy-N-(Benzyloxycarbonyl)-pyrrolidine as synthesized above (35 mg, 0.117 mmol) in dry THF (1 mL) was added CH$_3$I (116 μL, 1.86 mmol, 16 eq.) followed by NaH (60% dispersion in mineral oil) (28.1 mg, 6 eq.). The reaction mixture was stirred at ambient temperature for 20 h. and concentrated in vacuo. Flash chromatography eluting with 12% to 20% ethyl acetate in hexane gave 2(R), 5(R)-bis (methoxymethyl)-3(R), 4(S)-dimethoxy-N-(Benzyloxycarbonyl)-pyrrolidine as a colorless oil. (40 mg, 97%). R$_f$=0.6 (50% EtOAc in Hexane) $^1$H NMR(400 MHz, CD$_3$OD) δ 7.29–7.23 (5H, m), 5.04 (2H, br s), 4.10 (1H, br s), 3.74 (3H, br, s), 3.44–3.42 (4H, m), 3.34 (3H, br s), 3.31 (3H, br s), 3.23 (6H, br s); FABHRMS (NBA) m/e 376.1722 ([M+Na]$^{+C}$$^H_{27}$NO$_6$ requires 376.1736).

To 2(R), 5(R)-bis(methoxymethyl)-3(R), 4(S)-dimethoxy-N-(Benzyloxycarbonyl)-pyrrolidine as synthesized above, (40 mg, 0.181 mmol), in methanol (2 mL) was added Pd/C (10 mg). The mixture was stirred under a balloon of H$_2$ for 3 h. Filtration through celite followed by concentration in vacuo yielded the desired product 23 as a pale yellow oil (25 mg, quant.). $^1$H NMR (250 MHz, CDCl$_3$) δ 5.19 (1H, br s) 3.8–3.55 (8H, m), 3.54–3.35 (12H, m); $^{13}$C NMR (62 MHz, CDCl$_3$) δ4.7, 83.7, 71.9, 69.1, 62.4, 59.9, 59.1, 59.0, 57.6, 57.5; FABHRMS (NBA) m/e 220.1543 ([M+H]$^+$C$_{10}$H$_{21}$NO$_4$ requires 220.1549).

Synthesis of (3S) and (3R) 3-(N-Benzyloxycarbonyl)amino-2-keto-4-phenylbutyryl-(2'(R), 5'(R)-bis(methoxymethyl]-3' (R), 4'(S)-dimethoxypyrrolidine] 900 as illustrated in FIG. 12

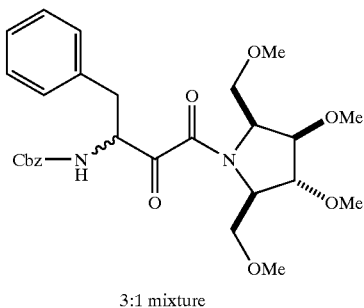

3:1 mixture

As illustrated in FIG. 12, step i–ii, the substrate 15 (70 mg, 0.213 mmol), was dissolved in dry DMF (3 mL). HOBT, 1-hydroxybenzotriazole hydrate (31 mg, 0.22 mmol), EDC, 1-(3-dimethylaminopropyl)-3-ethylcarbodiimide, (43 mg, 0.224 mmol), DIEA, diisopropylethylamine, (122 µl, 0.703 mmol) were added and the mixture stirred for 30 minutes at room temperature. The secondary amine 23 as its TFA salt (73 mg, 0.255 mmol) was added and the reaction stirred for 18 hours. The reaction mixture was diluted with ethyl acetate (20 mL) and added to saturated ammonium chloride (30 mL). The aqueous phase was extracted with ethyl acetate (3×10 mL). The combined organic phases were then washed with water (2×5 mL), 1 N HCl $_{(aq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography eluting with ethyl acetate/hexane, 1:1 to give the desired coupled product 26 as a colorless oil. The reaction was followed by oxidation using the general Dess-Martin oxidation procedure as given supra for compound 2 to give the desired product 900. Flash chromatography eluting with 20% ethyl acetate in hexane gave the α-keto amide 900 (20 mg, quantitative). R$_f$=0.63 (50% EtOAc in hexane). All analysis performed on mixture of isomers: NMR major isomer; $^1$H NMR (400 MHz CDCl$_3$) δ 7.32–7.17 (10H, m), 5.75 (1H, d, J 8.7), 5.16–5.12 (1H, m), 5.09 (1H, d, J 12.4), 5.04 (1H, d, J 12.4), 4.39 (1H, dt, J 3.9, 8.3), 3.98–3.96 (1H, m), 3.92 (1H, t, J 6.0), 3.82–3.77 (1H, m), 3.73 (1H, dd, J 10.0, 5.0), 3.55 (1H, dd, J 10.0, 2.8), 3.47–3.17 (3H, m), 3.45 (3H, s), 3.40 (3H, s), 3.26 (3H, s), 3.19 (3H, s), 3.11 (1H, dd, J 14.1, 6.92); C$^{13}$ NMR (100 MHz, CDCl$_3$) δ 197.62 (C=O), 164.7 (C=O), 155.7 (C=O), 136.4 (C), 129.7 (2×CH), 128.4 (2×CH), 128.3 (4×CH), 127.9 (CH), 126.7 (CH), 84.6 (CH), 83.6 (CH), 70.7 (CH$_2$), 69.7 (CH$_2$), 66.8 (CH$_2$), 60.7 (CH), 58.9 (CH), 58.7 (OCH$_3$), 58.7 (OCH$_3$), 58.4 (OCH$_3$), 58.4 (OCH$_3$), 56.7 (CH), 37.3 (CH$_2$) minor isomer: $^1$H NMR (400 MHz, CDCl$_3$) δ 7.32–7.17 (10H, m), 5.46 (1H, d, J 9.0), 5.11–4.87 (3H, m), 4.56–3.17 (10H, m), 3.45 (3H, s), 3.38 (3H, s), 3.31 (3H, s), 3.21 (3H, s). IR (NaCl) v$_{max}$ 2930, 1717, 1635, 1506, 1456, 1110; FABHRMS (NBA/CsI) m/e 661.1550 ([M+Cs]$^+$, C$_{28}$H$_{36}$N$_2$O$_8$ requires 661.1526).

General Peptide Coupling Procedure to Form α-Ketoamide from Proline as Illustrated in FIG. 12:

As illustrated in FIG. 12, steps i–ii, the substrate 15 (70 mg, 0.213 mmol), is dissolved in dry DMF (3 mL). HOBT, 1-hydroxybenzotriazole hydrate (31 mg, 0.22 mmol), EDC, 1-(3-dimethylaminopropyl)-3-ethylcarbodiimide, (43 mg, 0.224 mmol), DIEA, diisopropylethylamine, (122 µl, 0.703 mmol) are added and the mixture is stirred for 30 minutes at room temperature. The secondary amine 22; 23; 24; 16; 25; 36; 37; 40; 42; 44; 46; 47; 48; 52; 53; 54; 58; 59; 60; 64; 65; 66; 100; 101; 102 or 103 as its TFA salt (73 mg, 0.255 mmol) is added and the reaction stirred for 18 hours. The reaction mixture is diluted with ethyl acetate (20 mL) and added to saturated ammonium chloride (30 mL). The aqueous phase is extracted with ethyl acetate (3×10 mL). The combined organic phases are then washed with water (2×5 mL), 1 N HCl $_{(aq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired coupled product which is directly carried on to the next step for oxidation of the secondary alcohol as follows. The secondary alcohol (21 mg, 0.044 mmol) is dissolved in dry CH$_2$Cl$_2$ (2 mL), and Dess-Martin periodinane (26 mg, 0.088 mmol) added. The reaction mixture is stirred at ambient temperature for 24 hours, then diluted with ethyl acetate (10 mL) and quenched by addition of saturated sodium bicarbonate $_{(aq.)}$ (5 mL) and sodium thiosulfate. The aqueous phase is extracted with ethyl acetate (3×20 mL). The combined organic extracts washed with water (10 mL), brine (10 mL), dried (MgSO$_4$) and concentrated in vacuo to give the crude product. Flash chromatography eluting with 30% ethyl acetate in hexane gives the respective product 70;900;71;2;73;74;75;76;77;78;79a;80a;81a;79b;80b;81b; 82a;83a;84a;82b;83b;84b;1c;107;108 or 109 as a 3:1 mixture of diastereomers (colorless oil) (20 mg, 95%) as a colorless oil.

Figure 14:
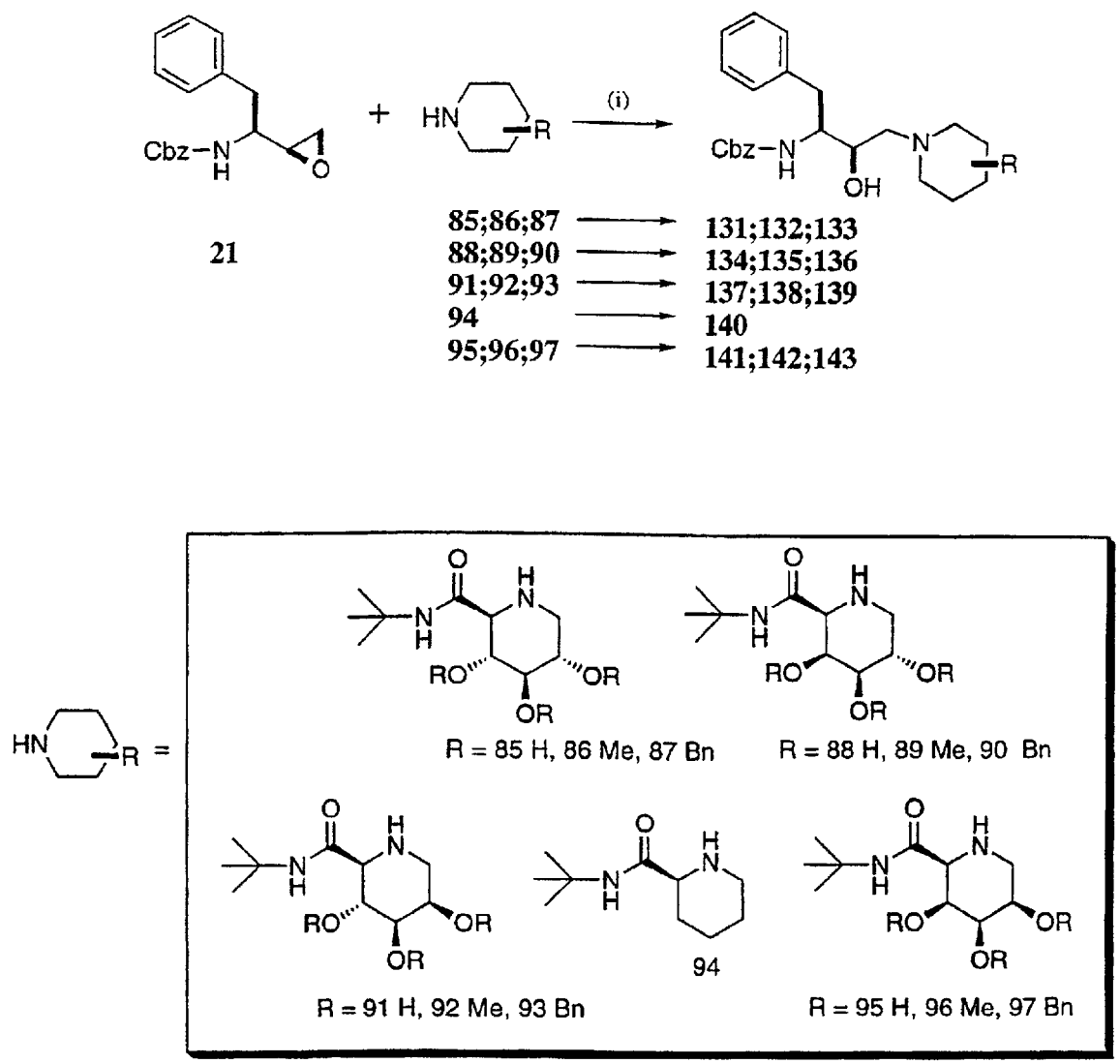
FIG. 14 illustrates a general coupling procedure to form hydroxyethyl amine compounds starting from epoxide 21 and using the indicated substituted piperidines. The procedure is as follows: (i) Methanol, Et$_3$N, reflux, 24 hours, 40–60%.

Synthesis of Epoxide 21 as shown in FIGS. 11 and 14.

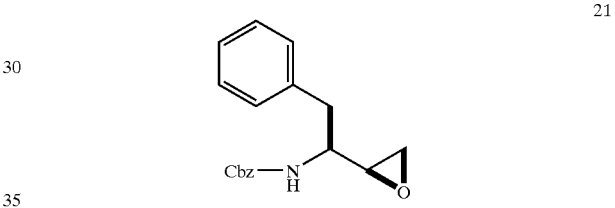

Compound 21: To a solution of compound 15 in methanol:THF (0.10 M; 1:2), at 0° C., is added a solution boran dimethyl sulfide (5 equivalents; 1.0 M) and allowed to stir for overnight. The solvent is then removed and the mixture is resuspended in methylene chloride (0.10 M) and 1.2 equivalents of triethylamine is added at 0° C. and allowed to stir for 1 hour. Next, 1.1 equivlanents of tosylchloride is added and allowed to stir at 0° C. for an additional hour. The reaction mixture is then quenched with water, extracted with 100% ethylacetate, washed over bicarbonate, brine and dried over magnesium sulfate. The crude compound is purifed by flash chromatography. The compound is then resuspended in MeOH at 0° C. and 10 equivalents of KCO$_3$ is added and allowed to stir for one hour. The reaction mixture is then filtered through celite, quenched with water, extracted with 100% ethylacetate, washed over bicarbonate, brine and dried over magnesium sulfate. The crude compound is purified by flash chromatography give compound 21.

General Procedure for Coupling of Epoxide to Proline Derivatives as Illustrated in FIG. 11

To the pyrrolidine derivative 22; 23; 24; 16; 25; 36; 37; 40; 42; 44; 46; 47; 48; 52; 53; 54; 58; 59; 60; 64; 65; 66; 100; 101; 102 or 103 (20 mg, 0.091 mmol) was added dry methanol (2 mL), Cbz-phenylalanyl epoxide 21 (27 mg, 0.091 mmol, 1.0 eq.) and triethylamine (14 µL, 0.100 mmol, 1.1 eq.). The solution was refluxed for 32 h, and then concentrated in vacua. Flash chromatography, eluting with ethyl acetate provides the desired product as a clear oil to give respectively hydroxyethyl amine derivatives: 400; 500; 600; 700; 800; 38; 39; 41; 43; 45; 49; 50; 51; 55; 56; 57; 61; 62; 63; 67; 68; 69; 1b; 104; 105; 106.

Synthesis of N-[1-Phenyl-2(S)-[(benzyloxycarbonyl)amino]-3(R)-hydroxybutan-4-(2'(R) methoxymethyl]-pyrrolidine 600 as illustrated in FIG. 11

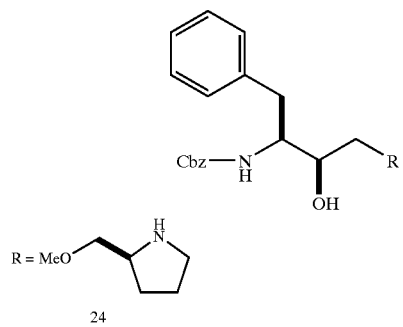

Compound 600: The pyrrolidine derivative 24 was coupled to the epoxide 21 as described in the general procedure to provide 600. Flash chromatography eluting with ethyl acetate provided the desired product as a clear oil (40 mg, 56%). $R_f$=0.15 (EtOAc). $^1$H NMR (400 MHz, CD$_3$OD) δ7.29–7.16 (10H, m), 4.97 (1H, d, J 12.7), 4.92 (1H, d, J 12.7), 3.85–3.81 (1H, m), 3.77–3.73 (1H, m), 3.42–3.25 (3H, m), 3.31 (3H, s), 3.25–3.02 (2H, m), 2.89 (1H, m), 2.64 (1H, dd, J 13.8, 10.5), 2.61–2.52 (2H, m), 1.95–1.87 (1H, m), 1.84–1.77 (2H, m), 1.61–1.55 (1H, m); C$^{13}$ NMR (100 MHz, CD$_3$OD) δ 158.5 (C=O), 140.3 (2×C), 130.5 (3×CH), 129.4 (CH), 129.2 (3×CH), 128.8 (CH), 128.5 (CH), 127.2 (CH), 73.0 (CH), 67.1 (2×CH$_2$), 59.9 (CH$_2$), 59.3 (2×CH$_2$), 57.5 (OCH$_3$), 57.2 (CH$_2$), 36.8 (CH$_2$), 28.5 (CH$_2$), 24.2 (CH$_2$); IR (NaCl) $v_{max}$ 3330, 2939, 1699, 1538, 1454, 1252, 1203, 1134, 699; FABHRMS (NBA/NaI) m/e 413.2458 ([M+H]$^+$, C$_{24}$H$_{32}$N$_2$O$_4$ requires 413.2440).

Synthesis of N-[1-Phenyl-2(S)-[(benzyloxycarbonyl)amino]-3(R)-hydroxybutan-4-[2' (R), 5' (R)-bis(methoxymethyl)]-pyrrolidine 400 as Illustrated in FIG. 11

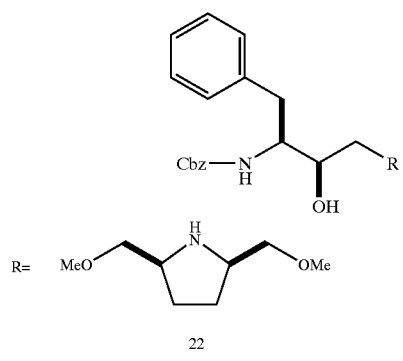

Compound 400: The pyrrolidine derivative 22 (Cignarella, G.; Nathansohn, G. *J. Org. Chem.* 1960, 26, 1500–1502) was coupled, according to the above conditions, to the epoxide 21 to provide 400. Flash chromatography eluting with 30% to 50% ethyl acetate in hexane provided the desired product as a clear oil (35 mg, 40%). $R_f$=0.47 (EtOAc/Hexane, 1:1) $^1$H NMR (400 MHz, CDCl3) δ 7.33–7.17 (10H, m), 5.02±2H, dd, J 20.4, 12.1), 3.89 (1H, m), 3.50 (1H, m), 3.37 (3H, s), 3.31 (2H, d, J 1.1), 3.24 (3H, s), 3.20–3.18 (2H, m), 2.95–2.89 (4H, m), 2.85–2.75 (2H, m), 1.87–1.83 (2H, m), 1.54–1.52 (2H, m); $^{13}$C NMR (100 MHz, CDCl$_3$) δ 137.9, 129.6, 128.4, 128.2, 127.9, 127.8, 126.2, 77.5, 76.8, 71.2, 66.6, 66.3, 60.4, 59.0, 58.8, 54.9, 36.2, 29.6; FABHRMS (NBA) m/e 457.2689 ([M+H]$^+$ C$_{26}$H$_{36}$N$_2$O$_5$ requires 457.2702).

Synthesis of N-[1-Phenyl-2(S)-[(benzyloxycarbonyl)amino]-3(R)-hydroxybutan-4-[2'(R), 5'(R)-bis(methoxymethyl)-3'(R), 4'(S)-dimethoxy]-pyrrolidine 500 as Illustrated in FIG. 11.

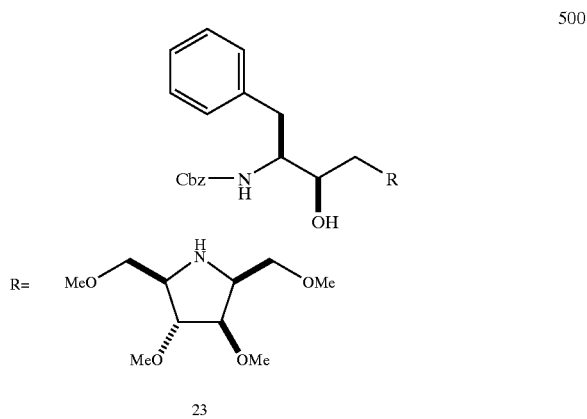

Compound 500: The pyrrolidine derivative 23 was coupled to the epoxide 21 as described above. Flash chromatography eluting with 50% ethyl acetate in hexane gave the desired product 500 as a pale yellow oil (20 mg, 42%) $R_f$=0.37 (EtOAc/Hexane, 1:1).
$^1$H NMR (400 MHz, CDCl$_3$) δ 7.33–7.19 (10H, m), 5.02 (2H, dd, J 12.3, 20.6), 4.09 (1H, br s) 3.90 (1H, m), 3.70 (1H, d, J 3.7), 3.58 (1H, dd, J 6.4, 9.3), 3.54 (2H, m), 3.37 (3H, s), 3.36 (3H, s), 3.35 (3H, s), 3.40–3.28 (5H, m), 3.28 (3H, s), 3.25–3.17 (1H, m), 2.95–2.85 (2H, m), 2.82–2.77 (2H, m); $^{13}$C NMR (100 MHz, CDCl$_3$) δ 155.9, 137.9, 129.7, 128.4, 128.3, 127.9, 127.8, 126.3, 84.8, 83.9, 75.1, 72.2, 70.6, 69.9, 66.9, 66.4, 61.0, 59.0, 58.9, 58.0, 57.1, 54.9, 29.7; FABHRMS (NBA) m/e 517.2932 ([M+H]$^+$ C$_{28}$H$_{40}$N$_2$O$_7$ requires 517.2914).

Synthesis of N-[1-Phenyl-2(S)-[(benzyloxycarbonyl)amino]-3(R)-hydroxybutan-4-L-prolyl-tert-butyl Amide 700 as Illustrated in FIG. 11.

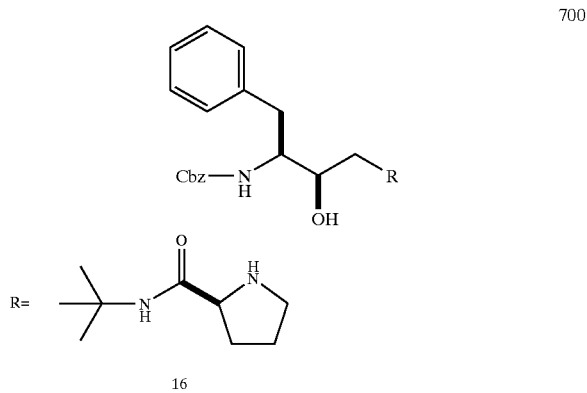

Compound 700: L-Proline tert-butyl amide 16 (synthesized supra) was coupled according to the above conditions to the epoxide 21 to give 700. Flash chromatography eluting with 100% ethyl acetate in hexane gave the desired product 700 as a colorless oil (70 mg, 48%). $R_f$=0.17 (EtOAc/Hexane, 1:1).
$^1$H NMR (400 MHz, CDCl$_3$) δ 7.33–7.14 (10H, m), 7.02 (1H, br s), 5.26 (1H, br s), 5.06 (2H, s), 3.93–3.86 (1H, m), 3.67–3.65 (1H, m), 3.29–3.16 (1H, m), 2.90–2.75 (3H, m), 2.67 (1H, d, J 1.7), 2.4B (1H, dd, J 4.8, 2.5), 2.20–2.05 (1H, m), 1.95–1.65 (3H, m), 1.30 (9H, s); $^{13}$C NMR (63 MHz, CDCl$_3$) δ 175.7, 174.4, 137.5, 129.2, 128.5, 128.4, 128.0, 127.9, 126.5, 72.1, 68.9, 66.7, 59.8, 56.1, 55.5, 50.4, 35.4, 30.9, 29.6, 28.6, 24.3; FABHRMS (NBA) m/e 468.2810 ([M+H]$^+$C$_{27}$H$_{37}$N$_3$O$_4$ requires 467.2862).

Synthesis of N-(1-Phenyl-2(S)-[(benzyloxycarbonyl)amino]-3(R)-hydroxybutan-4-(tert-butylamido)-4'(S)-methoxy]-pyrrolidine 800 as illustrated in FIG. 11.

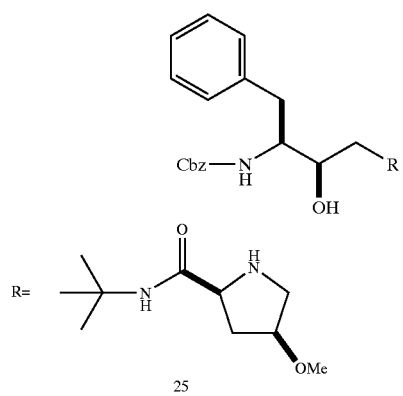

Compound 800: the pyrrolidine derivative 25 (derived from cis-4-hydroxy-L-proline) was coupled to the epoxide 21 as described above. Flash chromatography eluting with 50% ethyl acetate in hexane gave the desired product 800 as a pale yellow oil (40 mg, 60%) R$_f$=0.23 (EtOAc). $^1$H NMR (250 MHz, CDCl$_3$) δ 7.34–7.14 (10H, m), 7.04 (1H, br s), 5.01 (2H, br s,), 4.81 (1H, d, J 8.8), 3.98–3.85 (1H, m), 3.84 (1H, t, J 3.7), 3.58 (1H, dd, J 6.0, 6.1), 3.35–3.25 (1H, m), 3.28 (3H, s), 3.20–3.12 (1H, m), 3.00–2.90 (2H, m), 2.85 (1H, dd, J 13.3, 8.1), 2.71 (1H, d, J 12.4), 2.66 (1H, d, J 12.4), 2.56 (1H, dd, J 10.3, 3.1), 2.30–2.10 (1H, m), 2.05–1.95 (1H, m), 1.33 (9H, s); $^{13}$C NMR (100 MHz, CDCl$_3$) δ 174.7 (C=O), 172.0 (C=O), 137.5 (C), 129.5 (2×CH), 129.3 (C), 128.5 (3×CH), 128.4 (2×CH), 128.0 (CH), 127.9 (CH), 126.5 (CH), 79.9 (CH), 71.4 (CH), 68.3 (CH), 66.6 (C), 60.6 (CH$_2$), 59.7 (CH$_2$), 56.0 (CH$_3$O), 55.0 (CH), 50.3 (CH$_2$), 35.8 (CH$_2$), 29.7 (CH$_2$), 28.6 (3×CH$_3$); FABHRMS (NBA/CsI) m/e 630.1970 ([M+Cs]$^+$ C$_{28}$H$_{39}$N$_3$O$_5$ requires 630.1944).

Synthesis of N-[1-Phenyl-2(S)-[(benzyoxy-carbonyl)amino]-3 (R)-hydroxy-butan-4-[2'(S)-(tert-butyl-amido)-4' (R)-methoxy]-pyrrolidine 38 as Illustrated in FIG. 11.

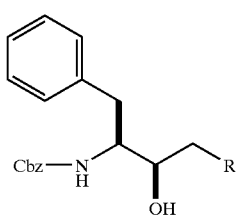

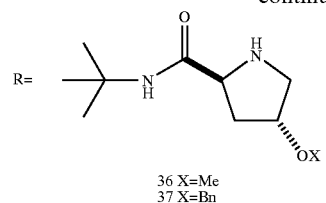

36 X=Me
37 X=Bn

Compound 38: The pyrrolidine derivative 36 (derived from trans 4-hydroxy-L-proline) was coupled to the epoxide 21 as described above. Flash chromatography eluting with 75% ethyl acetate in hexanes gave the desired product 38 as a pale yellow oil (45 mg, 40%) R$_f$=0.20 (EtOAc/Hexane, 4:1). $^1$H NMR (400 MHz, CDCl$_3$) δ 7.33–7.13 (10H, m), 6.79 (1H, br s), 5.02 (2H, s), 4.89 (1H, d,J 7.5), 3.88–3.85 (2H, m), 3.72–3.61 (1H, m), 3.49–3.33 (1H, m), 3.29 (3H, s), 3.20 (1H, t,J 8.0), 2.97–2.57 (5H, m), 2.29–2.22 (1H, m), 1.95–1.88 (1H, m), 1.67 (1H, br s), 1.31 (9H, s); $^{13}$C NMR (100 MHz, CDCl$_3$) 173.6, 156.5, 137.7, 136.3, 128.9, 128.3, 127.7, 127.6, 126.4, 79.7, 72.0, 68.0, 65.8, 60.2, 59.9, 56.6, 55.5, 50.5, 36.8, 35.3, 28.6; IR (NaCl) ν$_{max}$ 3307, 2968, 2932, 2357, 1749, 1713, 1652, 1531, 1455, 1365, 1258, 1230, 1095, 1027, 734, 698; FABHRMS (NBA) m/e 498.2955 (([M+H]$^+$C$_{28}$H$_{39}$N$_3$O$_5$ requires 498.2968); Found: C, 67.36; H, 8.30; N 8.49. C$_{29}$H$_{39}$N$_3$O$_5$ requires C, 67.57; H, 7.90; N, 8.45).

N-[1-Phenyl-2(S)-[(benzyoxycarbonyl)amino]-3(R)-hydroxybutan-4-[2'(S)-(tert-butylamido-4'(R)-benzyloxy] pyrrolidine 39 as illustrated in FIG. 11.

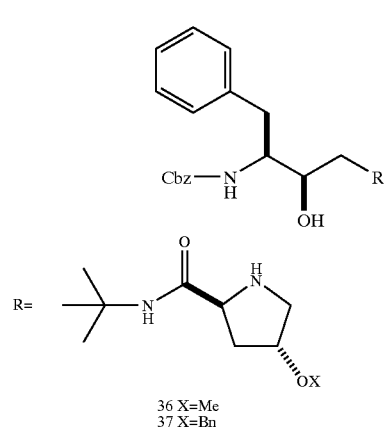

36 X=Me
37 X=Bn

Compound 39: The pyrrolidine derivative 37 (derived from trans 4-hydroxy-L-proline) was coupled to the epoxide 21 as described above. Flash chromatography eluting with 50% ethyl acetate in hexanes gave the desired product 39 as colorless oil (28 mg, 53%) R$_f$=0.20 (EtOAc/Hexane, 1:1). $^1$H NMR(400 MHz, CDCl$_3$) 7.34–7.16 (15H, m), 6.76 (1H, br s), 5.01 (2H, s), 4.85 (1H, d, J 8.2), 4.51 ($_1$H, d, J 11.7), 4.43 (1H, d, J 11.7), 4.13–4.07 (1H, m), 3.90–3.80 (1H, m), 3.70–3.62 (1H, m), 3.50–3.35 (2H, m), 3.24 (1H, t, J 8.0) 2.92–2.68 (4H, m), 2.35–2.29 (1H, m), 1.99–1.93 (1H, m), 1.63 (1H, br s), 1.30 (9H, s); $^{13}$C NMR (100 MHZ, CDCl$_3$) 137.5, 129.3, 128.6, 128.5, 128.4, 128.1, 127.9, 127.8, 127.7, 126.6, 80.1, 77.9, 71.1, 68.2, 60.8, 60.1, 55.7, 37.4, 35.9, 29.7, 28.6; IR (NaCl) ν$_{max}$ 3307, 2923, 1713, 1652, 1532, 1455, 1365, 1263, 1229, 1097, 1028, 733, 699; FABHRMS (NBA) m/e 706.2288 ([M+Cs]$^+$C$_{34}$H$_{43}$N$_3$O$_5$ requires 706.2257).

Synthesis of Compound 24 as shown in FIGS. 11; 12

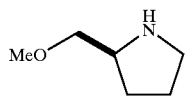

24

Compound 24: To a solution of L-proline in methanol:THF (0.10 M; 1:2), at 0° C., is added a solution boran dimethyl sulfide (5 equivalents; 1.0 M) and allowed to stir for overnight. The solvent is then removed and the mixture is resuspended in methylene chloride (0.10 M) and 1.2 equivalents of NaH (30%) is added at 0° C. and allowed to stir for 1 hour. Next, 1.1 equivlanents of methyliodide is added and allowed to stir at 0° C. for an additional hour. The reaction mixture is then quenched with water, extracted with 100% ethylacetate, washed over bicarbonate, brine and dried over magnesium sulfate. The crude compound is purifed by flash chromatography to give compound 24.

Synthesis of Compound 25 as shown in FIGS. 11; 12

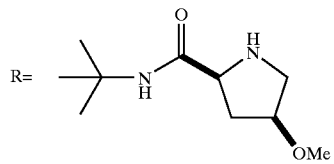

25

Compound 25: The substrate cis 4-hydroxy-L-proline commercially available from Sigma, (3.0 g, 13.9 mmol), was dissolved in dry $CH_2Cl_2$ (20 mL). HOBT, 1-hydroxybenzotriazole hydrate (2.07 g, 15.3 mmol), EDC, 1-(3-dimethylaminopropyl)-3-ethylcarbodiimide, (2.93 g, 15.3 mmol), and tert-butylamine (1.6 mL, 15.3 mmol), were added and the mixture stirred for 18 hours at ambient temperature. The reaction was diluted with ethyl acetate (100 mL), and washed with water (2×20 mL), 1 N HCl $_{(aq.)}$ (10 mL), saturated sodium bicarbonate solution $_{(aq.)}$ (10 mL), water (10 mL), brine (10 mL) and dried ($MgSO_4$) before concentration in vacuo to give the crude product. Purification by flash chromatography, eluting with 33% EtOAc in Hexane gave N-tert-butoxycarbonyl-cis-4-hydroxy-L-prolyl-tert-butyl amide as a colorless oil. The compound was then resuspended in metylene chloride (0.10 M) and 1.2 equivalents of NaH (30%) is added at 0° C. and allowed to stir for 1 hour. Next, 1.1 equivlanents of methyliodide is added and allowed to stir at 0° C. for an additional hour. The reaction mixture is then quenched with water, extracted with 100% ethylacetate, washed over bicarbonate, brine and dried over magnesium sulfate. The crude compound is purified by flash chromatography to give compound 25.

Synthesis of Compound 36 as shown in FIGS. 11; 12

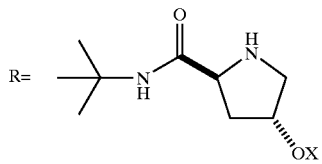

36 X=Me
37 X=Bn

Compound 36: The substrate trans-4-hydroxy-L-proline commercially available from Sigma, (3.0 g, 13.9 mmol), was dissolved in dry $CH_2Cl_2$ (20 mL). HOBT, 1-hydroxybenzotriazole hydrate (2.07 g, 15.3 mmol), EDC, 1-(3-dimethylaminopropyl)-3-ethylcarbodiimide, (2.93 g, 15.3 mmol), and tert-butylamine (1.6 mL, 15.3 mmol), were added and the mixture stirred for 18 hours at ambient temperature. The reaction was diluted with ethyl acetate (100 ml), and washed with water (2×20 mL), 1 N HCl $_{(aq.)}$ (10 mL), saturated sodium bicarbonate solution $_{(aq.)}$ (10 mL), water (10 mL), brine (10 mL) and dried ($MgSO_4$) before concentration in vacuo to give the crude product. Purification by flash chromatography, eluting with 33% EtOAc in Hexane gave N-tert-butoxycarbonyl-trans-4-hydroxy-L-prolyl-tert-butyl amide as a colorless oil. The compound was then resuspended in metylene chloride (0.10 M) and 1.2 equivalents of NaH (30%) is added at 0° C. and allowed to stir for 1 hour. Next, 1.1 equivlanents of methyliodide is added and allowed to stir at 0° C. for an additional hour. The reaction mixture is then quenched with water, extracted with 100% ethylacetate, washed over bicarbonate, brine and dried over magnesium sulfate. The crude compound is purifed by flash chromatography to give compound 36.

Synthesis of Compound 37 as shown in FIGS. 11; 12

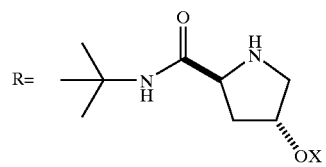

36 X=Me
37 X=Bn

Compound 37: The substrate trans-4-hydroxy-L-proline commercially available from Sigma, (3.0 g, 13.9 mmol), was dissolved in dry $CH_2Cl_2$ (20 mL). HOBT, 1-hydroxybenzotriazole hydrate (2.07 g, 15.3 mmol), EDC, 1-(3-dimethylaminopropyl)-3-ethylcarbodiimide, (2.93 g, 15.3 mmol), and tert-butylamine (1.6 mL, 15.3 mmol), were added and the mixture stirred for 18 hours at ambient temperature. The reaction was diluted with ethyl acetate (100 mL), and washed with water (2×20 mL), 1 N HCl $_{(aq.)}$ (10 mL), saturated sodium bicarbonate solution $_{(aq.)}$ (10 mL), water (10 mL), brine (10 mL) and dried ($MgSO_4$) before concentration in vacuo to give the crude product. Purification by flash chromatography, eluting with 33% EtOAc in Hexane gave N-tert-butoxycarbonyl-trans-4-hydroxy-L-prolyl-tert-butyl amide as a colorless oil. The compound was then resuspended in methylene chloride (0.10 M) and 1.2 equivalents of NaH (30%) is added at 0° C. and allowed to stir for 1 hour. Next, 1.1 equivlanents of benzylbromide is added and allowed to stir at 0° C. for an additional hour. The reaction mixture is then quenched with water, extracted with 100% ethylacetate, washed over bicarbonate, brine and dried over magnesium sulfate. The crude compound is purifed by flash chromatography to give compound 37.

Figure 9:
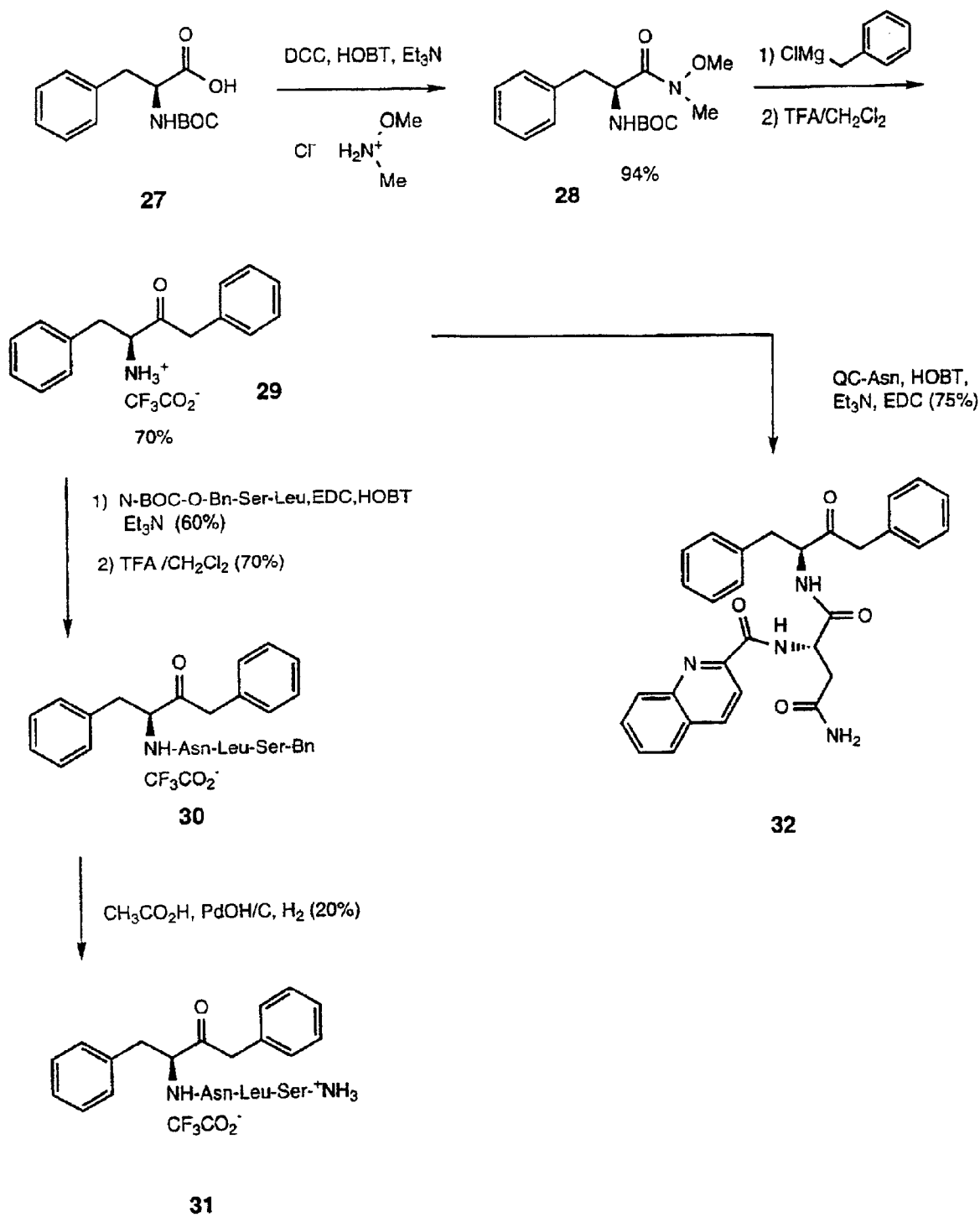
FIG. 9 illustrates the synthesis of compounds 31 and 32 with the indicated substrate and reagents.
Figure 10:
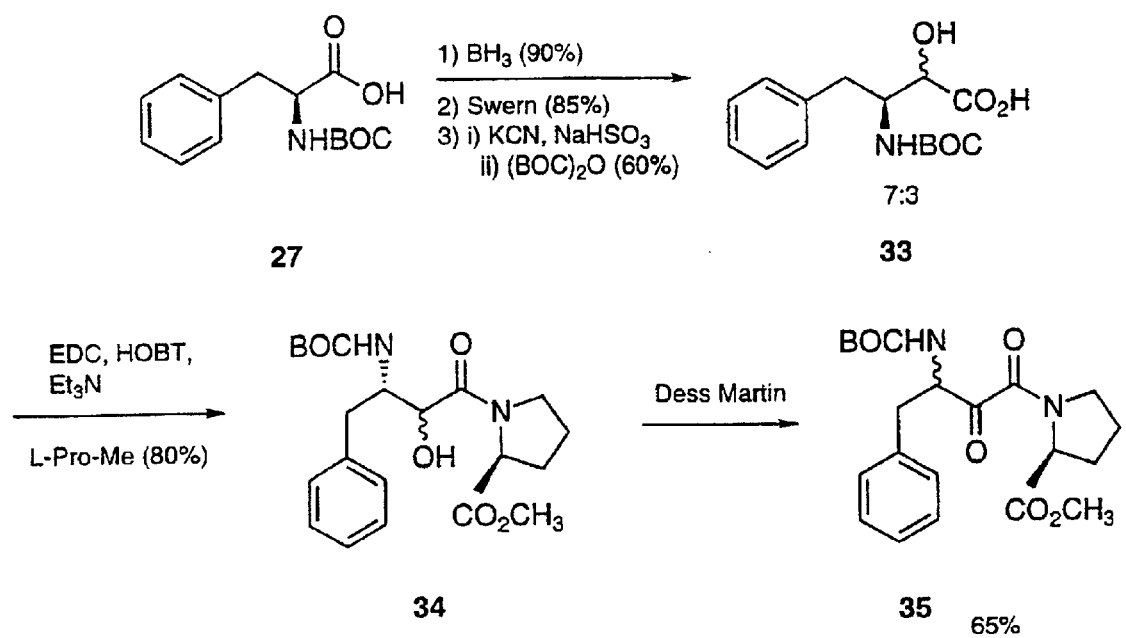
FIG. 10 illustrates the synthesis of compound 35 with the indicated substrate and reagents.

Synthesis of Compound 27 (compound is shown in FIGS. 9 and 10)

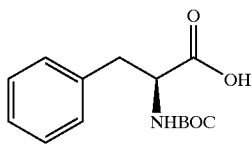

27

Compound 27: To a solution of phenylalanine (1.0 equiv.) in acetonitrile (0.10 Molar) was added 1.2 equivalents of commercially available BOC-ON [2-(tert-butoxycarbonyloxyimino)-2-phenyl-acetonitrile] and the mixture was allowed to stir for 12 hours at 25° C. The solvent was then evaporated and the crude compound 27 was carried on to the next step.

Synthesis of compound 28 as Illustrated in FIG. 9

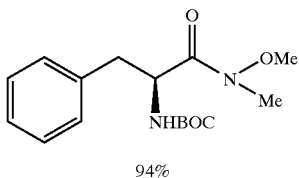

28

94%

Compound 28: The substrate 27 (70 mg, 0.213 mmol), was dissolved in dry DMF (3 mL). HOBT, 1-hydroxybenzotriazole hydrate (31 mg, 0.22 mmol), EDC, 1-(3-dimethylaminopropyl)-3-ethylcarbodiimide, (43 mg, 0.224 mmol), DIEA, diisopropyl-ethylamine, (122 μl, 0.703 mmol) were added and the mixture stirred for 30 minutes at room temperature. The commercially available N-methoxy-methyl amine hydrochloride salt (73 mg, 0.255 mmol; Aldrich) was added and the reaction stirred for 18 hours. The reaction mixture was diluted with ethyl acetate (20 mL) and added to saturated ammonium chloride (30 mL). The aqueous phase was extracted with ethyl acetate (3×10 mL). The combined organic phases were then washed with water (2×5 mL), 1 N HCl $_{(eq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography eluting with ethyl acetate/hexane, 1:1 to give the desired coupled product 28 as a colorless oil (94%).

Synthesis of 3(S)-1,4-Diphenyl-2-oxo-3-amino-N-Boc-butane (29) as illustrated in FIG. 9

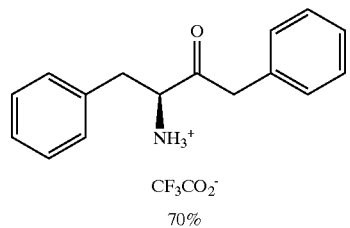

29

70%

3(S)-1,4-Diphenyl-2-oxo-3-amino-N-Boc-butane (29): To a stirred solution of N-Boc-L-phenylalanine-N-methoxy-N-methylamide (28) (5.0 g, 14.5 mmol) in anhydrous THF (50 mL) under N$_2$ at 0° C. was added 2.0 M benzyl magnesium chloride in THF (21.7 mL, 43.5 mmol). The mixture was gradually warmed at room temperature and stirred for an additional 3 h. The reaction mixture was then poured onto 1 N HCl (25 mL). The organic layer was separated and the aqueous layer was extracted with ether (3×35 mL). The combined organic layers were dried (MgSO$_4$) and concentrated to give a crude product. Purification of the crude material by flash chromatography (EA:H;1:4) afforded Boc protected intermediate to 29 as a white solid (4.8 g, 98%). R$_f$ 0.3 (EA:H;1:4); mp 86–87° C.; [α]$^{250}$+31.22° (c 2.21, CH$_2$Cl$_2$); IR 3485, 2978, 1709, 1704, 1490, 1363, 1250 cm$^{-1}$; $^1$H NMR (CDCl$_3$) 1.14 (s, 9H), 2.9–3.15 (m, 2H), 3.65 (q, 2H, J=11.6 Hz), 4.61 (d, 1H, J=6.9 Hz), 5.1 (bs, 1H), 7.0–7.2 (m, 10H) ppm; $^{13}$C NMR (CDCl$_3$) 28.3, 28.7, 47.8, 59.5, 79.9, 127.0, 127.1, 128.8, 129.2, 129.2, 129.6, 133.1, 135.2, 155.1, 206.5 ppm. HRMS: 472.0880, Calcd for C$_{21}$H$_{25}$NO$_3$+Cs$^+$: 472.0889.

3(S)-1,4-Diphenyl-2-oxo-3-amino-butane HCl (29): To a solution of 3(S)-1,4-diphenyl-2-oxo-3-amino-N-Boc-butane (Boc protected intermediate to 29) (1.4 g, 4.12 mmol) in ether (10 mL) was added a saturated solution of HCl(g)/Ether (20 mL). After 3 h the precipitate was filtered to afford a crude white solid. Recrystallization (MeOH/Ether) gave 29 as a white solid (0.96 g, 85%). $^1$H NMR (300 MHz, CD$_3$OD) 2.96 (dd, 1H, J=8.2 Hz), 3.24 (dd, 1H, J=6.2, 14.3 Hz), 3.73 (q, 2H, J=16.9 Hz), 4.41 (dd, 1H, J=2.0, 8.2 Hz) ppm. HRMS: 240.1388 Calcd. for C$_{16}$H$_{18}$NO+H$^+$: 240.1388.

Synthesis of Compound 30 as Illustrated in FIG. 9

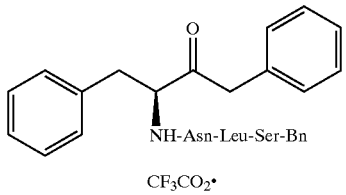

30

Compound 30: To a solution of 29 (0.032 g, 0.12 mmol) in CH$_2$Cl$_2$ (10 mL) was added O-benzyl-N-Boc-L-Ser-Leu-Asn (0.075 g, 0.15 mmol), EDC (0.032 g, 0.17 mmol), HOBt (0.045 g, 0.33 mmol) and DMAP (cat.). After 24 h the reaction mixture was washed with sat. NaHCO$_3$ (2×5 mL), 1 N HCl (2×5 mL), sat. NaCl (2×5 mL), dried (MgSO$_4$) and concentrated to give a crude solid. Recrystallization from MeOH/Ether afforded intermediate N-Boc protected compound to 30 as a white solid (0.05 g, % yield). $^1$H NMR (300 MHz, DMSO-d6) 0.72–0.85 (m, 6H), 1.35 (s, 9H), 1.50–1.72 (m, 1H), 2.30–2.45 (m, 1H), 2.80–2.90 (m, 1H), 3.05 (dd, 1H, J=5.1, 13.9 Hz), 3.5–3.63 (m, 2H), 3.69 (d, 1H), J=17.0 Hz), 3.86 (d, 1H, J=17.3 Hz), 4.20–4.30 (m, 1H), 4.30–4.45 (m, 1H), 4.46 (s, 2H), 4.48–4.51 (m, 1H), 6.80–7.42 (m, 15H) ppm. HRMS: 876.2955 Calcd for C$_{41}$N$_{53}$N$_5$O$_8$+CS$^+$: 876.2948. Anal Cacld for C$_{41}$H$_{53}$N$_5$O$_8$: C 60.20%, H 5.615, N 7.18%, S 9.41%. Found C 65.99%, H 7.22%, N 9.61%.

To a solution of intermediate N-Boc protected compound (0.12 g, 0.16 mmol) in CH$_2$Cl$_2$ was added a solution of 305 TFA/CH$_2$Cl$_2$. After 24 h the mixture was concentrated to afford a crude white solid which after recrystallization (MeOH/Ether) afforded the title compound 30 as a white solid (0.09 g, 75%). $^1$H NMR (300 MHz, CD$_3$OD) 0.71–0.85 (m, 6H), 1.40–1.60 (m, 3H), 2.40–0.262 (m, 2H), 2.70–0.291 (m, 1H), 2.91–3.01 (m, 1H), 3.50–3.58 (m, 1H), 3.60–3.72 (m, 2H), 3.75–3.82 (m, 1H), 3.88–4.00 (m, 1H), 4.20–4.30 (m, 1H), 4.44–4.61 (m, 2H), 6.93–7.45 (m, 15H) ppm. HRMS: 644.3448 Calcd for C$_{36}$H$_{46}$N$_5$O$_6$+H$^+$: 644.3448.

Synthesis of Compound 31 as Illustrated in FIG. 9

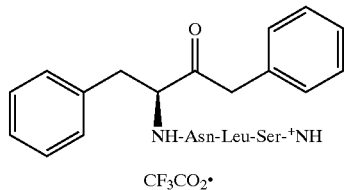

Compound 31: A solution of 30 (80 mg, 0.11 mmol) in glacial acetic (10 ml) containing Pd(OH)$_2$/C (cat.) was placed under a H$_2$ atmosphere at 50 psi. After 12 h the solution was filtered and the crude solid was recrystallized from MeOH/Ether to afford the title compound (15 mg, 22%). $^1$H NMR (300 MHz, CD$_3$OD) 0.82 (t, 6H, J=6.6 Hz), 1.39 (t, 2H, J=7.2 Hz), 1.50–1.60 (m, 1H), 2.36 (dd, 1H, J=8.1, 15.6 Hz), 2.44–2.50 (m, 1H), 2.38 (dd, 1H, J=4.5, 13.9 Hz), 3.05 (dd, 1H, J=4.9, 13.9 Hz), 3.69 (d, 1H, J=17.3 Hz), 3.85 (dd, 1H, J=17.2 Hz), 4.28–4.32 (m, 1H)$_1$, 4.35–4.42 (m, 1H), 4.48–4.53 (m, 1H), 6.80–7.35 (m, 10H) ppm. HRMS: 686.1961 Calcd for C$_{31}$H$_{43}$N$_5$O$_8$+CS$^+$: 686.1955.

Synthesis of Compound 32 as Illustrated in FIG. 9

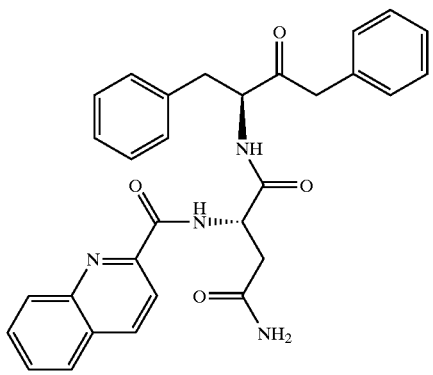

Compound 32: To a solution of 29 (0.17 g, 0.62 mmol) in DMF (5 mL) was added HOBt (0.17, 1.2 mmol), DMAP (cat.), EDC (0.12 g, 0.62 mmol), Et3N (0.06 g, 0.09 mL, 0.62 mmol) and quinolinic-Asn (g, 0.52 mmol). After 12 h the reaction mixture was taken up in EA (50 mL). The organic layer was dried (MgSO$_4$) and concentrated to give a crude brown solid. Recrystallization from MeOH/ether gave a white solid as 32 (0.12 g, 43%). $^1$H NMR (300 MHz, DMSO-d$_6$) 2.62 (dd, 1H, J=4.9, 15.3 Hz), 2.75 (dd, 1H, J=6.9, 15.5 Hz), 2.84 (dd, 1H, J=14.3, 23.4 Hz), 3.06 (dd, 1H, J=4.6, 13.7 Hz), 3.76 (d, 1H, J=17.0 Hz), 3.91 (d, 1H, J=17.0 Hz), 4.51 (q, 1H, J=7.7 Hz), 4.82 (q, 1H, J=6.8 Hz), 6.95–7.32 (m, 11H), 7.48 (s, 1H), 7.73 (t, 1H, J=7.1 Hz), 7.89 (t, 1H, J=8.3 Hz), 8.13 (q, eH, J=8.7 Hz), 8.58 (t, 2H, J=6.7 Hz) ppm. HRMS: 641.1166 Calcd for C$_{30}$H$_{28}$NO$_4$+CS$^+$: 641.1165.

Synthesis of Compound 34 as Illustrated in FIG. 10

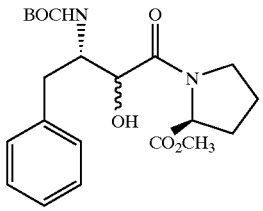

Compound 34: To a solution of compound 33 (7:3 mixture) (0.21 g, 0.71 mmol), as previously prepared from 27 (Yuan, W.; Munoz, B.; Wong, C.-H.; Haeggstrom, J. Z.; Wetterholm, A.; Samuelsson, B. J. Med. Chem. 1993, 36, 211) in CH$_2$Cl$_2$ (10 mL) was added L-proline methyl ester HCl (0.18 g, 1.1 mmol), EDC (0.16 g, 0.85 mmol), HOBt (0.21 g, 1.56 mmol) and DMAP (cat.). After 24 h the reaction mixture was washed with sat. NaHCO$_3$ (2×2 mL), 1 N HCl (2×2 ml) and sat. NaCl (1×1 mL). The organic layer was dried (MgSO$_4$), filtered and concentrated to give a crude solid. Purification by flash chromatography (EA:H; 1:4) gave the white solid compound 34 as a single (2R, 3S) (0.23 g, 80%). R$_f$=0.20 (EA:H;1:4); $^1$H NMR (300 MHz, CDCl$_3$) 1.34 (s, 9H), 1.90–2.11 (m, 4H), 2.88–2.91 (m, 2H), 3.11–3.20 (m, 1H), 3.36 (q, 1H, J=7.6 Hz), 3.65 (s, 3H), 3.89 (d, 1H, J=5.1 Hz), 4.08 (d, 1H, J=5.7 Hz), 4.15 (q, 1H, J=9.7 Hz), 4.39 (d, 1H, J=7.4 Hz), 4.89 (d, 1H, J=9.9 Hz), 7.10–7.35 (m, 5H) ppm. HRMS: 539.1169 Calcd for C$_{21}$H$_{30}$N$_2$O$_6$+Cs$^+$: 539.1158.

Synthesis of Compound 35 as Illustrated in FIG. 10

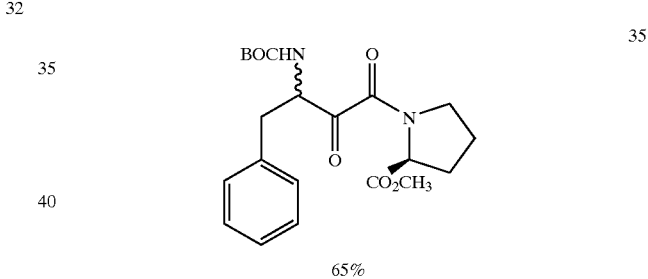

65%

Compound 35: To a solution of compound 34 (0.062 g, 0.15 mmol) in anhydrous CH$_2$Cl$_2$ under N$_2$ at room temperature was added the Dess-Martin reagent (0.078 g, 0.18 mmol). After 12 h the reaction was quenched with sat. NaHCO$_3$ (4 mL) and sat. Na$_2$S$_2$O$_3$ (4 mL). Ether (40 mL) was added to the reaction and then stirred for 10 min. The reaction mixture was washed with sat. NaCl (2×10 mL), dried (MgSO$_4$), filtered and concentrated to give a crude oil. Purification by flash chromatography (EA:H; 1:3) afforded compound 35 as a 1:0.8 mixture of an oil (0.030 g, 65%). $^1$H NMR (300 MHz, CDCl$_3$) 1.35; 1.35 (s;s, 9H), 1.91–2.01 (m, 3H), 2.15–2.23 (m, 1H), 3.09–3.41 (m, 1H), 3.51–3.70 (m, 2H), 3.70 (m, 2H), 3.70 tq, 3H, J=6.3, 7.8 Hz), 4.40–4.49 (m, 1H), 4.72d–4.85 (m, 1H), 4.93–5.00 (m, 1H), 5.10–5.23 (m, 1H), 7.05–7.35 (m, 5H) ppm. HRMS: 537.1002 Calcd for C$_{21}$H$_{28}$N$_2$O$_6$+Cs$^+$: 537.1002.

Figure 13:
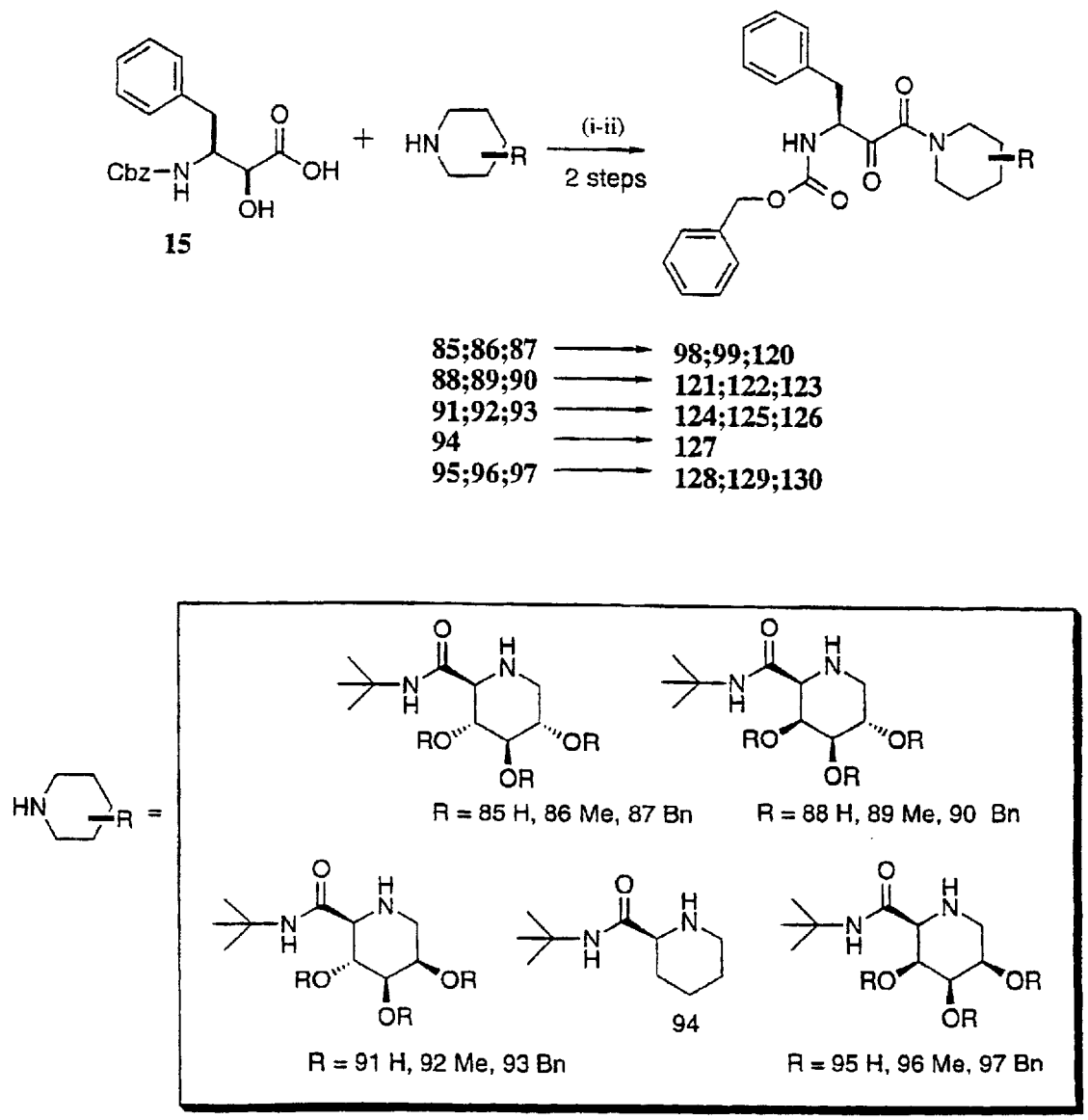
FIG. 13 illustrates a general coupling procedure to form α-ketoamide compounds starting from carboxyacid 15 and using the indicated substituted piperidines. The two step procedure is as follows: (i) EDC, HOBT, DIEA, DMF/CH$_3$CN, (1:1); (ii) Dess-Martin periodinane oxidation, CH$_2$Cl$_2$, quantitative.

General Peptide Coupling Procedure to Form α-Ketoamide from Piperidine as Illustrated in FIG. 13:

As illustrated in FIG. 13, steps i–ii, the substrate 15 (70 mg, 0.213 mmol), is dissolved in dry DMF (3 mL). HOBT, 1-hydroxybenzotriazole hydrate (31 mg, 0.22 mmol), EDC, 1-(3-dimethylaminopropyl)-3-ethylcarbodiimide, (43 mg, 0.224 mmol), DIEA, diiopropylethylamine, (122 μl, 0.703 mmol) are added and the mixture is stirred for 30 minutes at room temperature. The secondary amine 85;86;87;88;89;90;91;92;93;94;95;96 or 97 as its TFA salt (73 mg, 0.255 mmol) is added and the reaction stirred for 18 hours. The reaction mixture is diluted with ethyl acetate (20 mL) and added to saturated ammonium chloride (30 mL). The aqueous phase is extracted with ethyl acetate (3×10 mL). The combined organic phases are then washed with water (2×5 mL), 1 N HCl $_{(aq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired coupled product which is directly carried on to the next step for oxidation of the secondary alcohol as follows. The secondary alcohol (21 mg, 0.044 mmol) is dissolved in dry CH$_2$Cl$_2$ (2 mL), and Dess-Martin periodinane (26 mg, 0.088 mmol) added. The reaction mixture is stirred at ambient temperature for 24 hours, then diluted with ethyl acetate (10 mL) and quenched by addition of saturated sodium bicarbonate $_{(aq.)}$ (5 mL) and sodium thiosulfate. The aqueous phase is extracted with ethyl acetate (3×20 mL). The combined organic extracts washed with water (10 mL), brine (10 mL), dried (MgSO$_4$) and concentrated in vacuo to give the crude product. Flash chromatography eluting with 30% ethyl acetate in hexane gives the respective product 98; 99; 120; 121; 122; 123; 124; 125; 126; 127; 128; 129 or 130 as a 3:1 mixture of diastereomers (colorless oil) (20 mg, 95%) as a colorless oil.
General Procedure for Coupling of Epoxide to Proline Derivatives as Illustrated in FIG. 14

To the pyrrolidine derivative 85;96;87;88;89;90;91;92;93;94;95;96 or 97 (20 mg, 0.091 mmol) was added dry methanol (2 mL), Cbz-phenylalanyl epoxide 21 (27 mg, 0.091 mmol, 1.0 eq.) and triethylamine (14 μL, 0.100 mmol, 1.1 eq.). The solution was refluxed for 32 h, and then concentrated in vacuo. Flash chromatography, eluting with ethyl acetate provides the desired product as a clear oil to give respectively hydroxylethyl amine derivatives: 131; 132; 133; 134; 135; 136; 137; 138; 139; 140; 141; 142 or 143.

Figure 15:
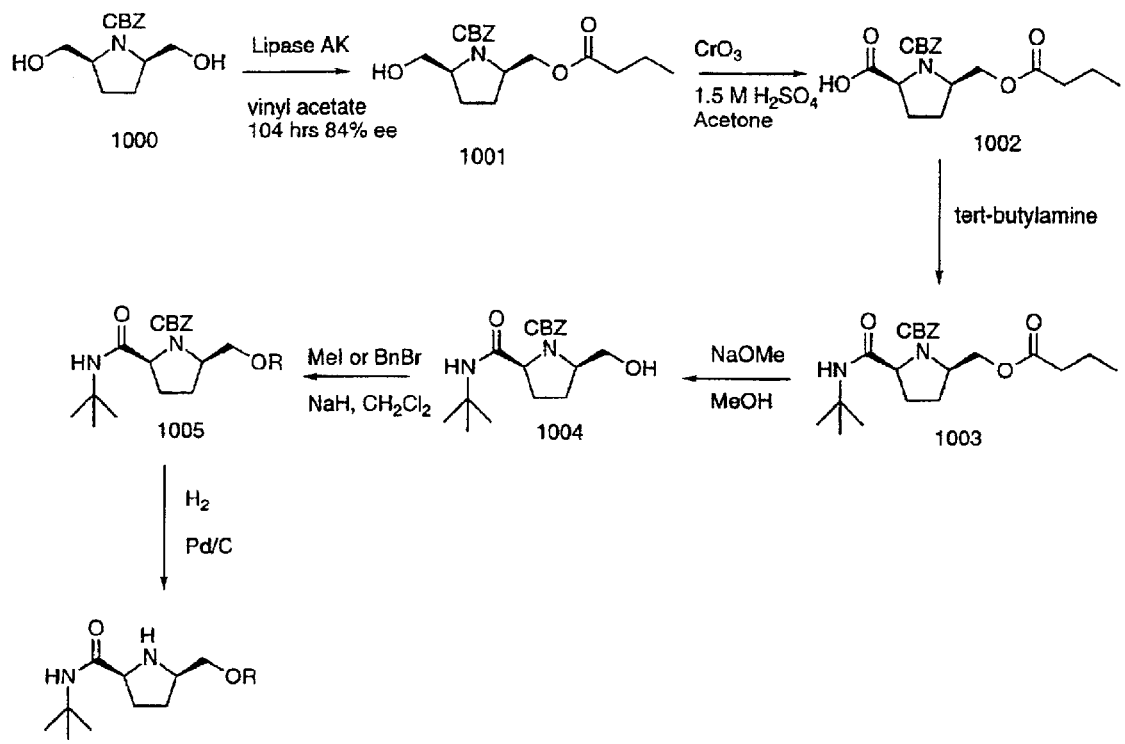
FIG. 15 illustrates the synthesis of pyrolidines 46, 47 and 48 with the indicated substrate and reagents.

Synthesis of compound 1001 as illustrated in FIG. 15: A typical acylation is as follows: Compound 1000 (0.16 mmol; cis-dihydroxymethyl-pyrolidine from Aldrich followed by standard BOC protection; vida supra), the vinyl acetate (0.05 mL; Aldrich), DMF (0.2 mL; other solvents such as methylene chloride, chloroform, acetonitrile, tert-butyl alcohol, 3-methyl-3-pentanol, DMSO and THF can also be used), H$_2$O (0.005 mL), triethylamine (0.005 mL) and subtilisin BPN' or subtilisin Carlsberg (5 mg, 50 U) is stirred at 37° C. for 36 h. The reaction is worked up by adding EtOAc and filtering the reaction mixture through celite. The filtrate is washed with sat. NaHCO$_3$ solution, then with brine, dried over MgSO$_4$ and concentrated in vacuo to give an oil. Some of the product, if possible, is crystallized out at this stage by addition of diisopropyl ether. The mother liquor is then chromatographed (SiO$_2$, hexane/EtOAc, 9/1-1/1) to give the product 1001.

Synthesis of compound 1002 as illustrated in FIG. 15: Compound 1002 was disolved in 0.10 Molar solution of acetone and then 1.5 M sulfuric acid was added at 0° C. Next chromium (VI) oxide (1.1 equivalents; Aldrich) was added and the mixture was allowed to stir for 2 hours. The reaction is worked up by adding EtOAc and washed with sat. NaHCO$_3$ solution, then with brine, dried over MgSO$_4$ and concentrated in vacuo to give an oil. The mother liquor is then chromatographed to give the product 1002.

Synthesis of compound 1003 as illustrated in FIG. 15: The substrate 1002 (70 mg, 0.213 mmol), is dissolved in dry methylene chloride (3 mL). EDC, 1-(3-dimethylaminopropyl)-3-ethylcarbodiimide, (43 mg, 0.224 mmol) is added and the mixture is stirred for 30 minutes at room temperature. tert-butyl amine (73 mg, 0.255 mmol) is added and the reaction stirred for 18 hours. The reaction mixture is diluted with ethyl acetate (20 mL) and added to saturated ammonium chloride (30 mL). The aqueous phase is extracted with ethyl acetate (3×10 mL). The combined organic phases are then washed with water (2×5 mL), 1 N HCl $_{(aq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired coupled product.

Synthesis of compound 1004 as illustrated in FIG. 15: Compound 1003 was disolved in 0.10 Molar solution of methanol and then 0.10 equivalents sodium methoxide was added at 0° C. and the mixture was allowed to stir for 2 hours. The reaction is concentrated in vacuo to give an oil. The mother liquor is then chromatographed to give the product 1004.

Synthesis of compound 1005 as illustrated in FIG. 15: Compound 1004 (290 mg, 1.09 mmol; Aldrich) in methylene chloride (2 mL) at 0° C. under argon was added NaH (60% disp. in mineral oil) (96 mg, 2.40 mmol, 2.2 eq.). The mixture was allowed to stir for 20 min., and then benzyl bromide or methyl iodide (0.14 mL, 1.20 mmol, 1.1 eq.) was added. The mixture was allowed to stir for 1 hr at 0° C. and then quenched with a few drops of water. Saturated NaHCO$_3$ solution was added (10 mL) and the aqueous layer was washed with ethyl ether. The aqueous layer was then acidified to pH 2 with 1N HCl, extracted with ethyl acetate (3×20 mL), dried over MgSO$_4$, and concentrated to afford a yellow oil. The mother liquor is then chromatographed to give the product 1005.

Synthesis of compound 46; 47 or 48 as illustrated in FIG. 15: Compound 46; 47 or 48: To a solution of CBZ-protected amine (0.092 mmol) in MeOH (2 mL) was added 20% palladium hydroxide on carbon (10 mg) and the suspension was stirred vigorously under a balloon of hydrogen at ambient temperature. After 5 min., TLC indicated that the reaction was complete. The suspension was filtered through a pad of celite and concentrated in vacuo to yield product.

Figure 16:
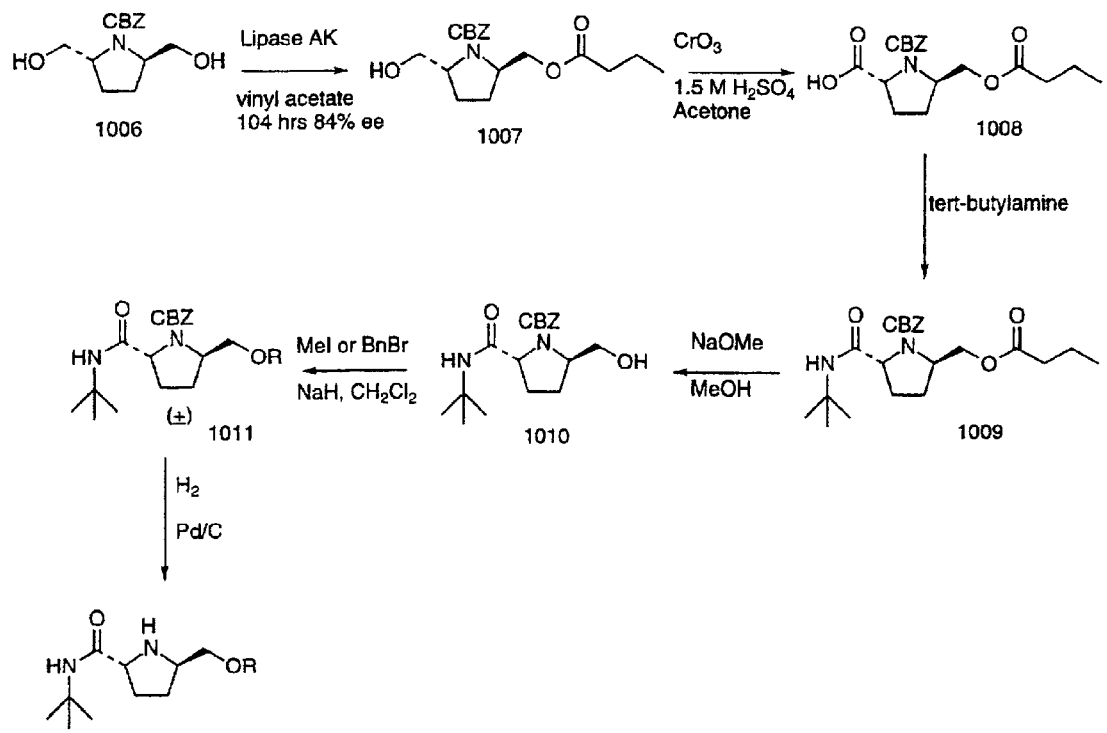
FIG. 16 illustrates the synthesis of pyrolidines 52, 53 and 54 with the indicated substrate and reagents.

Synthesis of compound 1007 as illustrated in FIG. 16: A typical acylation is as follows: Compound 1006 (0.16 mmol; trans-dihydroxymethyl-pyrolidine from Aldrich followed by standard BOC protection; vida supra), the vinyl acetate (0.05 mL; Aldrich), DMF (0.2 mL; other solvents such as methylene chloride, chloroform, acetonitrile, tert-butyl alcohol, 3-methyl-3-pentanol, DMSO and THF can also be used), H$_2$O (0.005 mL), triethylamine (0.005 mL) and subtilisin BPN' or subtilisin Carlsberg (5 mg, 50 U) is stirred at 37° C. for 36 h. The reaction is worked up by adding EtOAc and filtering the reaction mixture through celite. The filtrate is washed with sat. NaHCO$_3$ solution, then with brine, dried over MgSO$_4$ and concentrated in vacuo to give an oil. Some of the product, if possible, is crystallized out at this stage by addition of diisopropyl ether. The mother liquor is then chromatographed (SiO$_2$, hexane/EtOAc, 9/1-1/1) to give the product 1007.

Synthesis of compound 1008 as illustrated in FIG. 16: Compound 1008 was disolved in 0.10 Molar solution of acetone and then 1.5 M sulfuric acid was added at 0° C. Next chromium (VI) oxide (1.1 equivalents; Aldrich) was added and the mixture was allowed to stir for 2 hours. The reaction is worked up by addina EtOAc and washed with sat. NaHCO$_3$ solution, then with brine, dried over MgSO$_4$ and concentrated in vacua to give an oil. The mother liquor is then chromatographed to give the product 1008.

Synthesis of compound 1009 as illustrated in FIG. 16: The substrate 1008 (70 mg, 0.213 mmol), is dissolved in dry methylene chloride (3 mL). EDC, 1-(3-dimethylaminopropyl)-3-ethylcarbodiimide, (43 mg, 0.224 mmol) is added and the mixture is stirred for 30 minutes at room temperature. tert-butyl amine (73 mg, 0.255 mmol) is added and the reaction stirred for 18 hours. The reaction mixture is diluted with ethyl acetate (20 mL) and added to saturated ammonium chloride (30 mL). The aqueous phase is extracted with ethyl acetate (3×10 mL). The combined organic phases are then washed with water (2×5 mL), 1 N HCl $_{(aq.)}$ (5 mL), saturated sodium bicarbonate solution $_{(aq.)}$ (50 mL), water (5 mL), brine 15 mL) and dried (MgSO$_4$) before concentration in vacua to give the crude product. Flash chromatography, eluting with 1:1 ethyl acetate/hexane gives the desired coupled product.

Synthesis of compound 1010 as illustrated in FIG. 16: Compound 1009 was disolved in 0.10 Molar solution of methanol and then 0.10 equivalents sodium methoxide was added at 0° C. and the mixture was allowed to stir for 2 hours. The reaction is concentrated in vacuo to give an oil. The mother liquor is then chromatographed to give the product 1010.

Synthesis of (±) compound 1011 as illustrated in FIG. 16: Compound 1010 (290 mg, 1.09 mmol; Aldrich) in methylene chloride (2 mL) at 0° C. under argon was added NaH (60% disp. in mineral oil) (96 mg, 2.40 mmol, 2.2 eq.). The mixture was allowed to stir for 20 min., and then benzyl bromide or methyl iodide (0.14 mL, 1.20 mmol, 1.1 eq.) was added. The mixture was allowed to stir for 1 hr at 0° C. and then quenched with a few drops of water. Saturated NaHCO$_3$ solution was added (10 mL) and the aqueous layer was washed with ethyl ether. The aqueous layer was then acidified to pH 2 with 1N HCl, extracted with ethyl acetate (3×20 mL), dried over MgSO$_4$, and concentrated to afford a yellow oil. The mother liquor is then chromatographed to give the product 1011.

Synthesis of compound 52; 53 or 54 as illustrated in FIG. 16: Compound 52; 53 or 54: To a solution of CBZ-protected amine (0.092 mmol) in MeOH (2 mL) was added 20% palladium hydroxide on carbon (10 mg) and the suspension was stirred vigorously under a balloon of hydrogen at ambient temperature. After 5 min., TLC indicated that the reaction was complete. The suspension was filtered through a pad of celite and concentrated in vacuo to yield product.

Figure 17:
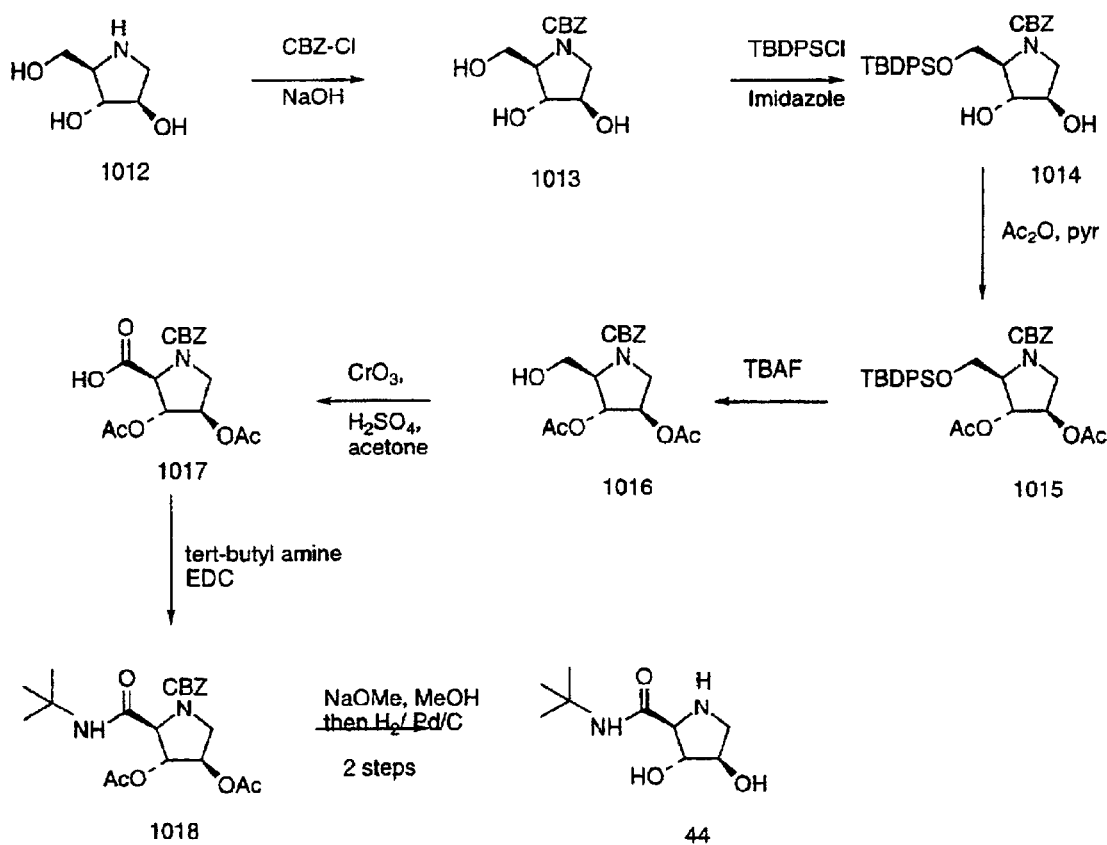
FIG. 17 illustrates the synthesis of pyrolidine 44 with the indicated substrate and reagents.

Synthesis of compound 1013 as illustrated in FIG. 17: Compound 1012 (290 mg, 1.09 mmol; Aldrich) in methylene chloride (0.10 Molar) at 0° C. under argon was added sodium hydroxide (0.10 equivalents), followed by CBZ-Cl (1.1 equivalents; Aldrich) and the mixture was stirred at 0° C. for 20 min. and then quenched with a few drops of water. Saturated ammonium chloride solution was added (10 mL) and the aqueous layer was washed with ethyl ether. The aqueous layer was then neutralized with saturated sodium bicarbonate solution, extracted with ethyl acetate (3×20 mL), dried over MgSO$_4$, and concentrated to afford a yellow oil. The mother liquor is then chromatographed to give the product 1013.

Synthesis of compound 1014 as illustrated in FIG. 17: To a solution of substrate 1013 (0.5 mmol) in anhydrous DMF (5 mL) was added TBDPSCl (1.05 eq: Aldrich), Et$_3$N (1.1 eq), and a catalytic amount of imidazole. The solution was stirred at ambient temperature for 15 hr and then was partitioned between EtOAc (60 mL) and H$_2$O (30 mL). The organic layer was then washed with sat'd NH$_4$cl$_{(aq.)}$ solution (2×30 mL), water (30 mL), brine (30 mL), dried over MgSO$_4$, and concentrated in vacuo to yield product. The mother liquor is then chromatographed to give the product 1014.

Synthesis of compound 1015 as illustrated in FIG. 17: To a solution of substrate 1014 (0.5 mmol) in anhydrous pyridine (5 mL) was added acetic anhydride (1.05 eq: Aldrich). The solution was stirred at ambient temperature for 15 hr and then was partitioned between EtOAc (60 mL) and H$_2$O (30 mL). The organic layer was then washed with sat'd NH$_4$Cl$_{(aq.)}$ solution (2×30 mL), water (30 ml), brine (30 mL), dried over MgSO$_4$, and concentrated in vacuo to yield product. The mother liquor is then chromatographed to give the product 1015.

Synthesis of compound 1016 as illustrated in FIG. 17: The substrate was dissolved in THF and cooled to 0° C. TBAF (1.0 M solution in THF) was added (1.05 eq.) and the reaction monitored by TLC. After 30 min. at 0° C., the reaction was complete and the solvent was evaporated under reduced pressure. The crude material was applied to a short column of silica gel and eluted to give the product.

Synthesis of compound 1017 as illustrated in FIG. 17: Compound 1016 was disolved in 0.10 Molar solution of acetone and then 1.5 M sulfuric acid was added at 0° C. Next chromium (VI) oxide (1.1 equivalents; Aldrich) was added and the mixture was allowed to stir for 2 hours. The reaction is worked up by adding EtOAc and washed with sat. NaHCO$_3$ solution, then with brine, dried over MgSO$_4$ and concentrated in vacuo to give an oil. The mother liquor is then chromatographed to give the product 1017.

Synthesis of compound 1018 as illustrated in FIG. 17: The substrate 1017 (70 mg, 0.213 mmol), is dissolved in dry methylene chloride (3 mL). EDC, 1-(3-dimethylaminopropyl)-3-ethylcarbodiimide, (43 mg, 0.224 mmol) is added and the mixture is stirred for 30 minutes at room temperature. tert-butyl amine (73 mg, 0.255 mmol) is added and the reaction stirred for 18 hours. The reaction mixture is diluted with ethyl acetate (20 mL) and added to saturated ammonium chloride (30 mL). The aqueous phase is extracted with ethyl acetate (3×10 mL). The combined organic phases are then washed with water (2×5 mL), 1 N HCl $_{(aq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired coupled product.

Synthesis of compound 44 as illustrated in FIG. 17: Step (1) Compound 1018 was disolved in 0.10 Molar solution of methanol and then 0.10 equivalents sodium methoxide was added at 0° C. and the mixture was allowed to stir for 2 hours. The reaction is concentrated in vacuo to give an oil. The mother liquor is then chromatographed to give the CBZ-protected amine. Step (2) To a solution of CBZ-protected amine (0.092 mmol) in MeOH (2 mL) was added 20% palladium hydroxide on carbon (10 mg) and the suspension was stirred vigorously under a balloon of hydrogen at ambient temperature. After 5 min., TLC indicated that the reaction was complete. The suspension was filtered through a pad of celite and concentrated in vacuo to yield product compound 44.

Figure 18:
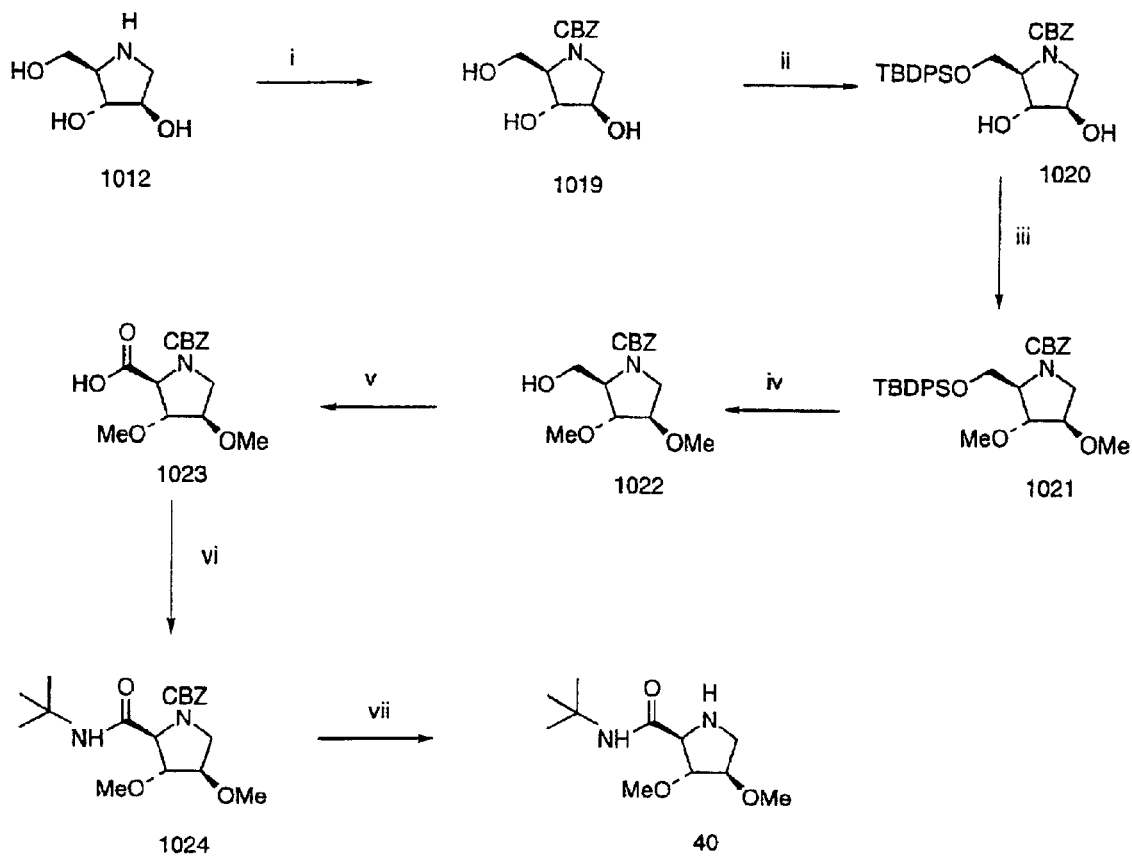
FIG. 18 illustrates the synthesis of pyrolidine 40 with the following steps: (i) CBZ-Cl, methylene chloride; (ii) TBDPSCl, Et$_3$N, DMF; (iii) Methyl iodide, sodium hydride, DMF; (iv) TBAF, THF; (v) 1.5 M H$_2$SO$_4$, CrO$_3$, acetone; (vi) H$_2$N$^t$Bu, EDC, methylene chloride; (vii) H$_2$' Pd(OH)$_2$ on Carbon, MeOH.

Synthesis of compound 1019 as illustrated in FIG. 18: Compound 1012 (290 mg, 1.09 mmol; Aldrich) in methylene chloride (0.10 Molar) at 0° C. under argon was added sodium hydroxide (0.10 equivalents), followed by CBZ-Cl (1.1 equivalents; Aldrich) and the mixture was stirred at 0° C. for 20 min. and then quenched with a few drops of water. Saturated ammonium chloride solution was added (10 mL)

and the aqueous layer was washed with ethyl ether. The aqueous layer was then neutralized with saturated sodium bicarbonate solution, extracted with ethyl acetate (3×20 mL), dried over MgSO$_4$, and concentrated to afford a yellow oil. The mother liquor is then chromatographed to give the product 1019.

Synthesis of compound 1020 as illustrated in FIG. 18: To a solution of substrate 1019 (0.5 mmol) in anhydrous DMF (5 mL) was added TBDPSCl (1.05 eq: Aldrich), Et$_3$N (1.1 eq), and a catalytic amount of imidazole. The solution was stirred at ambient temperature for 15 hr and then was partitioned between EtOAc (60 mL) and H$_2$O (30 mL). The organic layer was then washed with sat'd NH$_4$Cl$_{(aq.)}$ solution (2×30 mL), water (30 mL), brine (30 mL), dried over MgSO$_4$, and concentrated in vacua to yield product. The mother liquor is then chromatographed to give the product 1020.

Synthesis of compound 1021 as illustrated in FIG. 18: To an ice-cooled solution of substrate (0.2 mmol) in anhydrous DMF (2 mL) under argon was added NaH (60% disp. in mineral oil) (2.2 eq.). The mixture was allowed to stir for 20 min., and then methyl iodide or benzyl bromide (1.1 eq.) was added. The mixture was allowed to stir for 1 hr at 0° C. and then quenched with a few drops of water. Saturated NaHCO$_3$ solution was added (10 ml) and the aqueous layer was washed with ethyl ether. The aqueous layer was then acidified to pH 2 with 1N HCl, extracted with ethyl acetate (3×20 mL), dried over MgSO$_4$, and concentrated to afford product. The mother liquor is then chromatographed to give the product 1021.

Figure 19:
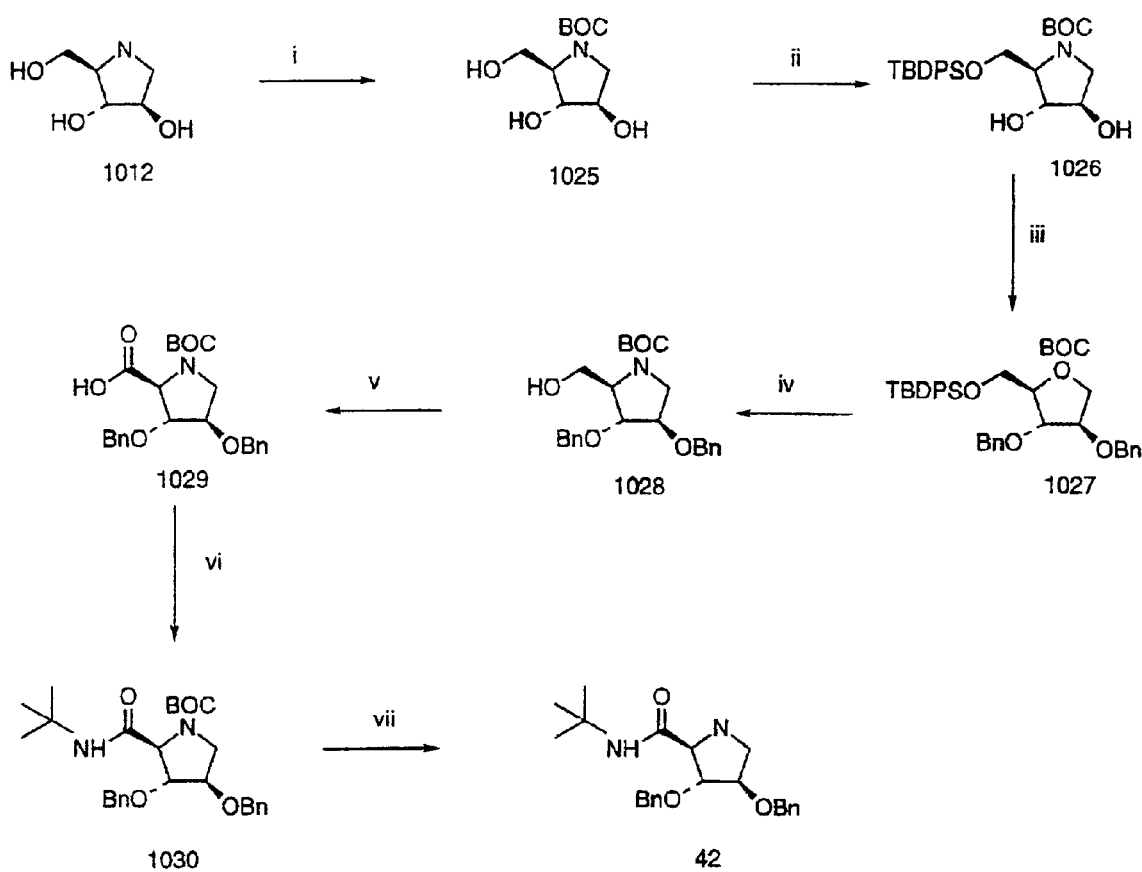
FIG. 19 illustrates the synthesis of pyrolidine 42 with the following steps: (i) BOC-ON, methylene chloride; (ii) TBDPSCl, Et$_3$N, DMF; (iii) Benzyl bromide, sodium hydride, DMF; (iv) TBAF, THF; (v) 1.5 M H$_2$SO$_4$, CrO$_3$, acetone; (vi) H$_2$N$^t$Bu, EDC, methylene chloride; (vii) H$_2$, Pd(OH)$_2$ on Carbon, MeOH.

Synthesis of compound 1022 as illustrated in FIG. 19: The substrate was dissolved in THF and cooled to 0° C. TBAF (1.0 M solution in THF) was added (1.05 eq.) and the reaction monitored by TLC. After 30 min. at 0° C., the reaction was complete and the solvent was evaporated under reduced pressure. The crude material was applied to a short column of silica gel and eluted to give the product.

Synthesis of compound 1023 as illustrated in FIG. 18: Compound 1022 was disolved in 0.10 Molar solution of acetone and then 1.5 M sulfuric acid was added at 0° C. Next chromium (VI) oxide (1.1 equivalents; Aldrich) was added and the mixture was allowed to stir for 2 hours. The reaction is worked up by adding EtOAc and washed with sat. NaHCO$_3$ solution, then with brine, dried over MgSO$_4$ and concentrated in vacuo to give an oil. The mother liquor is then chromatographed to give the product 1023.

Synthesis of compound 1024 as illustrated in FIG. 18: The substrate 1023 (70 mg, 0.213 mmol), is dissolved in dry methylene chloride (3 mL). EDC, 1-(3-dimethylaminopropyl)-3-ethylcarbodiimide, (43 mg, 0.224 mmol) is added and the mixture is stirred for 30 minutes at room temperature. tert-butyl amine (73 mg, 0.255 mmol) is added and the reaction stirred for 18 hours. The reaction mixture is diluted with ethyl acetate (20 mL) and added to saturated ammonium chloride (30 mL). The aqueous phase is extracted with ethyl acetate (3×10 mL). The combined organic phases are then washed with water (2×5 mL), 1 N HCl$_{(aq.)}$ (5 mL) saturated sodium bicarbonate solution$_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired coupled product.

Synthesis of compound 40 as illustrated in FIG. 18: CBZ-protected amine 1024 (0.092 mmol) was dissolved in MeOH (2 mL) and 20% palladium hydroxide on carbon (10 mg) was added and the suspension was stirred vigorously under a balloon of hydrogen at ambient temperature. After 5 min., TLC indicated that the reaction was complete. The suspension was filtered through a pad of celite and concentrated in vacuo to yield product compound 40.

Synthesis of compound 1025 as illustrated in FIG. 19: Compound 1025 (290 mg, 1.09 mmol; Aldrich) in methylene chloride (0.10 Molar) at 0° C. under argon was added BOC-ON (1.1 equivalents; Aldrich) and the mixture was stirred at 0° C. for 20 min. and then quenched with a few drops of water. Saturated ammonium chloride solution was added (10 mL) and the aqueous layer was washed with ethyl ether. The aqueous layer was then neutralized with saturated sodium bicarbonate solution, extracted with ethyl acetate (3×20 mL), dried over MgSO$_4$, and concentrated to afford a yellow oil. The mother liquor is then chromatographed to give the product 1025.

Synthesis of compound 1026 as illustrated in FIG. 19: To a solution of substrate 1025 (0.5 mmol) in anhydrous DMF (5 mL) was added TBDPSCl (1.05 eq: Aldrich), Et$_3$N (1.1 eq), and a catalytic amount of imidazole. The solution was stirred at ambient temperature for 15 hr and then was partitioned between EtQAc (60 mL) and H$_2$O (30 mL). The organic layer was then washed with sat'd NH$_4$Cl$_{(aq.)}$ solution (2×30 mL), water (30 mL), brine (30 mL), dried over MgSO$_4$, and concentrated in vacuo to yield product. The mother liquor is then chromatographed to give the product 1026.

Synthesis of compound 1027 as illustrated in FIG. 19: To an ice-cooled solution of substrate (0.2 mmol) in anhydrous DMF (2 mL) under argon was added NaH (60% disp. in mineral oil) (2.2 eq.). The mixture was allowed to stir for 20 min., and then methyl iodide or benzyl bromide (1.1 eq.) was added. The mixture was allowed to stir for 1 hr at 0° C. and then quenched with a few drops of water. Saturated NaHCO$_3$ solution was added (10 mL) and the aqueous layer was washed with ethyl ether. The aqueous layer was then acidified to pH 2 with 1N HCl, extracted with ethyl acetate (3×20 mL), dried over MgSO$_4$, and concentrated to afford product. The mother liquor is then chromatographed to give the product 1027.

Synthesis of compound 1028 as illustrated in FIG. 19: The substrate was dissolved in THF and cooled to 0° C. TBAF (1.0 M solution in THF) was added (1.05 eq.) and the reaction monitored by TLC. After 30 min. at 0° C., the reaction was complete and the solvent was evaporated under reduced pressure. The crude material was applied to a short column of silica gel and eluted to give the product.

Synthesis of compound 1029 as illustrated in FIG. 19: Compound 1028 was disolved in 0.10 Molar solution of acetone and then 1.5 M sulfuric acid was added at 0° C. Next chromium (VI) oxide (1.1 equivalents; Aldrich) was added and the mixture was allowed to stir for 2 hours. The reaction is worked up by adding EtOAc and washed with sat. NaHCO$_3$ solution, then with brine, dried over MgSO$_4$ and concentrated in vacuo to give an oil. The mother liquor is then chromatographed to give the product 1029.

Synthesis of compound 1030 as illustrated in FIG. 19: The substrate 1029 (70 mg, 0.213 mmol), is dissolved in dry methylene chloride (3 mL). EDC, 1-(3-dimethylaminopropyl)-3-ethylcarbodiimide, (43 mg, 0.224 mmol) is added and the mixture is stirred for 30 minutes at room temperature. tert-butyl amine (73 mg, 0.255 mmol) is added and the reaction stirred for 18 hours. The reaction mixture is diluted with ethyl acetate (20 mL) and added to saturated ammonium chloride (30 mL). The aqueous phase is extracted with ethyl acetate (3×10 mL). The combined organic phases are then washed with water (2×5 mL), 1 N HCl$_{(aq.)}$ (5 mL), saturated sodium bicarbonate solution$_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired coupled product.

Synthesis of compound 42 as illustrated in FIG. 19: CBZ-protected amine 1030 (0.092 mmol) was dissolved in MeOH (2 mL) and 20% palladium hydroxide on carbon (10 mg) was added and the suspension was stirred vigorously under a balloon of hydrogen at ambient temperature. After 5 min., TLC indicated that the reaction was complete. The suspension was filtered through a pad of celite and concentrated in vacuo to yield product compound 42.

Figure 20:
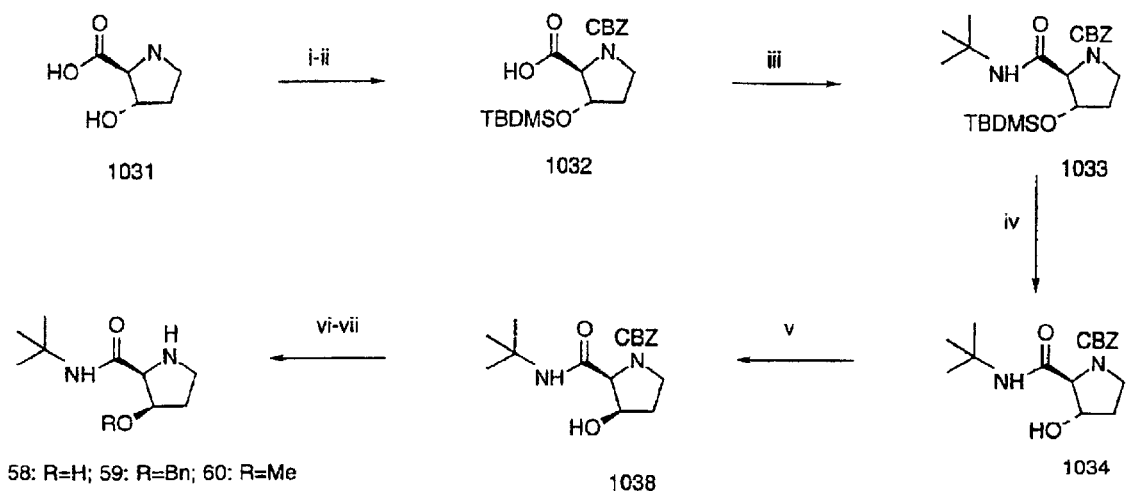
FIG. 20 illustrates the synthesis of pyrolidines 58, 59, 60, 64, 65, and 66 with the following steps: For compounds 58, 59, 60: (i) CBZ-Cl, methylene chloride; (ii) TBDMSCl, Et$_3$N, DMF; (iii) H$_2$N$^t$Bu, EDC, methylene chloride; (iv) TBAF, THF; (v) "Mitsunobu" procedure: PPh$_3$, DEAD (diethylazaodicarboxylate), ClCH$_2$CO$_2$H, then water, pyridine to pH 6.7; (vi) Benzyl bromide for 59 or methyl iodide for 60, sodium hydride, DMF (omit this step for 58) (vii) H$_2$, Pd(OH)$_2$ on Carbon, MeOH. For compounds 64, 65, and 66 same conditions as above without step (v) "Mitsunobu" procedure.
Figure 20:
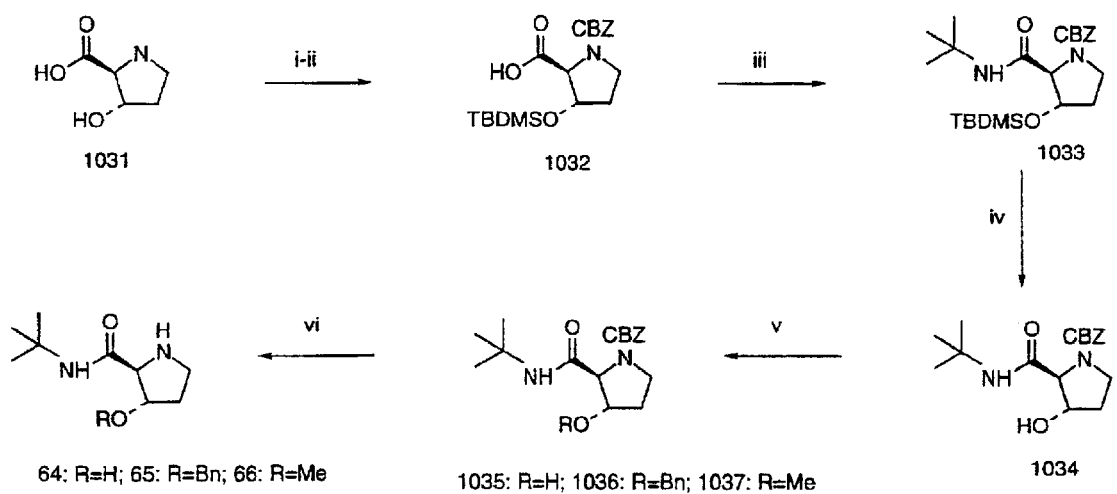

Synthesis of compound 1032 as illustrated in FIG. 20: Compound 1031 (290 mg, 1.09 mmol; Aldrich) in methylene chloride (0.10 Molar) at 0° C. under argon was added CBZ-CL (1.1 equivalents; Aldrich) and the mixture was stirred at 0° C. for 20 min. and then quenched with a few drops of water. Saturated ammonium chloride solution was added (10 mL) and the aqueous layer was washed with ethyl ether. The aqueous layer was then neutralized with saturated sodium bicarbonate solution, extracted with ethyl acetate (3×20 mL), dried over MgSO$_4$, and concentrated to afford a yellow oil. The mother liquor is then chromatographed to give the product. Next, to a solution of substrate (0.5 mmol) in anhydrous DMF (5 mL) was added TBDMSCl (1.05 eq: Aldrich), Et$_3$N (1.1 eq), and a catalytic amount of imidazole. The solution was stirred at ambient temperature for 15 hr and then was partitioned between EtOAc (60 mL) and H$_2$O (30 mL). The organic layer was then washed with sat'd NH$_4$Cl $_{(aq.)}$ solution (2×30 mL), water (30 mL), brine (30 mL), dried over MgSO$_4$, and concentrated in vacuo to yield product. The mother liquor is then chromatographed to give the product 1032.

Synthesis of compound 1033 as illustrated in FIG. 20: The substrate 1032 (70 mg, 0.213 mmol), is dissolved in dry methylene chloride (3 mL). EDC, 1-(3-dimethylaminopropyl)-3-ethylcarbodiimide, (43 mg, 0.224 mmol) is added and the mixture is stirred for 30 minutes at room temperature. tert-butyl amine (73 mg, 0.255 mmol) is added and the reaction stirred for 18 hours. The reaction mixture is diluted with ethyl acetate (20 mL) and added to saturated ammonium chloride (30 mL). The aqueous phase is extracted with ethyl acetate (3×10 mL). The combined organic phases are then washed with water (2×5 mL), 1 N HCl $_{(aq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired coupled product.

Synthesis of compound 1034 as illustrated in FIG. 20: The substrate was dissolved in THF and cooled to 0° C. TBAF (1.0 M solution in THF) was added (1.05 eq.) and the reaction monitored by TLC. After 30 min. at 0° C., the reaction was complete and the solvent was evaporated under reduced pressure. The crude material was applied to a short column of silica gel and eluted to give the product.

Synthesis of compound 1038 as illustrated in FIG. 20: Synthesis was carried out via a Mitsunobu inversion using identical conditions as published in Saiah et al. *Tet. Lett.* 1992, 33, 4317; Johnson et al *J. Am. Chem. Soc.* 1964, 86, 118. The reaction mixture is then worked up by dilution with ethyl acetate (20 mL) and is added to saturated ammonium chloride (30 mL). The aqueous phase is extracted with ethyl acetate (3×10 mL). The combined organic phases are then washed with water (2×5 mL), 1 N HCl $_{(aq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired coupled product.

Synthesis of compound 58 as illustrated in FIG. 20: To the CBZ-protected amine (0.092 mmol) was dissolved in MeOH (2 mL) and 20% palladium hydroxide on carbon (10 mg) was added and the suspension was stirred vigorously under a balloon of hydrogen at ambient temperature. After 5 min., TLC indicated that the reaction was complete. The suspension was filtered through a pad of celite and concentrated in vacuo to yield product.

Synthesis of compound 59 as illustrated in FIG. 20: CBZ-protected amine 1038 (0.092 mmol) was dissolved in MeOH (2 mL) and 20% palladium hydroxide on carbon (10 mg) was added and the suspension was stirred vigorously under a balloon of hydrogen at ambient temperature. After 5 min., TLC indicated that the reaction was complete. The suspension was filtered through a pad of celite and concentrated in vacuo to yield product. Next, to an ice-cooled solution of substrate (0.2 mmol) in anhydrous DMF (2 mL) under argon was added NaH (60% disp. in mineral oil) (2.2 eq.). The mixture was allowed to stir for 20 min., and then benzyl bromide (1.1 eq.) was added. The mixture was allowed to stir for 1 hr at 0° C. and then quenched with a few drops of water. Saturated NaHCO$_3$ solution was added (10 mL) and the aqueous layer was washed with ethyl ether. The aqueous layer was then acidified to pH 2 with 1N HCl, extracted with ethyl acetate (3×20 mL), dried over MgSO$_4$, and concentrated to afford product. The mother liquor is then chromatographed to give the product to give 58.

Synthesis of compound 60 as illustrated in FIG. 20: To an ice-cooled solution of substrate 1038 (0.2 mmol) in anhydrous DMF (2 mL) under argon was added NaH (60% disp. in mineral oil) (2.2 eq.). The mixture was allowed to stir for 20 min., and then methyl iodide (1.1 eq.) was added. The mixture was allowed to stir for 1 hr at 0° C. and then quenched with a few drops of water. Saturated NaHCO$_3$ solution was added (10 mL) and the aqueous layer was washed with ethyl ether. The aqueous layer was then acidified to pH 2 with 1N HCl, extracted with ethyl acetate (3×20 mL), dried over MgSO$_4$, and concentrated to afford product. The mother liquor is then chromatographed to give the product to give intermediate product. Next, to the CBZ-protected amine (0.092 mmol) was dissolved in MeOH (2 mL) and 20% palladium hydroxide on carbon (10 mg) was added and the suspension was stirred vigorously under a balloon of hydrogen at ambient temperature. After 5 min., TLC indicated that the reaction was complete. The suspension was filtered through a pad of celite and concentrated in vacuo to yield product.

Synthesis of compound 64 as illustrated in FIG. 20: To the CBZ-protected amine 1034 (0.092 mmol) was dissolved in MeOH (2 mL) and 20% palladium hydroxide on carbon (10 mg) was added and the suspension was stirred vigorously under a balloon of hydrogen at ambient temperature. After 5 min., TLC indicated that the reaction was complete. The suspension was filtered through a pad of celite and concentrated in vacuo to yield product.

Synthesis of compound 65 as illustrated in FIG. 20: CBZ-protected amine 1034 (0.092 mmol) was dissolved in MeOH (2 mL) and 20% palladium hydroxide on carbon (10 mg) was added and the suspension was stirred vigorously under a balloon of hydrogen at ambient temperature. After 5 min., TLC indicated that the reaction was complete. The suspension was filtered through a pad of celite and concentrated in vacuo to yield product. Next, to an ice-cooled solution of substrate (0.2 mmol) in anhydrous DMF (2 mL)

under argon was added NaH (60% disp. in mineral oil) (2.2 eq.). The mixture was allowed to stir for 20 min., and then benzyl bromide (1.1 eq.) was added. The mixture was allowed to stir for 1 hr at 0° C. and then quenched with a few drops of water. Saturated NaHCO$_3$ solution was added (10 mL) and the aqueous layer was washed with ethyl ether. The aqueous layer was then acidified to pH 2 with 1N HCl, extracted with ethyl acetate (3×20 mL), dried over MgSO$_4$, and concentrated to afford product. The mother liquor is then chromatographed to give the product to give 65.

Synthesis of compound 66 as illustrated in FIG. 20: To an ice-cooled solution of substrate 1034 (0.2 mmol) in anhydrous DMF (2 mL) under argon was added NaH (60% disp. in mineral oil) (2.2 eq.). The mixture was allowed to stir for 20 min., and then methyl iodide (1.1 eq.) was added. The mixture was allowed to stir for 1 hr at 0° C. and then quenched with a few drops of water. Saturated NaHCO$_3$ solution was added (10 mL) and the aqueous layer was washed with ethyl ether. The aqueous layer was then acidified to pH 2 with 1N HCl, extracted with ethyl acetate (3×20 mL), dried over MgSO$_4$, and concentrated to afford product. The mother liquor is then chromatographed to give the product to give intermediate product. Next, to the CBZ-protected amine (0.092 mmol) was dissolved in MeOH (2 mL) and 20% palladium hydroxide on carbon (10 mg) added and the suspension was stirred vigorously under a balloon of hydrogen at ambient temperature. After 5 min., TLC indicated that the reaction was complete. The suspension was filtered through a pad of celite and concentrated in vacuo to yield product.

Figure 21:
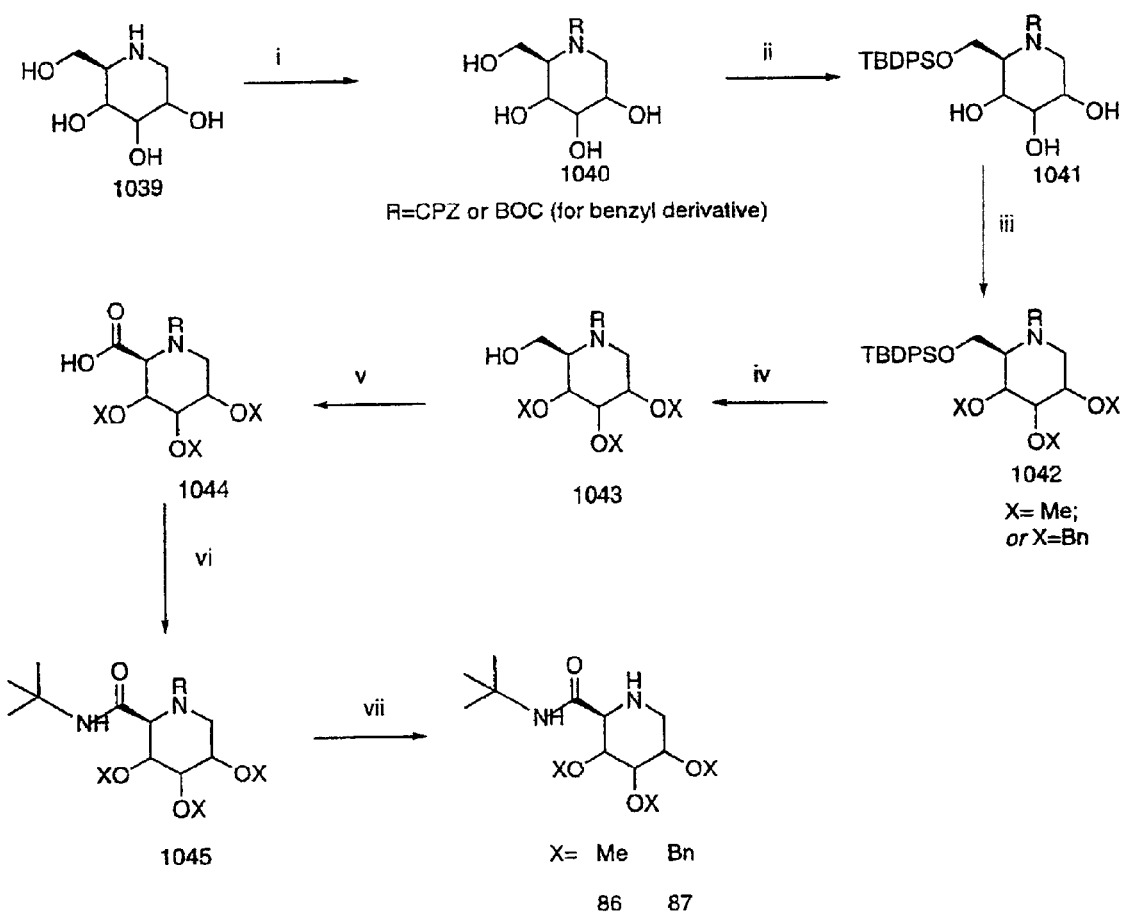
FIG. 21 illustrates the synthesis of piperidines 86 and 87 with the following steps: (i) CBZ-Cl or BOC-ON, methylene chloride; (ii) TBDPSCl, Et$_3$N, DMF; (iii) Benzyl bromide for 87 or methyl iodide for 86, sodium hydride, DMF (iv) TBAF, THF; (v) 1.5 M H$_2$SO$_4$, CrO$_3$, acetone; (vi) H$_2$N$^t$Bu, EDC, methylene chloride; (vii) H$_2$, Pd(OH)$_2$ on Carbon, MeOH.

Synthesis of compound 1040 as illustrated in FIG. 21: Piperidine compound 1039 (290 mg, 1.09 mmol; Aldrich) in methylene chloride (0.10 Molar) at 0° C. under argon was added CBZ-Cl (1.1 equivalents; Aldrich) and the mixture was stirred at 0° C. for 20 min. and then quenched with a few drops of water. Saturated ammonium chloride solution was added (10 mL) and the aqueous layer was washed with ethyl ether. The aqueous layer was then neutralized with saturated sodium bicarbonate solution, extracted with ethyl acetate (3×20 mL), dried over MgSO$_4$, and concentrated to afford a yellow oil. The mother liquor is then chromatographed to give the product.

Synthesis of Compound 1041 as Illustrated in FIG. 21:

To a solution of substrate (0.5 mmol) in anhydrous DMF (5 mL) was added TBDPSCl (1.05 eq: Aldrich), Et$_3$N (1.1 eq), and a catalytic amount of imidazole. The solution was stirred at ambient temperature for 15 hr and then was partitioned between EtOAc (60 mL) and H$_2$O (30 mL). The organic layer was then washed with sat'd NH$_4$Cl $_{(aq.)}$ solution (2×30 mL), water (30 mL), brine (30 mL), dried over MgSO$_4$, and concentrated in vacuo to yield product. The mother liquor is then chromatographed to give the product 1041.

Synthesis of compound 1042 as illustrated in FIG. 21: To an ice-cooled solution of substrate (0.2 mmol) in anhydrous DMF (2 mL) under argon was added NaH (60% disp. in mineral oil) (2.2 eq.). The mixture was allowed to stir for 20 min., and then methyl iodide or benzyl bromide (1.1 eq.) was added. The mixture was allowed to stir for 1 hr at 0° C. and then quenched with a few drops of water. Saturated NaHCO$_3$ solution was added (10 mL) and the aqueous layer was washed with ethyl ether. The aqueous layer was then acidified to pH 2 with 1N HCl, extracted with ethyl acetate (3×20 mL), dried over MgSO$_4$, and concentrated to afford product. The mother liquor is then chromatographed to give the product 1042.

Synthesis of compound 1043 as illustrated in FIG. 21: The substrate was dissolved in THF and cooled to 0° C. TBAF (1.0 M solution in THF) was added (1.05 eq.) and the reaction monitored by TLC. After 30 min. at 0° C., the reaction was complete and the solvent was evaporated under reduced pressure. The crude material was applied to a short column of silica gel and eluted to give the product.

Synthesis of compound 1044 as illustrated in FIG. 21: Compound 1043 was disolved in 0.10 Molar solution of acetone and then 1.5 M sulfuric acid was added at 0° C. Next chromium (VI) oxide (1.1 equivalents; Aldrich) was added and the mixture was allowed to stir for 2 hours. The reaction is worked up by adding EtOAc and washed with sat. NaHCO$_3$ solution, then with brine, dried over MgSO$_4$ and concentrated in vacuo to give an oil. The mother liquor is then chromatographed to give the product 1044.

Synthesis of compound 1045 as illustrated in FIG. 21: The substrate 1044 (70 mg, 0.213 mmol), is dissolved in dry methylene chloride (3 mL). EDC, 1-(3-dimethylaminopropyl)-3-ethylcarbodiimide, (43 mg, 0.224 mmol) is added and the mixture is stirred for 30 minutes at room temperature. tert-butyl amine (73 mg, 0.255 mmol) is added and the reaction stirred for hours. The reaction mixture is diluted with ethyl acetate (20 mL) and added to saturated ammonium chloride (30 mL). The aqueous phase is extracted with ethyl acetate (3×10 mL). The combined organic phases are then washed with water (2×5 mL), 1 N HCl $_{(aq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired coupled product.

Synthesis of compounds 86 or 87 as illustrated in FIG. 21: CBZ-protected amine 1045 (0.092 mmol) was dissolved in MeOH (2 mL) and 20% palladium hydroxide on carbon (10 mg) was added and the suspension was stirred vigorously under a balloon of hydrogen at ambient temperature. After 5 min., TLC indicated that the reaction was complete. The suspension was filtered through a pad of celite and concentrated in vacuo to yield product compound 86 or 87, depending on whether benzyl or methyl.

Figure 22:
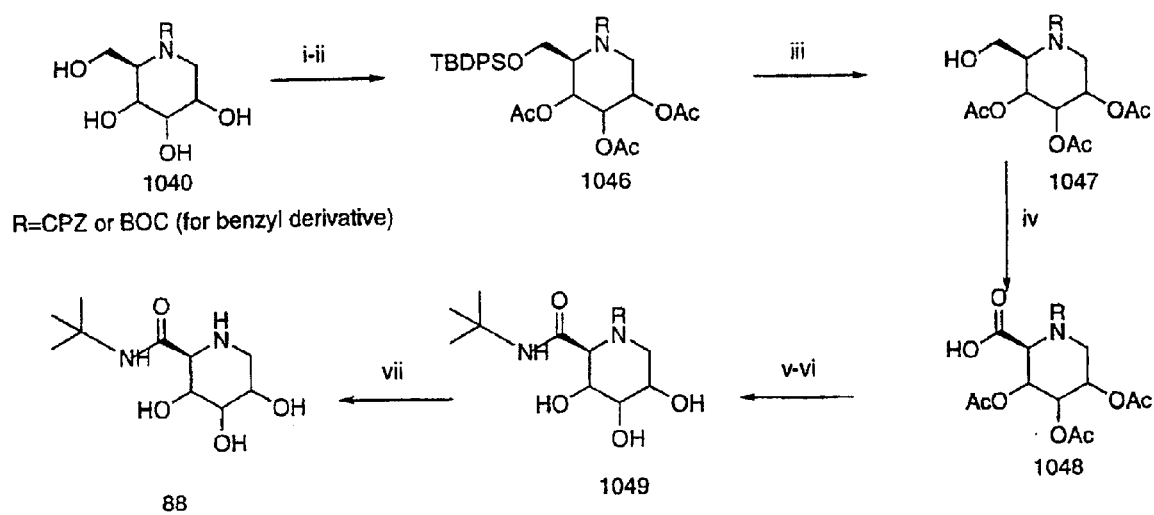
FIG. 22 illustrates the synthesis of piperidines 85 with the following steps: (i) CBZ-Cl or BOC-ON, methylene chloride; TBDPSCl, Et$_3$N, DMF; (ii) acetic anhydride, triethylamine, DMF (iii) TBAF, THF; (iv) 1.5 M H$_2$SO$_4$, CrO$_3$, acetone; (v) H$_2$N$^t$Bu, EDC, methylene chloride; (vi) NaOMe, MeOH; (vii) H$_2$, Pd(OH)$_2$ on Carbon, MeOH.
Figure 23:
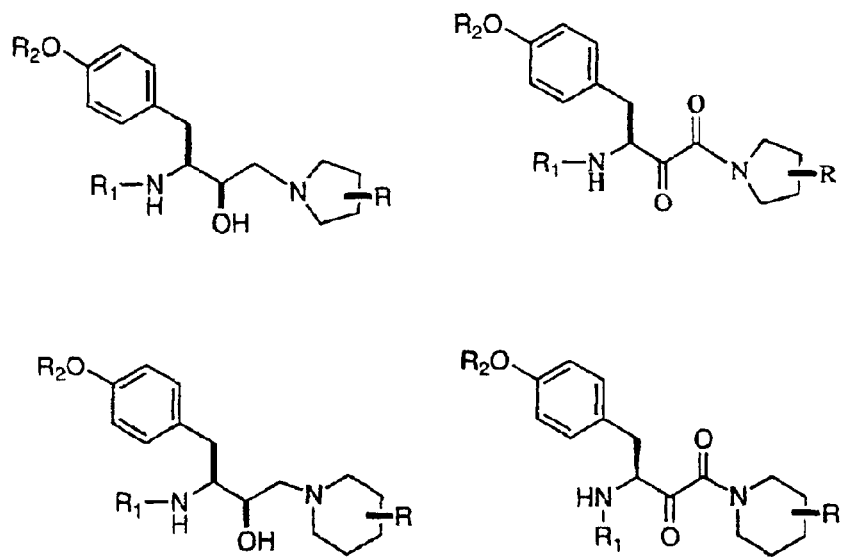
FIG. 23 illustrates tyrosine derivatives of pyrolidine or piperidine containing α-ketoamide and hydroxylethylamine core structures to probe for FIV and HIV protease selectivity.
Figure 24:
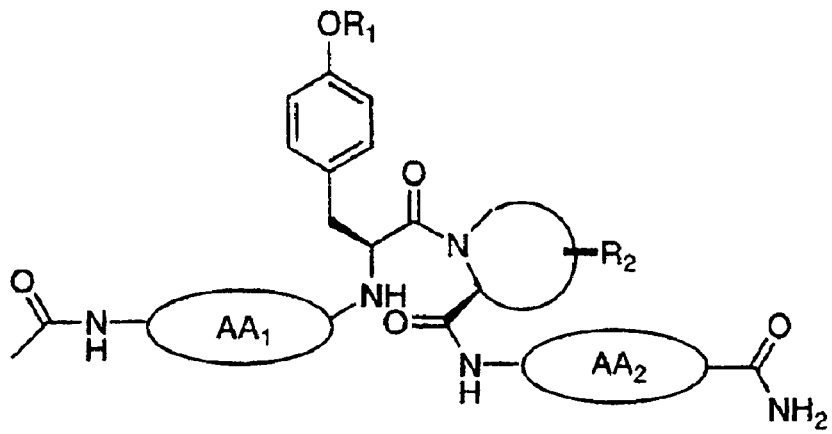
FIG. 24 illustrates targeted variable sites on the core structure which can be assessed using a combinatorial approach. Di-/tri-/tetrameric substrates for HIV-PR and FIV-PR are possible. Candidate molecules display activity by cleavage of either HIV-PR or FIV-PR protease. The candidate molecules are subsequently rederivatized via replacement of the scissile amide bond to an α-keto amide or hydroxyethyl amine, affording further potential inhibitors. The synthetic strategy involves solution phase coupling of the added residues (standard coupling conditions, EDC HOBT, $CH_2Cl_2$ or DMF) to afford di-/tri-/tetra peptides. Simple acidic and basic washes afford the desired peptides cleanly, with no purification necessary. Compounds are then dissolved in a minimal amount of DMSO and added to buffer solution, arranged in 96-well micro-titer plates. Addition of the enzyme and subsequent mass spectral analysis identifies the cleaved substrates as hits. These molecules are then rederivatized with an α-keto amide or hydroxyethyl amine core unit and tested for inhibitory activity.
Figure 24:
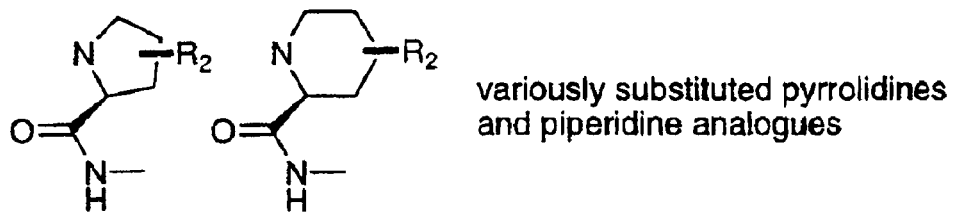
Figure 25:
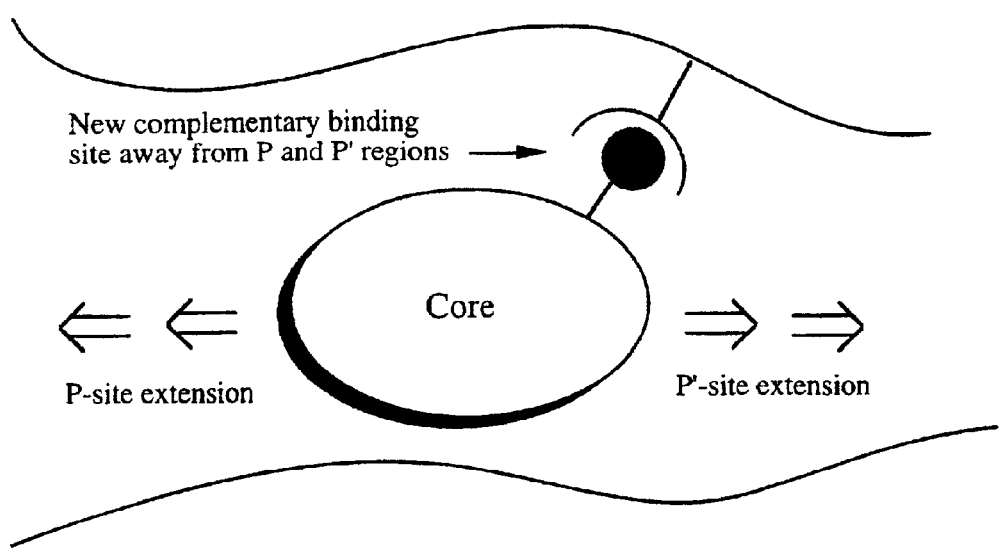
FIG. 25 illustrates the creation of non-linear protease inhibitors using the up and down search for new complementary binding sites attached to a designed mechanism-based core structure.

Synthesis of compounds 1046 as illustrated in FIG. 22: Piperidine compound 1041 (290 mg, 1.09 mmol; Aldrich) in methylene chloride (0.10 Molar) at 0° C. under argon was added acetic anhydride (3.3 equivalents; Aldrich), triethyl amine (3.3 equivalents) and the mixture was stirred at 0° C. for 20 min. and then quenched with a few drops of water. Saturated ammonium chloride solution was added (10 mL) and the aqueous layer was washed with ethyl ether. The aqueous layer was then neutralized with saturated sodium bicarbonate solution, extracted with ethyl acetate (3×20 mL), dried over MgSO$_4$, and concentrated to afford a yellow oil. The mother liquor is then chromatographed to give the product.

Synthesis of compound 1047 as illustrated in FIG. 22: The substrate was dissolved in THF and cooled to 0° C. TBAF (1.0 M solution in THF) was added (1.05 eq.) and the reaction monitored by TLC. After 30 min. at 0° C., the reaction was complete and the solvent was evaporated under reduced pressure. The crude material was applied to a short column of silica gel and eluted to give the product.

Synthesis of compound 1048 as illustrated in FIG. 22: Compound 1047 was disolved in 0.10 Molar solution of acetone and then 1.5 M sulfuric acid was added at 0° C. Next chromium (VI) oxide (1.1 equivalents; Aldrich) was added and the mixture was allowed to stir for 2 hours. The reaction is worked up by adding EtOAc and washed with sat. NaHCO$_3$ solution, then with brine, dried over MgSO$_4$ and concentrated in vacuo to give an oil. The mother liquor is then chromatographed to give the product.

Synthesis of compound 1049 as illustrated in FIG. 22: The substrate 1048 (70 mg, 0.213 mmol), is dissolved in dry methylene chloride (3 mL). EDC, 1-(3-dimethylaminopropyl)-3-ethylcarbodiimide, (43 mg, 0.224 mmol) is added and the mixture is stirred for 30 minutes at room temperature. tert-butyl amine (73 mg, 0.255 mmol) is added and the reaction stirred for 18 hours. The reaction mixture is diluted with ethyl acetate (20 mL) and added to saturated ammonium chloride (30 mL). The aqueous phase is extracted with ethyl acetate (3×10 mL). The combined organic phases are then washed with water (2×5 mL), 1 N HCl $_{(aq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired coupled product. Compound is then redissolved in dry methanol (3 mL) and sodium methoxide (0.30 equivalents added and the mixture is stirred for 18 hours at reflux. The is concentrated in vacuo to give the crude product. Flash chromatography, eluting with 1:1 ethyl acetate/hexane gives the desired product 1049.

Synthesis of compounds 88 as illustrated in FIG. 22: CBZ-protected amine 1049 (0.092 mmol) was dissolved in MeOH (2 mL) and 20% palladium hydroxide on carbon (10 mg) was added and the suspension was stirred vigorously under a balloon of hydrogen at ambient temperature. After 5 min., TLC indicated that the reaction was complete. The suspension was filtered through a pad of celite and concentrated in vacuo to yield product compound 88.

Figure 27:
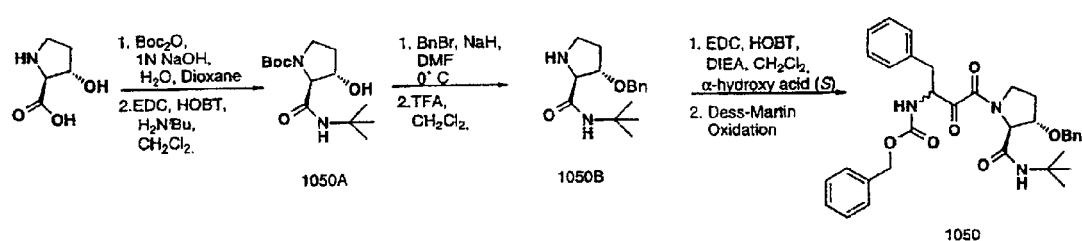
FIG. 27 illustrates the synthesis of α-ketoamide compound 1050 with the indicated substrate and reagents.

Synthesis of Compound 1050A as illustrated in FIG. 27.

Step 1) To a solution of commerically available trans-3-hydroxyproline is added 1.1 equivalents BOC-ON (Aldrich) in a 1:1 v/v solution water/dioxanes and NaOH (1N solution) and stirred at 0° C. for 12 hours. The combined organic phases are then washed with water (2×5 mL), 1 N HCl $_{(aq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired protected product. Step 2) As illustrated in FIG. 27 the substrate (70 mg, 0.213 mmol; vida supra), is dissolved in dry methylene chloride (3 mL). EDC, 1-(3-dimethylaminopropyl)-3-ethylcarbodiimide, (43 mg, 0.224 mmol) is added and the mixture is stirred for 30 minutes at room temperature. tert-butyl amine (73 mg, 0.255 mmol) is added and the reaction stirred for 18 hours. The reaction mixture is diluted with ethyl acetate (20 mL) and added to saturated ammonium chloride (30 mL). The aqueous phase is extracted with ethyl acetate (3×10 mL). The combined organic phases are then washed with water (2×5 mL), 1 N HCl $_{(aq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired product 1050A.

Synthesis of Compound 1050B as illustrated in FIG. 27.

Step 1) To an ice-cooled solution of N-(benzyloxycarbonyl)-cis-3'-hydroxyproline (290 mg, 1.09 mmol; vida supra) in anhydrous DMF (2 mL) under argon was added NaH (60% disp. in mineral oil) (96 mg, 2.40 mmol, 2.2 eq.). The mixture was allowed to stir for 20 min., and then benzyl bromide (0.14 mL, 1.20 mmol, 1.1 eq.) was added. The mixture was allowed to stir for 1 hr at 0° C. and then quenched with a few drops of water. Saturated NaHCO$_3$ solution was added (10 mL) and the aqueous layer was washed with ethyl ether. The aqueous layer was then acidified to pH 2 with 1N Hcl, extracted with ethyl acetate (3×20 mL), dried over MgSO$_4$, and concentrated to afford a yellow oil. (205 mg, 53%) The crude material was carried on without purification.

Step 2) To the crude yellow oil (0.982 mmol) was added TBAF (1M in THF) (1.9 mL, 1.9 mmol, 2 eq.), and the solution was stirred 2 hr at ambient temperature. The solution was concentrated in vacuo and immediately applied to a short silica gel column, eluting with 33% ethyl acetate in hexanes. The product was isolated as a white foam (443 mg, 95%).

Synthesis of Compound 1050 as illustrated in FIG. 27.

As illustrated in FIG. 13, steps i–ii, the substrate 11 (70 mg, 0.213 mmol), is dissolved in dry DMF (3 mL). HOBT, 1-hydroxybenzotriazole hydrate (31 mg, 0.22 mmol), EDC, 1-(3-dimethylaminopropyl)-3-ethylcarbodiimide, (43 mg, 0.224 mmol), DIEA, diisopropylethylamine, (122 µl, 0.703 mmol) are added and the mixture is stirred for 30 minutes at room temperature. The secondary amine 1050B (73 mg, 0.255 mmol) is added and the reaction stirred for 18 hours. The reaction mixture is diluted with ethyl acetate (20 mL) and added to saturated ammonium chloride (30 mL). The aqueous phase is extracted with ethyl acetate (3×10 mL). The combined organic phases are then washed with water (2×5 mL), 1 N HCl $_{(aq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired coupled product which is directly carried on to the next step for oxidation of the secondary alcohol as follows. The secondary alcohol (21 mg, 0.044 mmol) is dissolved in dry CH$_2$Cl$_2$ (2 mL), and Dess-Martin periodinane (26 mg, 0.088 mmol) added. The reaction mixture is stirred at ambient temperature for 24 hours, then diluted with ethyl acetate (10 mL) and quenched by addition of saturated sodium bicarbonate $_{(aq.)}$ (5 mL) and sodium thiosulfate. The aqueous phase is extracted with ethyl acetate (3×20 mL). The combined organic extracts washed with water (10 mL), brine (10 mL), dried (MgSO$_4$) and concentrated in vacuo to give the crude product. Flash chromatography eluting with 30% ethyl acetate in hexane gives the respective product 1050 as a 3:1 mixture of diastereomers (colorless oil) (20 mg, 95%) as a colorless oil.

Synthesis of N-benzyl-cis-and trans-2,5-dicarb-methoxypyrrolidines Compound 1051A (FIG. 28): N-benzyl-cis-and trans-2,5-dicarbmethoxypyrrolidine were synthesized according to the procedure of Cignarella and Nathansohn (Cignarella, G. Nathansohn, G., JOC, 1961, 26, 1500.) The two diastereomers (cis and trans) were separated by flash chromatography (1:9 EA/H to 1:4 EA/H). Analytical data matched that reported by Kemp and Curran (Kemp, D. S., Curran, T. P. JOC, 1988, 53, 5729).

Synthesis of Cis-(2S,5R)-dicarbmethoxypyrollidine (Step 1, intermediate to compound 1051B (FIG. 28)): N-benzyl-cis-(2S, 5R)-dicarbmethoxypyrrolidine (1.0 equivalents) was dissolved in MeOH (0.10 M) and a catalytic amount of 10% palladium on carbon was added. The mixture was stirred vigorously under a balloon of hydrogen until TLC indicated that the reaction was complete. Filtration and concentration afforded a clean product.

Synthesis of N-(benzyloxycarbonyl)-dimethyl pyrrolidine-(2S,5R)-dicarboxylate (Step 2, intermediate to compound 1051B (FIG. 28)): To the crude substrate dimethylpyrrolidine-2,5-dicarboxylate (869 mg, 4.06 mmol) was added water (20 ml). The solution was cooled to 0° C. in an ice bath, and 0.3 M K$_2$CO$_3$ was added dropwise until pH=9. CbzCl (1.1 eq, 4.5 mmol) was added and the mixture was stirred 30 min at 0° C. and 30 min at ambient temperature. The aqueous layer was extracted with EtOAc (3×20 mL) and was dried over $MgSO_4$, filtered, and concentrated under reduced pressure to yield a yellow oil. Purification by flash chromatography (1:3 EA/H) yielded a clear oil. (1.2 g) Rf (1:1 EA/H)=0.48.

Synthesis of N-(benzyloxycarbonyl)-cis-(2S,5R)-dimethanol pyrrolidine compound 1051B: The substrate N-(benzyloxycarbonyl)-dimethylpyrrolidine-(2S, 5R)-dicarboxylate (766 mg, 2.3 mmol) was dissolved in anhydrous THF (15 mL) and the solution was cooled to −78° C. in a dry ice/acetone bath. To this solution was added DIBAL-H (1.5 M in toluene) (14.2 mL, 9.6 mmol, 4.2 eq.). The solution was allowed to stir at −78° C., and gradually warmed to 0° C. during the course of 1 hr. The reaction was then quenched with 1N HCl (a few drops), and THF removed in vacuo. The slurry was extracted with EtOAc (3×30 mL) and washed with brine (30 mL). After drying over $MgSO_4$ and concentratedin vacuo to yield a yellow oil. Flash column purification in 1:1 EA/H gave the desired diol.

Figure 26:
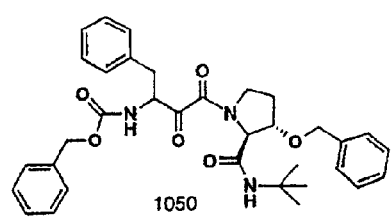
FIG. 26 illustrates various α-ketoamide and hydroxyethyl HIV protease inhibitors.
Figure 26:
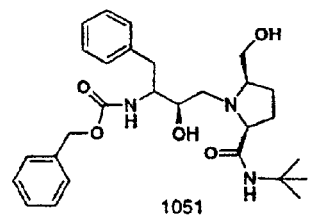
Figure 26:
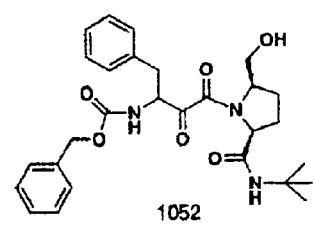
Figure 26:
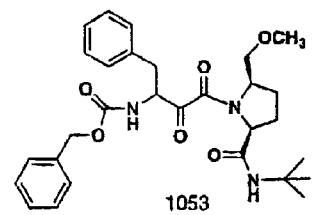
Figure 26:
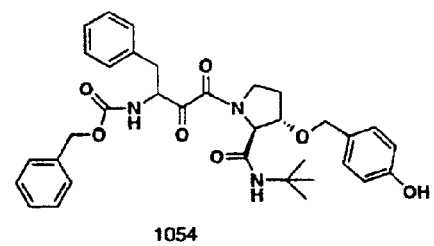
Figure 26:
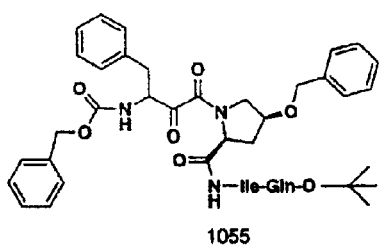
Figure 26:
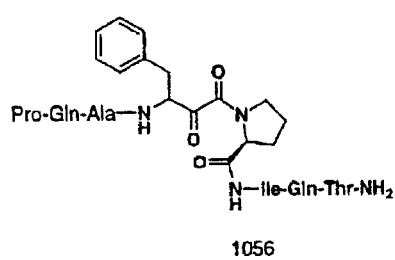
Figure 26:
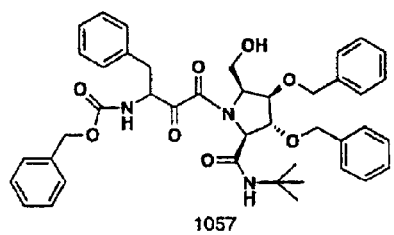
Figure 26:
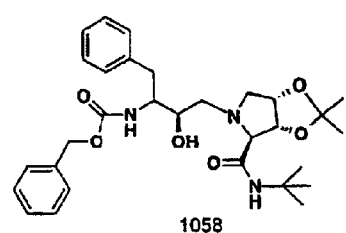

Synthesis of N-(benzyloxycarbonyl)-cis-(2S)-methanol-(5R)-(butyroxymethyl) pyrrolidine (Step 1, intermediate to compound 1051C (FIG. 26)): The substrate diol (800 mg, 3.02 mmol) was dissolved in vinyl butyrate (10 mL), and 553 mg of Lipase AK was added. The reaction was stirred slowly at ambient temperature until TLC indicated that starting material was gone. (60 hr.). The reaction mixture was diluted with $CH_2Cl_2$, filtered through Celite, and concentrated. After flash chromatography eluting with a gradient of 1:4 to 1:1 ethyl acetate in hexanes, the product was isolated as a colorless oil. (675 mg, 67% yield, 85% ee) (The enantiomeric excess was determined by conversion to the Mosher ester followed by 19F NMR analysis).

Figure 28:
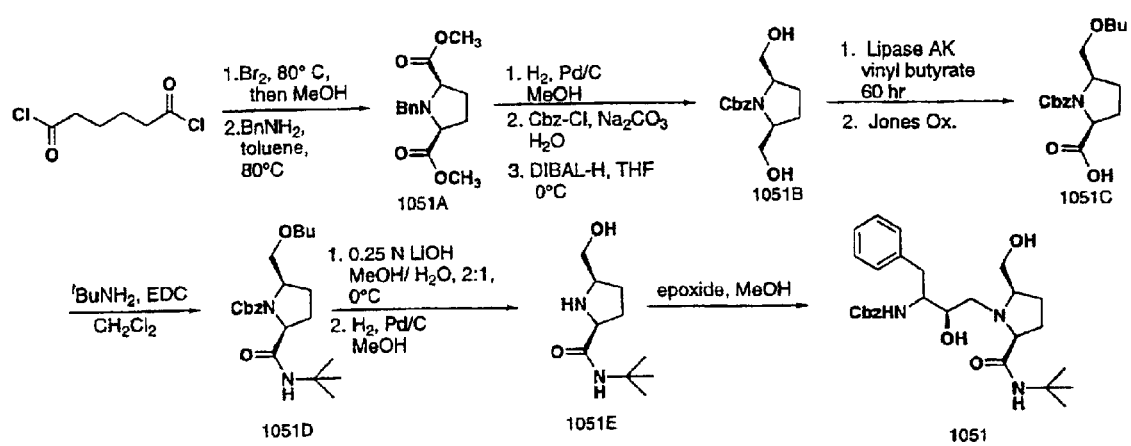
FIG. 28 illustrates the synthesis of hydroxy-ethylamine compound 1051 with the indicated substrate and reagents.

Synthesis of N-(benzyloxycarbonyl)-5-cis-(butyroxymethyl)-L-proline compound 1051C (FIG. 28). To an ice cooled solution of $CrO_3$ (6.93 mmol, 3.75 eq.) in 1.5M $H_2SO_4$ (aq.) (9 mL) was added substrate (611 mg, 1.82 mmol) in acetone (30 mL+10 mL wash). The resulting orange solution was stirred vigorously at 0° C. for 30 min., and then at ambient temperature for 7 hrs. Ethyl ether (40 mL) was then added and the organic layer was washed with brine solution (20 mL), dried over MgSO4, and concentrated in vacuo to afford crude product. This product which was subjected to a short column of silica eluting with 100% ethyl acetate to give pure product as a colorless oil (571 mg, 89%) $^1$H NMR ($CD_3OD$, 250 MHz) (peaks broadened by rotamers) δ=7.45–7.20 (5H, m), 5.25–4.90 (3H, m), 4.40–4.25 (1H, m), 4.25–4.00 (3H, m), 2.38–2.15 (2H, m), 2.15–1.73 (4H, m), 1.72–1.42 (2H, m), 1.00–0.78 (3H, m); $^{13}$C NMR ($CD_3OD$) d=175.7, 174.9, 156.4, 156.0, 137.6, 129.5, 129.3, 129.2, 129.0, 128.8, 128.5, 128.4, 68.3, 68.1, 65.4, 65.0, 61.3, 60.9, 58.6, 58.1, 36.7, 29.9, 28.9, 28.1, 19.2, 13.9; FABHRMS (NBA) m/e 350.1593 ([M+H]+ C18H23NO6 requires 350.1604.

Synthesis of N-(Benzyloxycarbonyl)-5-cis-(butyroxymethyl)-L-proline-tert-butyl amide compound 1051D (FIG. 28): The substrate i (13.9 mmol) was dissolved in dry $CH_2Cl_2$ (20 mL). HOBT, 1-hydroxybenzotriazole hydrate (2.07 g, 15.3 mmol), EDC, 1-(3-dimethylaminopropyl)-3-ethylcarbodiimide, (2.93 g, 15.3 mmol), and tert-butylamine (1.6 mL, 15.3 mmol), were added and the mixture stirred for 18 hours at ambient temperature. The reaction was diluted with ethyl acetate (100 mL), and washed with water (2×20 ml), 1 N HCl $_{(aq.)}$ (10 mL), saturated sodium bicarbonate solution $_{(aq.)}$ (10 mL), water (10 mL), brine (10 mL) and dried ($MgSO_4$) before concentration in vacuo to give the crude product. Purification by flash chromatography, eluting with 33% EtOAc in Hexane gave the title compound as a colorless oil.

Synthesis of N-(Benzyloxycarbonyl)-5-cis-hydroxymethyl-L-proline-tert-butyl amide compound 1052A (intermediate en route to compound 1051E (FIGS. 28 and 29): The substrate was dissolved in MeOH: $H_2O$ (8 mL: 4 mL) and cooled to 0° C. LiOH was added (128 mg, 5.0 eq.) and the mixture stirred for 20 min. at 0° C. The mixture was neutralized with 1N HCl and then extracted into EtOAc, dried over MgSO4, and filtered to afford product which was used in the next step without purification.

Synthesis of 5-cis-hydroxymethyl-L-proline-tert-butyl amide (compound 1051E (FIG. 28): Intermediate compound 1052A (1.0 equivalents; vida supra) was dissolved in MeOH (0.10 M) and a catalytic amount of 10% palladium on carbon was added. The mixture was stirred vigorously under a balloon of hydrogen until TLC indicated that the reaction was complete. Filtration and concentration afforded a clean product.

Synthesis of compound 1051 (FIG. 28) Using the general procedure as follows: To the pyrrolidine derivative 1051 E (20 mg, 0.091 mmol) was added dry methanol (2 mL), Cbz-phenylalanyl epoxide 21 (27 mg, 0.091 mmol, 1.0 eq; vida supra) and triethylamine (14 μL, 0.100 mmol, 1.1 eq.). The solution was refluxed for 32 h, and then concentrated in vacuo. Flash chromatography, eluting with ethyl acetate provides the desired product as a clear oil.

Synthesis of N-(Benzyloxycarbonyl)-5-cis-(tert-butyl-dimethyl-silyl-oxymethyl)-L-proline-tert-butyl amide (intermediate to compound 1052B; (FIG. 29) A solution of N-(benzyloxycarbonyl)-5-cis-hydroxymethyl-L-proline-tert-butyl amide 1052A (81 mg, 0.24 mmol; vida supra) in CH2Cl2 (3 mL) was cooled to 0° C. under an argon bed. 2,6-lutidine (0.48 mL, 56 mL, 2.0 eq.) and tert-butyldimethylsilyltriflate (88 mL, 0.38 mmol, 1.6 eq.) were added subsequently. After stirring for 1 hr at 0° C., the reaction was quenched by pouring the reaction mixture into an ice cold mixture of sat'd NaHCO3(aq)solution; H2O (5 mL: 25 mL) and extracting into CH2Cl2 (3×20 mL) The pooled organic layers were washed with 10% CuSO4(aq) solution (2×20 mL), dried over MgSO4, filtered, and evaporated under reduced pressure. Flash chromatography eluting with 25% ethyl acetate in hexanes gave the intermediate compound as a colorless oil (85 mg, 79%). Rf=0.58 (1:1 EtOAc/Hexanes). 1H NMR (CDCl3, 250 MHz) (peaks broadened by rotamers) d=7.33–7.26 (5H, m), 5.14 (2H, br s), 4.18–4.12 (1H, m), 4.08–3.90 (1H, m), 3.83–3.71 (2H, m), 2.39–2.00 (2H, m), 2.00–1.82 (2H, m), 1.24 (9H, s), 0.86 (9H, s), 0.03 (6H, br s); 13C NMR (CDCl3, 62.5 MHz) 136.1, 128.4, 128.1, 127.9, 67.2, 64.3, 50.7, 28.4, 25.9; FABHRMS (NBA) m/e 581.1824 ([M+Cs]+ C24H40N2O4Si requires 581.1822. Intermediate compound (1.0 equivalents; vida supra) was dissolved in MeOH (0.10 M) and a catalytic amount of 10% palladium on carbon was added. The mixture was stirred vigorously under a balloon of hydrogen until TLC indicated that the reaction was complete. Filtration and concentration afforded a clean product to give 1052B.

Figure 29:
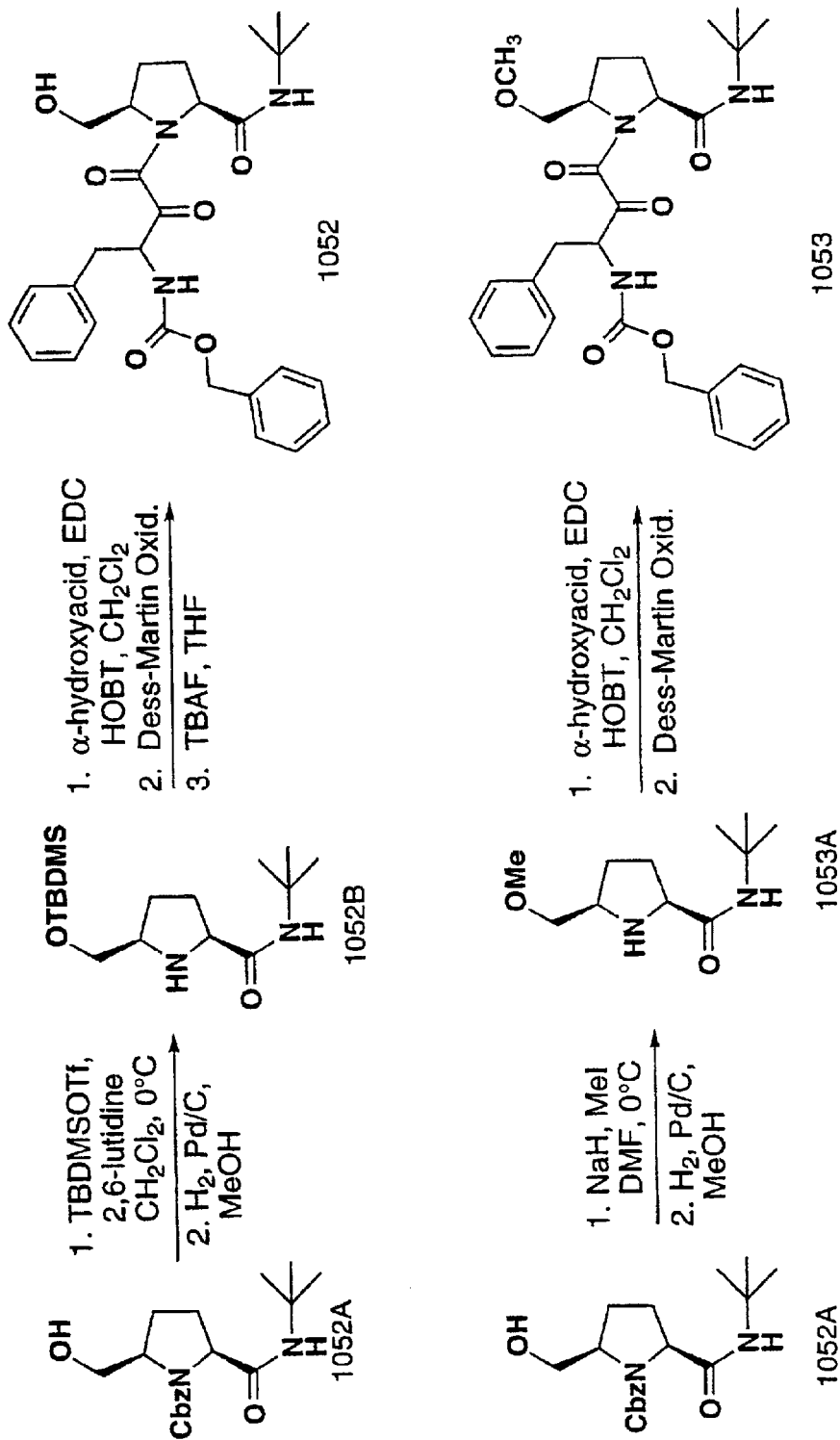
FIG. 29 illustrates the synthesis of α-ketoamide compound 1053 with the indicated substrate and reagents.

Synthesis of 2S,3S)-3-(N-Benzyloxycarbonyl)amino-2-hydroxy-4-phenylbutyryl-5'-cis-(tert-butyldimethylsilyloxymethyl)-L-prolyl-tert-butyl amide (intermediate en route to compound 1052; FIG. 29, step 1) α-Hydroxy acid 11 (62.5 mg, 0.19 mmol, 1.0 eq; vida supra), EDC (40 mg, 1.1 eq.), HOBT (28.2 mg, 1.1 eq.) were stirred in dry DMF (1 mL) at ambient temperature, under argon. After preactivation for 30 min., the amine 1052B (59 mg, 1.0 eq) dissolved in dry DMF (0.5 mL+2×0.5 mL washes) was cannulated into the activated acid mixture. After stirring for 12 hr, the reaction mixture was concentrated in vacuo, and EtOAc was added. The organic layer was washed with water (2×5 mL), dried over MgSO4, and solvent removed under reduced pressure. Flash chromatography eluting with 20% ethyl acetate in hexanes gave intermediate as a white crystalline solid (77 mg, 65%). $R_f$=0.59 (1:2 EtOAc/Hexanes); 1H NMR (CDCl3, 400 MHz): (mixture of two rotamers) d=7.32–7.09 (20H, m), 6.86 (1H, s), 6.42 (1H, s), 5.63 (1H, d, J=8.9 Hz), 5.42 (1H, d, J=8.8 Hz), 5.07 (1H, d, J=12.0 Hz), 5.00 (1H, d, J=12.0 Hz), 5.08–4.92 (2H, m), 4.53–4.38 (2H, m), 4.37–4.19 (3H, m), 4.12–3.97 (3H, m), 3.89–3.71 (2H, m), 3.63–3.52 (1H, m), 3.52–3.47 (1H, m), 2.90–2.62 (4H, m), 2.50–2.32 (1H, m), 2.20–1.60 (1H, m), 1.30 (9H, s), 1.27 (9H, s), 0.87 (9H, s), 0.86 (9H, s), 0.08 (3H, s), 0.06 (3H, s), 0.04 (3H, s), 0.01 (3H, s); 13C NMR (CDCl3, 100 MHz); FABHRMS (NBA) m/e 758.2618([M+Cs]+C34H51N3O6Si requires 758.2601.

Synthesis of intermediate to compound 1052 (step 2, FIG. 29) General Dess-Martin Oxidation Procedure: (2S,3S)-3-(N-Benzyloxycarbonyl)amino-2-keto-4-phenylbutyryl-5'-cis-(tert-butyldimethylsilyloxymethyl)-L-prolyl-tert-butyl amide.

The substrate X (28 mg, 0.044 mmol) was dissolved in dry CH2Cl2 (2 mL) and Dess-Martin periodinane (26 mg, 0.088 mmol, 2.0 eq.) was added. The reaction mixture was stirred at ambient temperature for 24 hr, then diluted with ethyl acetate (10 mL), and quenched by addition of sat'd sodium bicarbonate(aq.)(5 mL), and sodium thiosulfate. The aqueous phase was extracted with ethyl acetate (3×20 mL). The combined organic extracts were washed with water (10 mL), dried over MgSO4, and concentrated in vacuo to give the crude product. Flash chromatography eluting with 50% ethyl acetate in hexanes gave the desired product as a white solid (1:1 mixture of diastereomers). (26 mg, 95%) Rf=0.47 (1:2 EtOAc/Hexanes); 1H NMR (CDCl3, 400 MHz); d=7.36–7.13 (20H, m), 6.40 (1H, s), 6.07 (1H, s), 5.36 (1H, d, J=7.2 Hz), 5.18 (1H, d, J=6.8 Hz), 5.11–4.97 (5h, m), 4.96–4.90 (1H, m), 4.50–4.47 (1H, m), 4.22–4.18 (2H, m), 3.99 (1H, dd, J=9.6, 4.9 Hz), 3.96–3.87 (1H, m), 3.75 (1H, dd, J=10.0, 4.8 Hz), 3.53–3.32 (3H, m), 3.27 (1H, dd, J=14.2, 5.5 Hz), 3.18 (1H, dd, J=14.1, 8.1 Hz), 2.91 (1H, dd, J=14.0, 9.7 Hz), 2.40–2.28 (1H, m), 2.25–2.16 (1H, m), 2.08–1.97 (1H, m), 1.96–1.78 (2H, m), 1.72–1.52 (3H, m), 1.34 (9H, s), 1.31 (9H, s), 0.88 (9H, s), 0.86 (9H, s), 0.09 (3H, s), 0.06 (3H, s), 0.04 (3H, s), 0.03 (3H, s); 13C (CDCl3, 100 MHz); IR (NaCl) vmax 3332.3, 2955.0, 2856.0, 2358.1, 1714.7, 1634.1, 1537.8, 1454.8, 1258.0, 1094.6; FABHRMS (NBA) m/e 756.2469 ([M+Cs]+C34H49N3O6Si requires 756.2445.

Synthesis of compound 1052 (as illustrated in FIG. 29): To a 1.0 Molar solution of 1.0 equivalents substrate, TBAF (1.0 M solution in THF) was added (0.34 mL, 1.05 eq.) and the reaction monitored by TLC. After 30 min. at 0° C., the reaction was complete and the solvent was evaporated under reduced pressure. The crude material was applied to a short column of silica gel and eluted with 33% hexanes in ethyl acetate to give a yellow oil (162 mg, 94%).

Synthesis of N-(Benzyloxycarbonyl)-5-cis-(methoxynethyl)-L-proline-tert-butyl amide compound 1053A (FIG. 29). A solution of 1052A (156 mg, 0.467 mmol) in anhydrous DMF (3 mL) was cooled to 0° C. under argon. NaH, 60% disp. in mineral oil, (28.0 mg, 0.70 mmol, 1.5 eq.) was added and the suspension was allowed to stir for 20 min. Iodomethane (116 mL, 1.8 mmol, 4.0 eq.) was then added and the mixture stirred for 3 hr at 0° C. The reaction was quenched by addition of a few drops of 1N HCl(aq.) solution, and then diluted with H2O (10 mL). The aqueous layer was extracted with EtOAc (3×20 mL), dried over MgSO4, filtered, and evaporated under reduced pressure. Flash chromatography eluting with 50% ethyl acetate in hexanes gave an intermediate as a colorless oil (146 mg, 89%). Rf=0.25 (1:1 EtOAc/Hexanes). 1H NMR (CDCl3) 13C NMR (CDCl3, MHz).

FABHRMS (NBA) m/e 349.2119 ([M+H]+ C19H28N2O4 requires 349.21270.

To a solution of above intermediate (85 mg, 0.19 mmol) in MeOH (3 mL) was added a catalytic amount of 10% Pd/C and the mixture stirred under a balloon of H2 at ambient temperature. After 20 min, TLC indicated that the reaction was complete and the mixture was filtered through a bed of Celite and washed with MeOH. Removal of solvent under reduced pressure gave a colorless oil (89 mg, quant.) as compound 1053A which was used in the next step without further purification. 1H NMR (CDCl3, 400 MHz) d=5.64 (1H, br s), 4.21 (1H, dd, J=9.2, 5.0 Hz), 3.78–3.68 (1H, m), 3.53 (1H, dd, 9.8, 4.1 Hz), 3.46–3.37 (1H, m), 3.42 (3H, S), 2.41–2.31 (m, 1H), 2.06–1.89 (2H, m), 1.69–1.60 (1H, m), 1.36 (9H, s). 13C (CDCl3, 100 MHz) d 171.2, 73.4, 60.2, 59.2, 59.0, 51.0, 30.7, 28.6, 27.0. FABHRMS (NBA) m/e 215.1764 ([M+H]+ C11H22N2O2 requires 215.1760.

Synthesis of (2S,3S)-3-(N-Benzyloxycarbonyl)amino-2-hydroxy-4-phenylbutyryl-5'-cis-(methoxymethyl)-L-prolyl-tert-butyl Amide (Intermediate to Compound 1053, FIG. 29).

Synthesized according to the General Coupling Procedure outlined above and as illustrated in synthesis of compound 1052 (FIG. 29). Rf=0.30 (EtOAc: Hexanes 1:2) 1H NMR (CDCl$_3$, 400 MHz): (mixture of rotamers) d=7.33–7.17 (20H, m), 6.91 (2H, d, J=5.6 Hz), 5.75 (1H, d, J=8.8 Hz), 5.64 (1H, d, J=8.8 Hz), 5.07 (1H, d, J=12.3 Hz), 5.03 (2H, s), 4.91 (1H, d), 4.61–4.55 (1H, m), 4.53–4.38 (3H, m), 4.28–4.15 (4H, m), 4.02–3.95 (1H, m), 3.93–3.86±2H, m), 3.81–3.75 (1H, m), 3.46 (1H, d, J=8.7 Hz), 3.39–3.26 (3H, m), 3.35 (3H, s), 3.20 (3H, s), 2.93–2.84 (3H, m), 2.80–2.73 (1H, m), 2.42–2.35 (1H, m), 2.15–1.82 (3H, m), 1.80–1.74 (1H, m), 1.72–1.62 (1H, m), 1.30 (9H, s), 1.27 (9H, s); $^{13}$C NMR (CDCl3, 100 MHz) d=172.4, 171.6, 171.1, 169.9, 156.2, 156.0, 137.6, 137.2, 136.4, 136.2, 129.5, 129.4, 129.1, 128.5, 128.4, 128.3, 128.2, 128.0, 127.9, 127.8, 127.7, 126.9, 126.4, 73.2, 71.2, 71.0, 70.2, 66.6, 66.4, 61.8, 60.8, 60.7, 60.4, 59.5, 59.0, 58.8, 58.7 58.0, 55.3, 54.7, 54.5, 51.1, 50.8, 35.1, 29.8, 29.6, 28.5, 27.9, 26.2, 24.1, 21.0, 14.1; FABHRMS (NBA) m/e 658.1879 ([M+Cs]+ C29H39N3O6 requires 658.1893.

Synthesis of (2S,3S)-3-(N-Benzyloxyearbonyl)amino-2-keto-4-phenylbutyryl-5'-cis-(methoxymethyl)-L-prolyl-tert-butyl amide (compound 1053; FIG. 29)

Synthesized according to the General Dess-Martin procedure as noted above and as illustrated in the example for compound 1052 (FIG. 29). Rf=0.40 (1:1 EtOAc/Hexanes); 1H NMR (CDCl$_3$, 400 MHz) (1:1 mixture of diastereomers) d=7.33–7.16 (20H, m), 6.88 (1H, s), 6.79 (1H, s), 5.70 (1H, d, J=8.6 Hz), 5.26 (1H, d, J=7.1 Hz), 5.18–5.12 (2H, m), 5.08–4.92 (4H, m), 4.48–4.43 (2H, m), 4.28–4.22 (1H, m), 4.14–4.10 (1H, m), 4.09–4.02 (1H, m), 3.45 (1H, dd, J 9.5, 1.9 Hz), 3.37 (3H, s), 3.36–3.17 (6H, m), 3.15 (3H, s), 2.94 (1H, dd, J=13.9, 9.4 Hz), 2.42–2.30 (1H, m), 2.20–2.10 (1H, m), 2.08–1.82 (5H, m), 1.61–1.72 (1H, m), 1.34 (9H, s), 1.30 (9H, s); 13C (CDCl$_3$, 100 MHz); 198.0, 197.0, 171.1, 169.4, 164.9, 163.9, 155.9, 155.6, 136.3, 136.1, 129.7, 129.3, 128.7, 128.5, 128.4, 128.3, 128.1, 127.0, 126.8, 74.3, 70.4, 67.1, 66.8, 63.6, 61.2, 59.8, 58.8, 58.6, 58.5, 57.9, 57.6, 51.0, 50.9, 37.2, 29.9, 28.6, 27.4, 25.7, 24.9; IR (NaCl) vmax 3331.1, 2966.8, 2340.9, 1717.4, 1646.2, 1540.6, 1455.8, 1252.9, 1111.7, 1047.1; FABHRMS (NBA) m/e 656.1714

([M+Cs]+C29H37N3O6 requires 656.1737; (Found C, 66.24; H, 7.21; N, 7.78; C29H37N3O6 requires C, 66.50, H, 7.13; N, 8.03).

5.
Synthesis of para-(ortho-nitrobenzyloxy)-hydroxybenzyl bromide compound 1054A as illustrated in FIG. 30

Figure 30:
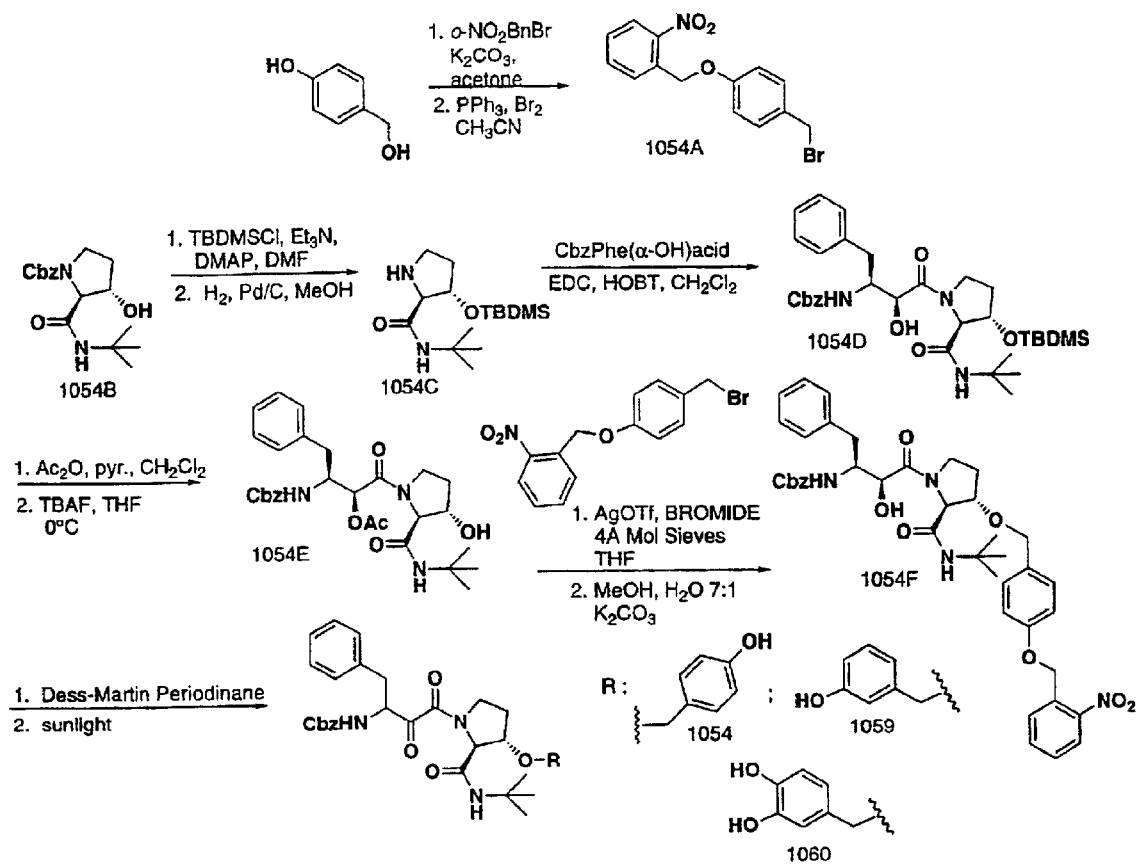
FIG. 30 illustrates the synthesis of α-ketoamide compounds 1054, 1059, and 1060 with the indicated substrates and reagents.
Figure 30:
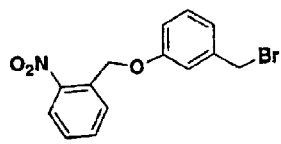
Figure 30:
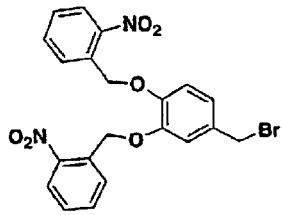
Figure 30:
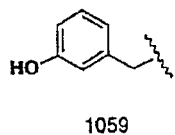
Figure 30:
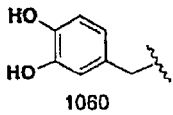

Step 1) To a solution of para-hydroxybenzyl alcohol (2.0 g, 16.1 mol; Aldrich) dissolved in dry acetone (15 mL) was added $K_2CO_3$ (4.45 g, 32.2 mmol, 2.0 eq.) and ortho-nitrobenzylbromide (3.83 g, 17.7 mmol, 1.1 eq). The mixture was stirred at ambient temperature for 16 hr and then the solution was concentrated in vacuo. The residue was taken up in EtOAc (100 mL) and then the organic layer was washed with H2O (2×30 mL), brine (30 mL) and dried over MgSO4. The product was recrystallized from Et2O/hexanes to give yellow needles (2.0 g, 60%) of para-(ortho-nitrobenzyl)-hydroxybenzyl alcohol. 1H NMR (CDCl3, 400 MHz) d=8.16 (1H, dd, J=8.2, 1.3 Hz), 7.88 (1H, dd, 7.9, 1.0 Hz), 7.68 (1H, dt, J=7.5, 1.2 Hz), 7.51–7.46 (1H, m), 7.32–7.26 (2H, m), 6.98–6.95 (2H, m), 5.48 (2H, s), 4.61 (2H, s); $^{13}C$ NMR (CDCl3, 100 MHz) d=157.6, 133.9, 128.7, 128.5, 128.2, 124.9, 114.8, 66.8, 64.9;

Step 2) To a suspension of $Ph_3P$ (1.03 g, 3.94 mmol, 1.02 eq.) in $CH_3CN$ (10 mL) cooled to 0° C. Bromine (0.20 mL, 3.86 mmol, 1.0 eq.) was added dropwise. The ice bath was then removed and a solution of para-(ortho-nitrobenzyl) hydroxybenzyl alcohol in 5 mL of CH3CN was added via cannulation. After stirring for 10 min., the CH3CN was removed in vacuo and the residue was extracted with hexanes (5×30 mL) and filtered through a pad of Celite. Concentration of the hexanes in vacuo yielded a fluffy white solid compound 1054A (1.19, 88%); 1H NMR (CDCl3, 400 MHz) d=8.17 (1H, d, J=8.2 Hz), 7.86 (1H, d, J=7.8 Hz), 7.68 (1H, t, J=7.4 Hz), 7.54–7.49 (1H, m), 7.34 (2H, d, J=8.4 Hz), 6.94 (2H, d, J=8.4 Hz), 5.49 (2H, s), 4.50 (2H, 5);

Synthesis of Trans-3'-(tert-butyldimethylsilyloxy) L-proline tert-butyl Amide Compound 1054C as Illustrated in FIG. 30

To a solution of N-(benzyloxycarbonyl)-trans-3'-hydroxyproline tert-butyl amide 1054B (739 mg, 2.31 mmol; vida supra; synthesized as 1050A, FIG. 27) in anhydrous DMF (10 mL) was added TBDMSCl (366 mg, 2.42 mmol, 1.05 eq), $Et_3N$ (0.35 mL, 2.54 mmol, 1.1 eq), and a catalytic amount of DMAP. The solution was stirred at ambient temperature for 15 hr and then was partitioned between EtOAc (60 mL) and H2O (30 mL). The organic layer was then washed with sat'd NH4Cl(aq.) solution (2×30 mL), water (30 mL), brine (30 mL), dried over MgSO4, and concentrated in vacuo to yield the crude material as a yellow oil. The yellow oil was then dissolved in MeOH (20 mL) and a catalytic amount of 10% Pd/C was added. The mixture was stirred vigorously under a balloon of $H_2$ for 1 hr. The mixture was then filtered through Celite and concentrated in vacuo to yield a yellow oil (690 mg, 99 i); $^1H$ NMR (CDCl3, 400 MHz) δ=6.97 (1H, s), 4.46 (1H, dd, J=9.1, 4.6 Hz), 3.76 (1H, d, J=4.04 Hz), 3.42 (1H, dt, J=10.6, 7.6 Hz), 3.21 (1H, ddd, J=10.6, 7.5, 5.8 Hz), 1.34 (9H, s), 0.89 (9H, s), 0.12 (3H, s), 0.11 (3H, s); $^{13}C$ NMR (CDCl$_3$, 100 MHz) d=168.3, 75.5, 67.8, 51.4, 44.1, 33.8, 28.6, 25.7, −4.6, −4.8; FAB-HRMS (NBA) m/e 301.2317 ([M+H]+ C15H32N2O2Si requires 301.2311);

Synthesis of (2S,3S)-3-N-(benzyloxycarbonyl)-amino-2-hydroxy-4-phenylbutyryl-trans-3'-(tert-butyldimethylsilyloxy)-L-prolyl-tert-butyl Amide Compound 1054D as Illustrated in FIG. 30.

Synthesized according to the general peptide coupling procedure outlined above as exemplified for compound 1052, FIG. 29. $^1H$ NMR (CDCl$_3$, 400 MHz) d=7.28–7.08 (10H, m), 6.48 (1H, s), 5.57 (1H, d, J=8.8 Hz), 5.08–4.93 (2H, m), 4.63–4.58 (1H, m), 4.52–4.38 (1H, m), 4.26 (1H, br s), 4.20–3.61 (4H, m), 1.24 (9H, s), 0.88 (9H, s), 0.09 (6H, s); $^{13}C$ NMR (CDCl$_3$, 100 MHz) d=171.4, 170.0, 168.5, 156.6, 156.1, 137.4, 136.2, 135.9, 129.1, 128.8, 128.4, 128.0, 127.9, 127.4, 126.4, 73.1, 71.6, 71.2, 69.7, 69.2, 66.6, 66.5, 54.8, 54.5, 51.4, 51.3, 45.9, 45.5, 34.5, 33.6, 32.9, 31.8, 28.5, 28.4, 25.7, 17.9, 14.1;

Synthesis of (2S,3S)-3-N-(benzyloxycarbonyl)-amino-2-acetoxy-4-phenylbutyryl-trans-3'-(tert-butyldimethylsilyloxy)-L-prolyl-tert-butyl Amide intermediate compound to 1054E as illustrated in FIG. 30. To a solution of (2S,3S)-3-N-(benzyloxycarbonyl)-amino-2-hydroxy-4-phenylbutyryl-trans-3'-(tert-butyldimethylsilyloxy)-L-prolyl-tert-butyl amide 1054D (216 mg, 0.35 mmol) in anhydrous $CH_2Cl_2$ was added acetic anhydride (67 mL, 0.71 mmol, 2.0 eq.), pyridine (71 mL, 0.882 mmol, 2.5 eq.). It was difficult to tell whether the reaction had gone to completion by monitoring by TLC, since the Rf values of the starting material and product were virtually identical. After stirring the reaction for 15 hr under argon, EtOAc (40 mL) was added and the solution was washed with sat'd NH4Cl(aq.) (20 mL), sat'd NaCO3 (aq.) (20 mL), water (20 mL) and brine (20 mL). The organic layer was dried over MgSO4, filtered, and concentrated to yield a white fluffy solid. (211 mg, 92%); 1H NMR (CDCl$_3$, 400 MHz) δ=7.33–7.13 (10H, m), 6.47 (1H, s), 5.57 (1H, d), 5.36–5.30 (1H, m), 5.02 (2H, s), 4.69–4.58 (1H, m), 4.39–4.31 (1H, m), 4.20–4.09 (1H, m), 3.87–3.57 (2H, m), 2.98–2.79 (2H, m), 2.26–2.22 (1H, m), 2.08 (3H, s), 1.95–1.85 (1H, m), 1.31 (9H, s), 0.87 (9H, s), 0.099 (6H, s); $^{13}C$ NMR (CDCl$_3$, 100 MHz) d=170.2, 169.9, 168.6, 167.8, 167.4, 166.5, 155.9, 136.9, 136.1, 128.9, 128.5, 128.4, 128.0, 127.8, 127.7, 126.6, 76.5, 73.3, 72.8, 71.3, 69.5, 69.4, 66.7, 66.5 52.7, 52.4, 51.4, 51.1, 45.5, 45.2, 35.5, 34.3, 33.8, 31.0, 28.5, 28.2, 25.6, 25.5, 20.5, 20.3, 17.9, 17.6; FAB-HRMS (NBA) m/e 786.2571 ([M+Cs)+ C35H51N3O7Si requires 786.2551);

Synthesis of (2S,3S)-3-N-(benzyloxycarbonyl)-amino-2-acetoxy-4-phenylbutyryl-trans-3'-hydroxy-L-prolyl-tert-butyl amide compound 1054E as illustrated in FIG. 30. The substrate (2S,3S)-3-N-(benzyloxycarbonyl)-amino-2-acetoxy-4-phenylbutyryl-trans-3'-(tert-butyldimethylsilyloxy)-L-prolyl-tert-butyl amide (1.0 equivalents; vida supra) was dissolved in THF and cooled to 0° C. TBAF (1.0 M solution in THF) was added (0.34 mL, 1.05 eq.) and the reaction monitored by TLC. After 30 min. at 0° C., the reaction was complete and the solvent was evaporated under reduced pressure. The crude material was applied to a short column of silica gel and eluted with 33% hexanes in ethyl acetate to give a yellow oil (162 mg, 94%). Synthesis of (2S,3S)-3-N-(benzyloxycarbonyl)-amino-2-hydroxy-4-phenylbutyryl-trans-3'-(para-(ortho-nitrobenzyl) benzyloxy)-L-prolyl-tert-butyl Amide Compound 1054F, FIG. 30.

To a solution of (2S,3S)-3-N-(benzyloxycarbonyl)-amino-2-acetoxy-4-phenylbutyryl-trans-3'-hydroxy-L-prolyl-tert-butyl amide dissolved in anhydrous THF (3 mL) was added para-(ortho-nitrobenzyl)hydroxybenzylbromide (106.4 mg, 0.331 mmol), 4A molecular sieves (spatula-full), and silver triflate (a spatula-full). The reaction was complete in 10 minutes at ambient temperature so it was immediately filtered through a pad of Celite and washed with Et2o. After flash chromatography eluting with 50% ethyl acetate in hexanes, a colorless oil was isolated (165 mg, 70%).

The substrate (2S,3S)-3-(N-Benzyloxycarbonyl)amino-2-acetoxy-4-phenylbutyryl-3'-trans-(para-(ortho-nitrobenzyl)benzyloxy]-L-prolyl-tert-butyl amide was dissolved in MeOH: H$_2$O (7 mL: 1 mL) and cooled to 0° C. K$_2$CO$_3$ (146 mg, 1.06 mmol, 5.0 eq.) was added and the cloudy mixture was allowed to warm gradually to RT. Monitoring the reaction by TLC was difficult because the starting material and product had nearly identical Rf values. The reaction was stirred at RT for an additional 30 min., and then the MeOH was removed in vacuo. The resulting residue was partitioned between water (20 mL) and EtOAc (30 mL) and dried over MgSO4, filtered, and concentrated to yield a colorless oil (155 mg, 99%).

Synthesis of (2S,3S)-3-N-(benzyloxycarbonyl)-amino-2-keto-4-phenylbutyryl-trans-3'-[para-hydroxybenzyloxy]-L-prolyl-tert-butyl amide compound 1054. Step 1) Synthesized according to the general Dess-Martin oxidation procedure as outlined above for compound 1052, FIG. 29.

Step 2) The substrate (2S,3S)-3-N-(benzyloxycarbonyl)-amino-2-keto-4-phenylbutyryl-trans-3'-[para-(ortho-nitrobenzyloxy)benzyloxy]-L-prolyl-tert-butyl amide was dissolved in CH$_2$Cl$_2$ (1 mL) and placed in the sunlight until TLC indicated that the reaction had gone to completion. The solution was concentrated in vacuo and purified by flash chromatography (eluent 33% ethyl acetate in hexanes) to yield a slightly yellow oil.

Alternative compounds 1059, 1060 and other hydroxybenzyloxyproline substituted α-keto amides The synthesis of the trans-3-meta-hydroxybenzyloxyproline substituted α-keto amides is done in an analogous fashion to that described above for the trans-3-para-hydroxybenzyl-substituted syste; 1059 and 1060 can be synthesized using the bromides shown in FIG. 30.

Figure 31:
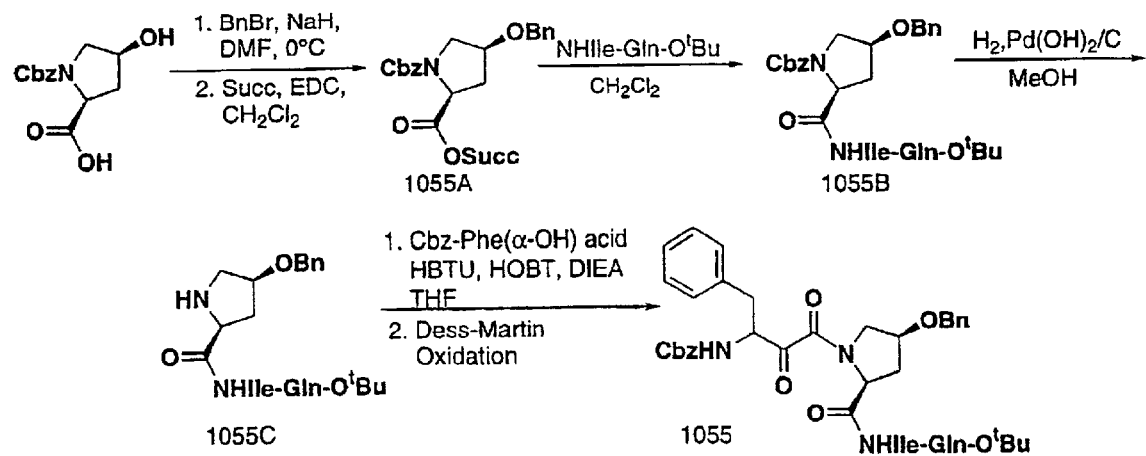
FIG. 31 illustrates the synthesis of α-ketoamide compound 1055 with the indicated substrate and reagents.

Synthesis of N-(benzyloxycarbonyl)-cis-4'-(benzyloxy)-L-proline succinate ester compound 1055A as illustrated in FIG. 31. Step 1) To an ice-cooled solution of N-(benzyloxycarbonyl)-cis-41'-hydroxyproline (290 mg, 1.09 mmol; Aldrich) in anhydrous DMF (2 mL) under argon was added NaH (60% disp. in mineral oil) (96 mg, 2.40 mmol, 2.2 eq.). The mixture was allowed to stir for 20 min., and then benzyl bromide (0.14 mL, 1.20 mmol, 1.1 eq.) was added. The mixture was allowed to stir for 1 hr at 0° C. and then quenched with a few drops of water. Saturated NaHCO$_3$ solution was added (10 mL) and the aqueous layer was washed with ethyl ether. The aqueous layer was then acidified to pH 2 with 1N HCl, extracted with ethyl acetate (3×20 mL), dried over MgSO$_4$, and concentrated to afford a yellow oil. (205 mg, 53%) The crude material was carried on without purification.

Step 2) To a solution of N-(benzyloxycarbonyl)-cis-4'-(benzyloxy)-L-proline (41 mg, 0.115 mmol) in anhydrous CH$_2$Cl$_2$ (2 mL) was added EDC (68 mg, 0.356 mmol, 3.1 eq.) and N-hydroxysuccinimide (40 mg, 0.345 mmol, 3.0 eq.). The solution was stirred for 2 hrs. The solvent was removed, and the residue was partitioned between ethyl ether and water (10 mL/5 mL). The water layer was extracted with ethyl ether and the combined organic layers were washed with brine (10 mL) and dried over MgSO4. Concentration followed by flash chromatography eluting with 9% methanol in ethyl acetate yielded the desired product as a white solid (51 mg, 98%) $^1$H NMR (CDCl$_3$, 400 MHz) (two distinct rotamers, only major rotamer noted here) d 7.38–7.25 (10H, m), 5.23 (1H, d, J=12.4 Hz, ab-Cbz), 5.10 (1H, d, 12.4 Hz ab-Cbz), 4.75 (1H, dd, J=9.4, 3.0 Hz, a-H), 4.63 (1H, d J=12.5 Hz, ab-Bn), 4.48 (1H, d, J=12.5 Hz, ab-Bn), 4.15–4.09 (1H, m, CH-OBn), 3.75–3.62 (2H, m, NCH2CHOBn), 2.82 (4H, s, succ.CH2), 2.65–2.62 (1H, m, NCH2CHOBnCH2), 2.47–2.34 (1H, m, NCH2CHOBnCH2);

Synthesis of N-(benzyloxycarbonyl)-cis--4' (benzyloxy)-L-proline-isoleucine-glutamine-tert-butyl ester compound 1055B. To a solution of N-(benzyloxycarbonyl)-cis-4'-(benzyloxy)-L-proline succinate ester 1055A (28 mg, 0.0619 mmol) in anhydrous CH$_2$Cl$_2$ (2 mL) was added the dipeptide H$_2$N-Ile-Gln-(OtBu ester) (39 mg, 0.123 mmol, 2 eq.) and the solution was stirred at ambient temperature for 45 min. The solution was diluted with CH$_2$Cl$_2$ (5 mL) and then washed with sat'd NH$_4$Cl solution (5 mL), sat'd NaHCO3 solution, brine (5 mL) and dried over MgSO4. Concentration followed by flash chromatography with 8% methanol in ethyl acetate afforded the desired product as a white solid (40 mg, 99). 1H NMR (CDCl$_3$, 400 MHz) d=7.36–7.27 (10H, m), 6.99 (1H, br s), 6.84 (1H, d, J=8.6 Hz), 6.75 (1H, br s), 5.80 (1H, br s), 5.15 (2H, s), 4.53–4.32 (4H, m), 4.33–4.30 (1H, m), 4.12–4.09 (1H, m), 3.71 (1H, d, J=11.9 Hz), 3.59–3.54 (1H, m), 2.64–2.61 (1H, m), 2.30–2.15 (4H, m), 2.00–1.85 (1H, m), 1.83–1.69 (1H, m), 1.53–1.38 (2H, m), 1.45 (9H, s), 1.00–0.93 (1H, m), 0.81–0.71 (6H, m); 13C NMR (CDCl3,100 MHz) d 175.2, 171.2, 170.5, 156.2, 137.4, 135.9, 81.9, 76.4, 70.5, 67.7, 60.6, 57.8, 53.4, 52.1, 36.7, 34.1, 31.7, 28.1, 24.5, 15.0, 11.2; FABHRMS (NBA) m/e 785.2520 ([M+Cs]+ C35H48N4O8 requires 785.2526);

Synthesis of cis-4-(benzyloxy)-L-proline-isoleucine-glutamine-tert-butyl Ester Compound 1055C as Illustrated in FIG. 31.

To a solution of N-(benzyloxycarbonyl)-cis--4'-(benzyloxy)-L-proline-isoleucine-glutamine-tert-butyl ester 1055B (60 mg, 0.092 mmol) in MeOH (2 mL) was added 20% palladium hydroxide on carbon (10 mg) and the suspension was stirred vigorously under a balloon of hydrogen at ambient temperature. After 5 min., TLC indicated that the reaction was complete. The suspension was filtered through a pad of celite and concentrated in vacuo to yield X (47 mg, quant.) 1H NMR (CD3OD, 400 MHz) d 7.33–7.23 (5H, m), 4.47 (1H, d, J=11.8 Hz), 4.41 (1H, d, J=11.8 Hz), 4.27–4.18 (2H, m), 4.17–4.13 (1H, m), 3.88 (1H, dd, J=7.8, 4.3 Hz), 3.20 (1H, d, J=11.7 Hz), 3.12 (1H, dd, J=11.7, 4.6 Hz), 2.36–2.17 (2H, m), 2.12–2.07 (1H, m), 1.92–1.75 (2H, m), 1.57–1.46 (1H, m), 1.49 (9, s), 1.16–1.05 (1H, m), 0.92–0.88 (3H, m), 0.85–0.75 (3H, m); 13C NMR (CD3OD, 100 MHz) d 177.4, 175.3, 173.3, 172.1, 139.6, 129.4, 128.9, 128.6, 82.9, 79.9, 71.9, 60.4, 59.0, 54.0, 53.0, 38.4, 37.1, 32.1, 32.5, 28.2, 25.8, 15.9, 11.5;

Synthesis of (2S,3S)-3-N-(benzyloxycarbonyl)-amino-2-keto-4-phenylbutyryl-cis-4'-benzyloxy-L-proline-isoleucine-glutamine-tert-butyl ester compound 1055 as illustrated in FIG. 31. The following substances were combined in a flask, under a bed of argon: α-hydroxy acid 11 (26 mg, 0.080 mmol, 1.2 eq.), amine 1055C (35 mg, 0.067 mmol), HBTU (30.5 mg, 0.080 mmol, 1.2 eq.), and HOBT (10.9 mg, 0.080 mmol, 1.2 eq.). Anhydrous THF (1 mL) was added, followed by DIEA (28 mL, 0.161 mmol, 2.4 eq.) and the solution was stirred for 18 hr at ambient temperature. After removal of the solvent in vacuo, the resulting residue was taken up in EtOAc (10 mL) and washed with sat'd NH$_4$Cl(aq) (2×5 mL), sat'd NaHCO$_3$(aq) (2×5 mL), water (1×5 mL), and brine (1×5 mL). The organic layer was then dried over MgSO4, filtered, and concentrated in vacuo to yield a crude yellow oil. After subjecting the crude oil to flash chromatography in 5% MeOH in $CH_2Cl_2$, a white solid was isolated (24 mg, 43% yield). Rf=0.33 (9:1 $CH_2Cl_2$), 1H NMR(CDCl3, 400 MHz) (major rotamer only) d=7.33–7.11 (15H, m), 7.11 (1H, d, J=8.4 Hz), 6.78 (1H, d, J=10.2 Hz), 6.71 (1H, s), 5.12 (1H, d, J=12.5 Hz), 4.89 (1H, d, J=12.5 Hz), 4.67–4.55 (1H, m), 4.55 (1H, d J=12.5 Hz), 4.50 (1H, d, J=12.5 Hz), 4.48–4.29 (3H, m), 4.19–4.03 (2H, m), 4.02–4.92 (1H, m), 3.74–3.66 (1H, m), 3.07 (2H, d, J=7.4 Hz), 2.52 (1H, d, J=14.3 Hz), 2.32–2.06 (4H, m), 2.05–1.86 (1H, m), 1.71–1.52 (1H, m), 1.42 (9H, s), 1.06–0.89 (1H, m), 0.83–0.59 (6H, m); 13C NMR (CDCl3, 100 MHz) d=175.5, 173.4, 171.5, 170.5, 170.4, 156.6, 137.9, 137.7, 137.1, 136.3, 129.2, 129.1, 128.5, 128.4, 127.9, 127.8, 127.7, 126.5, 82.1, 76.5, 71.6, 70.7, 66.5, 60.8, 57.8, 56.2, 53.1, 52.2, 37.0, 34.4, 33.3, 31.7, 27.9, 25.0, 24.6, 14.9, 10.9.

Step 2) The final product was obtained using the general Dess-Martin oxidation procedure as outlined above for compound 1052, FIG. 29 to produce compound 1055.

Figure 32:
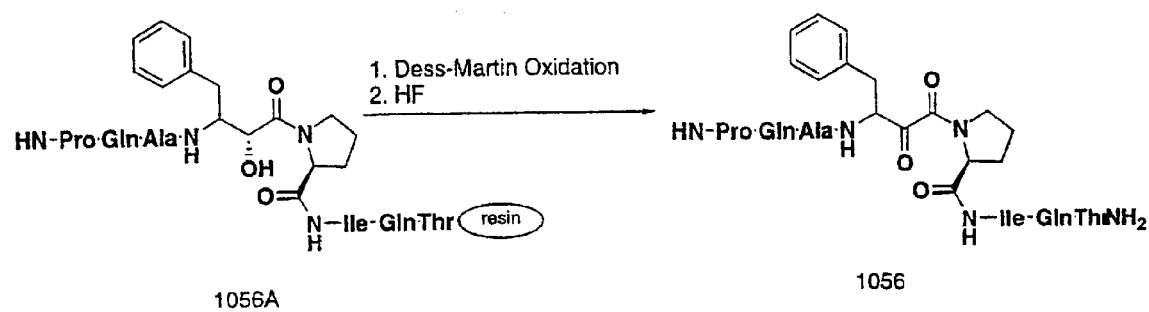
FIG. 32 illustrates the synthesis of α-ketoamide compound 1056 with the indicated substrate and reagents.

Synthesis of Compound 1056 as illustrated in FIG. 32. The following extended peptide isostere was synthesized on solid phase resin (MBHA) using standard peptide coupling conditions. The peptide was synthesized starting from the C-terminal end. N-BOC-Threonine was coupled to the resin (DCC, HOBT, DIEA), followed by deprotection of the amino group (TFA), and thorough washings with DMF and $CH_2Cl_2$. This standard coupling/deprotection/washing procedure was repeated seven times with the following N-BOC amino acids: (Gln, Ile, Pro, Phe (α-hydroxy acid, Ala, Gln, Pro). Subsequent Dess-Martin oxidation was performed while the peptide was still bound to the solid support. The resin-bound peptide was suspended in $CH_2Cl_2$, and Dess-Martin periodinane was added (2.0 eq). The resin was washed with copious amounts of water and MeOH through a fritted funnel. This procedure was repeated to ensure complete oxidation to the α-keto-amide.

Figure 33:
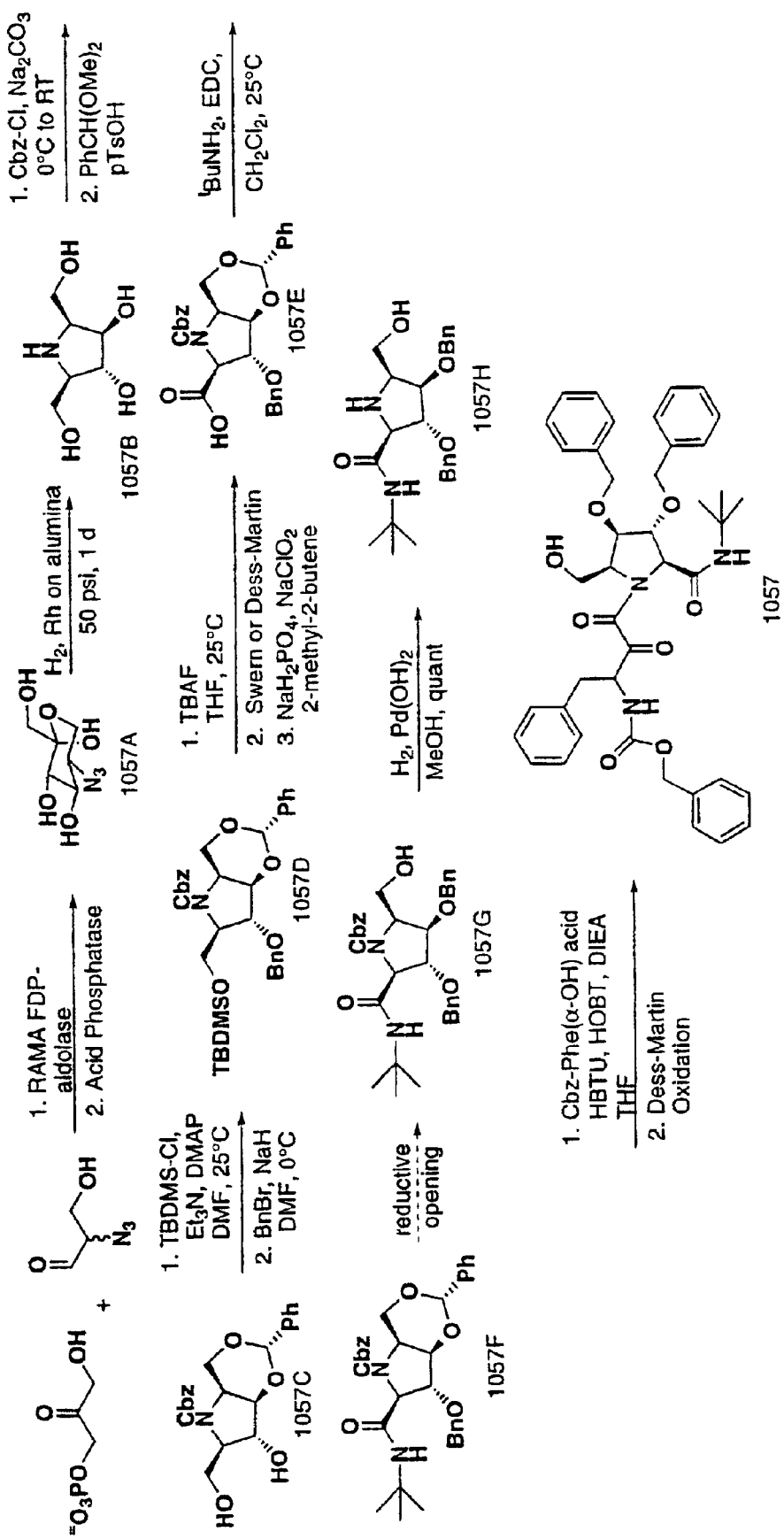
FIG. 33 illustrates the synthesis of α-ketoamide compound 1057 with the indicated substrate and reagents.

Cleavage of the peptide from the solid support was done in the standard anhydrous HF apparatus, and purified by reverse phase HPLC Synthesis of 2(R),5(R)-Bis(hydroxymethyl)-3(R),4(S)-dihydroxy-N-(benzyloxycarbonyl)-pyrrolidine-2,3-benzylidene acetal compound 1057C FIG. 33. To the substrate 2(R), 5(R)-Bis(hydroxymethyl)-3(R),4(S)-dihydroxy-N-(benzyloxycarbonyl)-pyrrolidine (267 mg, 0.90 mmol; synthesized according to the procedure in Slee et al. *J. Am. Chem. Soc.*, 1995, 117, 11867) dissolved in anhydrous DMF (1 mL) was added benzaldehyde dimethyl acetal (242 mL, 1.62 mmol, 1.8 eq.). A catalytic amount of PTSA was added and the solution was allowed to stir under argon for 6 hr, after which the solution was partitioned between H2O (30 mL) and EtOAc (30 mL), and the aqueous layer was extracted with EtOAc (2×30 mL). The pooled organic layers were washed with brine (20 mL), dried over MgSO4, filtered, and concentrated to yield a crude yellow oil. Subsequent flash column purification, eluting with 50% ethyl acetate in hexanes yielded a white foam 1057C (246 mg, 71%).

Synthesis of Compound 1057D as Illustrated in FIG. 33.

Step 1) To the 2(R), 5(R)-Bis(hydroxymethyl)-3(R),4(S)-dihydroxy-N-(benzyloxycarbonyl)-pyrrolidine-2,3-benzylidene acetal compound 1057C (784 mg, 2.04 mmol) in anhydrous DMF (4 mL) was added TBDMSCl (316 mg, 2.09 mmol, 1.02 eq.), triethylamine (310 mL, 2.24 mmol, 1.1 eq.), and a catalytic amount of DMAP. The solution was stirred under argon for 18 hr, and then the solution was partitioned between EtOAc (40 mL) and H2O (30 mL). The aqueous layer was extracted with EtOAc (2×40 mL), and the organic layers were washed with sat'd NH4Cl (aq.) (30 mL), brine (30 mL), dried over MgSO4, filtered, and concentrated in vacuo to yield a crude yellow oil. (914 mg, 90%).

Step 2) The crude yellow oil was redissolved in 5 mL of anhydrous DMF (5 mL), and the solution was cooled to 0° C. in an ice bath. NaH (52 mg, 2.16 mmol, 2.2 eq.), and benzyl bromide (0.128 mL, 1.08 mmol, 1.1 eq.) were added and the mixture was allowed to stir at 0° C. for 1 hr. The reaction was quenched with sat'd NH4Cl (5 mL), and then EtOAc (40 mL) was added. The organic layer was washed with sat'd NaHCO3(aq.) (30 mL), water (2×30 mL), and brine (30 mL). After drying over MgSO4, filtration, and concentration in vacuo, the crude product was isolated as a yellow oil.

Synthesis of Compound 1057E as Illustrated in FIG. 33.

Step 1) To the crude yellow oil (0.982 mmol) was added TBAF (1M in THF) (1.9 mL, 1.9 mmol, 2 eq.), and the solution was stirred 2 hr at ambient temperature. The solution was concentrated in vacuo and immediately applied to a short silica gel column, eluting with 33% ethyl acetate in hexanes. The product was isolated as a white foam (443 mg, 95%). Step 2) The white foam (0.191 mmol) was dissolved in $CH_2Cl_2$ (1 mL) and Dess Martin periodinane (112 mg, 2.0 mmol, 2.0 eq.) was added. After 1 hr, sodium thiosulfate (500 mg) and H2O (30 mL) were added, and the aqueous layer was extracted with EtOAc (3×30 mL), dried over MgSO4, filtered, and concentrated to yield a crude product which was dissolved in tert-butanol (2.5 mL). To this solution, 2-methyl-2-butene (2M solution) (2 mL) was added and then a solution of sodium chlorite (199 mg, 1.75 mmol, 9.2 eq.) and NaH2PO4 (354 mg, 1.32 mmol, 6.9 eq.) in $H_2O$ (1 mL) was added dropwise to the stirring substrate solution. After 1 hr, TLC indicated that the reaction was complete and the volatiles were removed in vacuo, and then remaining aqueous layer was extracted with diethyl ether (3×20 mL).

Synthesis of Compound 1057F as illustrated in FIG. 33. As illustrated in FIG. 33 the substrate 1057E (70 mg, 0.213 mmol), is dissolved in dry methylene chloride (3 mL). EDC, 1-(3-dimethylaminopropyl)-3-ethylcarbodiimide, (43 mg, 0.224 mmol) is added and the mixture is stirred for 30 minutes at room temperature. tertbutyl amine (73 mg, 0.255 mmol) is added and the reaction stirred for 18 hours. The reaction mixture is diluted with ethyl acetate (20 mL) and added to saturated ammonium chloride (30 mL). The aqueous phase is extracted with ethyl acetate (3×10 mL). The combined organic phases a re then washed with water (2×5 mL), 1 N HCl $_{(aq.)}$ (5 mL), saturated sodium bicarbonate solution $_{(aq.)}$ (50 mL), water (5 mL), brine (5 mL) and dried $(MgSO_4)$ before concentration in vacuo to give the crude product. Flash chromatography, eluting with 1:1 ethyl acetate/hexane gives the desired coupled product.

Synthesis of Compound 1057G as illustrated in FIG. 33. Reductive cleavage of the benzylidene ring is done using 1.1 equivalents DIBAL in 1.0 THF solution at 0° C. for 1 hour. The reaction mixture is diluted with ethyl acetate (20 mL) and add ed to saturated ammonium chloride (30 mL). The aqueous phase is extracted with ethyl acetate (3×10 mL). The combined organic phases are then washed with water (2×5 mL), 1 N HCl $_{(aq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired product.

Synthesis of Compound 1057H as illustrated in FIG. 33. Deprotection of the Cbz group will be achieved selectively (in the presence of benzyl groups) using 0.10 equivalents palladium hydroxide on carbon, as described in the procedure above for compound 1055C, FIG. 31.

Synthesis of Compound 1057 as Illustrated in FIG. 33.

As illustrated in FIG. 33, CB-Phe(α-OH) 11 (70 mg, 0.213 mmol), is dissolved in dry DMF (3 mL). HOBT, 1-hydroxybenzotriazole hydrate (31 mg, 0.22 mmol), EDC, 1-(3-dimethylaminopropyl)-3-ethylcarbodiimide, (43 mg, 0.224 mmol), DIEA, diisopropylethylamine, (122 μl, 0.703 mmol) are added and the mixture is stirred for 30 minutes at room temperature. The secondary amine 1057H (73 mg, 0.255 mmol) is added and the reaction stirred for 18 hours. The reaction mixture is diluted with ethyl acetate (20 mL) and added to saturated ammonium chloride (30 mL). The aqueous phase is extracted with ethyl acetate (3×10 mL). The combined organic phases are then washed with water (2×5 mL), 1 N HCl $_{(aq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired coupled product which is directly carried on to the next step for oxidation of the secondary alcohol as follows. The secondary alcohol (21 mg, 0.044 mmol) is dissolved in dry CH$_2$Cl$_2$ (2 mL), and Dess-Martin periodinane (26 mg, 0.088 mmol) added. The reaction mixture is stirred at ambient temperature for 24 hours, then diluted with ethyl acetate (10 mL) and quenched by addition of saturated sodium bicarbonate $_{(aq.)}$ (5 mL) and sodium thiosulfate. The aqueous phase is extracted with ethyl acetate (3×20 mL). The combined organic extracts washed with water (10 mL), brine (10 mL), dried (MgSO$_4$) and concentrated in vacuo to give the crude product. Flash chromatography eluting with 30% ethyl acetate in hexane gives the respective product 1057 as a 3:1 mixture of diastereomers (colorless oil) (20 mg, 95%) as a colorless oil.

Figure 34:
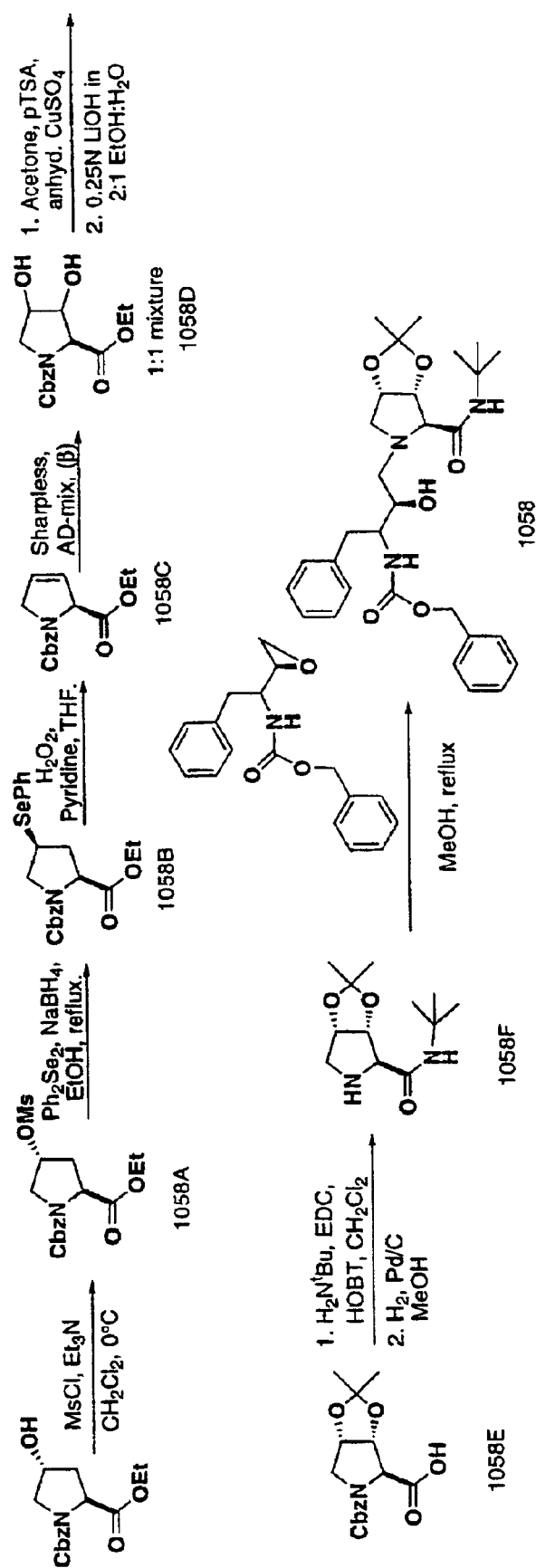
FIG. 34 illustrates the synthesis of α-ketoamide compound 1058 with the indicated substrate and reagents.

Synthesis of N-(benyloxycarbonyl)-3,4-didehydro-L-proline ethyl ester compound 1058C as illustrated in FIG. 34. Synthesized according to the procedure from *J. Org. Chem.* 1994, 59, 5192.

Synthesis of N-(benzyloxycarbonyl)-(3R,4S)-dihydroxy-L-proline Ethyl Ester Compound 1058D as Illustrated in FIG. 34.

To a solution of substrate (600 mg, 2.18 mmol) in t-butanol/H$_2$O (10 mL: 10 mL) was added AD-mix-b (3.0 g) and methanesulfonamide (290 mg, 3.05 mmol, 1.4 eq.), and reaction was stirred at 4° C. for 48 hr. The aqueous phase is extracted with ethyl acetate (3×20 mL). The combined organic extracts washed with water (10 mL), brine (10 mL), dried (MgSO$_4$) and concentrated in vacuo to give the crude product. Flash chromatography eluting with 30% ethyl acetate in hexane gives the respective product 1058D as a colorless oil.

Synthesis of N-(benzyloxycarbonyl)-(3R,4S)-dihydroacetal-L-proline ethyl ester compound 1059E as illustrated in FIG. 34. To the crude mixture of cis and trans-dihydroxy-L-proline ethyl ester was added acetone (10 mL), pTsA (a spatula-full), and CUSO$_4$ (spatula-full) and the mixture was refluxed and stirred for 24 h to give the corresponding acetonides. The aqueous phase is extracted with ethyl acetate (3×20 mL). The combined organic extracts washed with water (10 mL), brine (10 mL), dried (MgSO$_4$) and concentrated in vacuo to give the crude product. Flash chromatography eluting with 30% ethyl acetate in hexane gives the respective product 1058E as a colorless oil.

Synthesis of (3R,4S)-dihydroacetal-L-proline tert-butyl Amide Compound 1058F as Illustrated in FIG. 34

As illustrated in FIG. 34 the substrate 1058E (70 mg, 0.213 mmol), is dissolved in dry methylene chloride (3 mL). EDC, 1-(3-dimethylaminopropyl)-3-ethylcarbodiimide, (43 mg, 0.224 mmol) is added and the mixture is stirred for 30 minutes at room temperature. tert-butyl amine (73 mg, 0.255 mmol) is added and the reaction stirred for 18 hours. The reaction mixture is diluted with ethyl acetate (20 mL) and added to saturated ammonium chloride (30 mL). The aqueous phase is extracted with ethyl acetate (3×10 mL). The combined organic phases are then washed with water (2×5 mL), 1 N HCl $_{(aq.)}$ (5 mL), saturated sodium bicarbonate solution $_{(aq.)}$ (50 mL), water (5 mL), brine (5 mL) and dried (MgSO$_4$) before concentration in vacuo to give the crude product. Flash chromatography, eluting with 1:1 ethyl acetate/hexane gives the desired coupled product Step 2) The product was dissolved in MeOH (0.10 M) and a catalytic amount of 10% palladium on carbon was added. The mixture was stirred vigorously under a balloon of hydrogen until TLC indicated that the reaction was complete. Filtration and concentration afforded a clean product 1058F.

Synthesis of Compound 1058 as Illustrated in FIG. 34

To the pyrrolidine derivative 1058F (20 mg, 0.091 mmol) was added dry methanol (2 mL), Cbz-phenylalanyl epoxide 21 (27 mg, 0.091 mmol, 1.0 eq.) and triethylamine (14 μL, 0.100 mmol, 1.1 eq.). The solution was refluxed for 32 h, and then concentrated in vacuo. Flash chromatography, eluting with ethyl acetate provides the desired product as a clear oil to give respectively hydroxylethyl amine derivative 1058.

Preparation, Assay and Inhibition Analysis of the HIV Protease

Plasmid pLAC-PRO6.5 which contains the lacZ-protease fusion construct under the control of the rac promoter (composed of the *E. coli* ribosomal RNA promoter fused to lac operator) was prepared and transformed to *E. coli* JM103. To induce lacZ-pro synthesis, overnight culture of JM103 harboring pLAC-PRO6.5 (PRO 6-5) was diluted 50 fold with LB broth containing 300 g/mL ampicillin. Cells were grown at 37° C. for 1 h to A$_{600}$=0.2–0.3, lactose (0.4% final concentration) was then added to induce the synthesis of lacZ-protease fusion protein. After overnight growth, cells were harvested by centrifugation in a Sorvall GSA rotor at 6,000 rpm for 7 minutes. Cell paste from 250 mL culture was suspended in 10 mL lysis buffer (50 mM Tris, 2 mM EDTA, 2 mM DTT, 100 mM NaCl, pH 7.5) containing 200 g/mL lysozyme and stood at 4° C. overnight. The cell suspension was subsequently sonicated over a salted ice bath for 10 times with 10–15 pulses each at the maximal power output of the sonifier (Branson 450). Care was taken during sonication to keep the temperature of cell suspension below 10° C. The sonicates were then centrifuged at 6 k rpm in a GSA rotor for 10 minutes. The majority of the lacZ-pro fusion proteins were found in the pellet. The insoluble lacZ-pro proteins were solubilized and unfolded in an aqueous solution containing 8M urea, and 50 mM dithiothreitol (DTT) or 1% 2-mercaptoethanol at concentrations of 0.2 mg/mL to 0.4 mg/mL. To refold the lacZ-pro proteins, the protein suspension were diluted with 12 volumes of 10 mM Tris at pH 6.0 and incubated at room temperature overnight (final protein concentration at 15 g/mL to 30 g/mL). Under these conditions, the lacZ-pro proteins underwent autoproteolysis to yield the mature 10 kDa protease.

The renatured lacZ-protease fusion protein mixture was prepared as described above and freeze-dried in a lyophilizer overnight, resuspended in $H_2O$, and dialyzed against 10 mM Tris buffer at pH 8.0 overnight to remove urea. Under these conditions the mature HIV protease forms an insoluble precipitate and can be readily purified by low speed centrifugation at 2,000×g for 20 min. The precipitated protease was redissolved in 8M urea, 10 mM Tris, pH 8.0, 1 mM DTT and passed through a DEAE-Sephacel column or a Pharmacia monoQ column in the same buffer. The flow through fraction was collected and dialyzed against 10 mM Tris, pH 8.0, 1 mM DTT, and concentrated by lyophilization. Both SDS gel electrophoresis and immunoblot analysis and amino acid analysis showed homogeneity of the protease. This procedure routinely gave 2–3 mg of the mature protease per gram of *E. coli* cells.

The synthetic HIV-protease containing a thioester linkage available from CalBiochem (San Diego) can also be used. The enzyme activity was assayed with the fluorogenic substrate Ac-Thr-Ile-Nle-Phe(P—$NO_2$)-Gln-Arg-$NH_2$ (from CalBiochem, San Diego) according to the procedure described in the literature. Inhibition analysis was performed in the presence of the inhibitor and expressed with $IC_{50}$ (the concentration of inhibitor that causes 50% inhibition of the enzyme activity).

What is claimed is:

1. A mechanism based inhibitor of HIV or FIV aspartyl protease having the following structure:

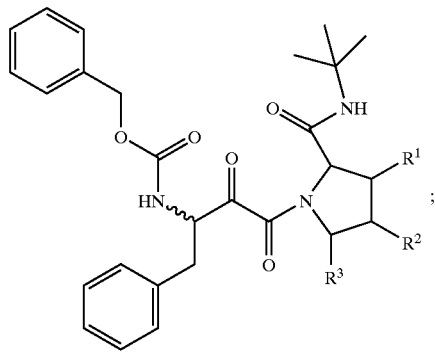

Wherein:
- $R^1$ is a radical selected from the group consisting of —H, —OH, —O($C_1$–$C_6$ alkyl), —OBn, —OCH$_2$C$_6$H$_4$(OH), and —OCH$_2$C$_6$H$_3$(OH)$_2$;
- $R^2$ is a radical selected from the group consisting of —H, —OH, —O($C_1$–$C_6$ alkyl), —OBn, —OCH$_2$C$_6$H$_4$(OH), and —OCH$_2$C$_6$H$_3$(OH)$_2$;
- $R^3$ is a radical selected from the group consisting of —H, —CH$_2$OH, and —CH$_2$O($C_1$–$C_6$ alkyl);

with the following provisos:
R$^1$, R$^2$ and R$^3$ cannot all be hydrogen.

2. The mechanism based inhibitor of claim 1 having following structure:

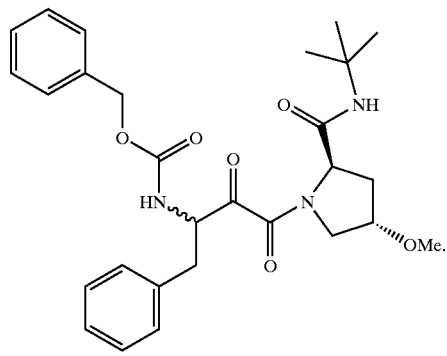

3. The mechanism based inhibitor of claim 1 having following structure:

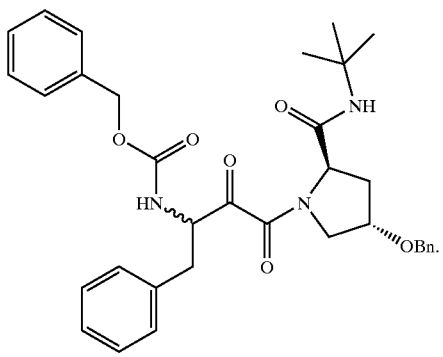

4. The mechanism based inhibitor of claim 1 having following structure:

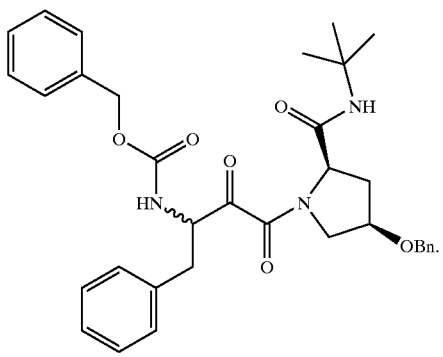

* * * * *

SEQUENCE LISTING

```
<160> NUMBER OF SEQ ID NOS: 7

<210> SEQ ID NO 1
<211> LENGTH: 8
<212> TYPE: PRT
<213> ORGANISM: Lentivirus Human Immunodeficiency virus 1

<400> SEQUENCE: 1

Ser Gln Asn Tyr Pro Ile Val Gln
1               5

<210> SEQ ID NO 2
<211> LENGTH: 8
<212> TYPE: PRT
<213> ORGANISM: Lentivirus feline immunodeficiency virus

<400> SEQUENCE: 2

Pro Gln Ala Tyr Pro Ile Gln Thr
1               5

<210> SEQ ID NO 3
<211> LENGTH: 6
<212> TYPE: PRT
<213> ORGANISM: Lentivirus feline immunodeficiency virus

<400> SEQUENCE: 3

Gln Ala Tyr Pro Ile Gln
1               5

<210> SEQ ID NO 4
<211> LENGTH: 6
<212> TYPE: PRT
<213> ORGANISM: Artificial Sequence
<220> FEATURE:
<221> NAME/KEY: MOD_RES
<222> LOCATION: 1
<223> OTHER INFORMATION: acylated with 2 amino-benzoic acid
<220> FEATURE:
<221> NAME/KEY: MOD_RES
<222> LOCATION: 4
<223> OTHER INFORMATION: para-nitro group on the phenyl ring of this
      phenylalanine
<221> NAME/KEY: AMIDATION
```

```
<222> LOCATION: 6
<223> OTHER INFORMATION: amidated with ammonia
<220> FEATURE:
<223> OTHER INFORMATION: Synthetic

<400> SEQUENCE: 4

Thr Ile Asn Phe Gln Arg
 1               5

<210> SEQ ID NO 5
<211> LENGTH: 17
<212> TYPE: PRT
<213> ORGANISM: Unknown
<220> FEATURE:
<223> OTHER INFORMATION: synthetic

<400> SEQUENCE: 5

Gly Lys Glu Glu Gly Pro Pro Gln Ala Tyr Pro Ile Gln Thr Val Asn
 1               5                  10                  15

Gly

<210> SEQ ID NO 6
<211> LENGTH: 6
<212> TYPE: PRT
<213> ORGANISM: Artificial Sequence
<220> FEATURE:
<223> OTHER INFORMATION: Commercially available fluorogenic substrate
      for the protease of the human immunodeficiency virus
<220> FEATURE:
<221> NAME/KEY: ACETYLATION
<222> LOCATION: 1
<220> FEATURE:
<221> NAME/KEY: MOD_RES
<222> LOCATION: 4
<223> OTHER INFORMATION: para-nitro group on the ring of phenylalanine
<220> FEATURE:
<221> NAME/KEY: AMIDATION
<222> LOCATION: 6
<223> OTHER INFORMATION: primary amide

<400> SEQUENCE: 6

Thr Ile Asn Phe Gln Arg
 1               5

<210> SEQ ID NO 7
<211> LENGTH: 8
<212> TYPE: PRT
<213> ORGANISM: Artificial Sequence
<220> FEATURE:
<221> NAME/KEY: MOD_RES
<222> LOCATION: 4
<223> OTHER INFORMATION: 3-amino-2-oxo-4-phenylbu-
      tyric acid residue
<221> NAME/KEY: AMIDATION
<222> LOCATION: 8
<223> OTHER INFORMATION: primary amide formed with
      ammonia
<220> FEATURE:
<223> OTHER INFORMATION: synthetic

<400> SEQUENCE: 7

Pro Gln Ala Phe Pro Ile Gln Thr
 1               5
```